US011326153B2

(12) United States Patent
Andersen et al.

(10) Patent No.: US 11,326,153 B2
(45) Date of Patent: May 10, 2022

(54) ALPHA-AMYLASE VARIANTS AND POLYNUCLEOTIDES ENCODING SAME

(71) Applicant: NOVOZYMES A/S, Bagsvaerd (DK)

(72) Inventors: Carsten Andersen, Vaerloese (DK);
Vasudeva Prahlada Rao, Bangalore (IN); Rakhi Saikia, Bangalore (IN);
Vivek Srivastava, Bangalore (IN);
Kendra Darlene Stallings, Wake Forest, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 16/770,797

(22) PCT Filed: Dec. 7, 2018

(86) PCT No.: PCT/US2018/064413
§ 371 (c)(1),
(2) Date: Jun. 8, 2020

(87) PCT Pub. No.: WO2019/113413
PCT Pub. Date: Jun. 13, 2019

(65) Prior Publication Data
US 2021/0189364 A1 Jun. 24, 2021

(30) Foreign Application Priority Data

Dec. 8, 2017 (IN) .............................. 201741044156
Aug. 20, 2018 (IN) .............................. 201841031044

(51) Int. Cl.
| | | |
|---|---|---|
| C12N 9/28 | (2006.01) |
| C12P 19/02 | (2006.01) |
| C12P 19/14 | (2006.01) |
| C13K 1/06 | (2006.01) |

(52) U.S. Cl.
CPC ............ *C12N 9/2417* (2013.01); *C12P 19/02* (2013.01); *C12P 19/14* (2013.01); *C12Y 302/01001* (2013.01); *C13K 1/06* (2013.01)

(58) Field of Classification Search
CPC ..... C12N 9/2414; C12N 9/2417; C12P 19/02; C12P 19/14; Y02E 50/10; C13K 1/06; C12Y 302/01001
See application file for complete search history.

(56) References Cited

U.S. PATENT DOCUMENTS

| | | |
|---|---|---|
| 8,084,240 B2 | 12/2011 | Cuevas |
| 8,507,243 B2 | 8/2013 | Poulson |
| 2014/0220635 A1* | 8/2014 | Andersen ............. C12N 9/2417 435/69.6 |

FOREIGN PATENT DOCUMENTS

| | | |
|---|---|---|
| WO | 96/23873 A1 | 8/1996 |
| WO | 99/19467 A2 | 4/1999 |
| WO | 00/60059 A2 | 10/2000 |
| WO | 2009/061379 A2 | 5/2009 |
| WO | 2009/061381 A2 | 5/2009 |
| WO | 2009/149130 A2 | 12/2009 |
| WO | 2010115021 A2 | 10/2010 |
| WO | 2011/082425 A2 | 7/2011 |
| WO | 2012/088303 A2 | 6/2012 |
| WO | 2013/057141 A2 | 4/2013 |
| WO | 2013/057143 A2 | 4/2013 |
| WO | 2013/082486 A1 | 6/2013 |
| WO | 2017/015329 A1 | 1/2015 |
| WO | 2015/050723 A1 | 4/2015 |

OTHER PUBLICATIONS

Gandhi et al, 2015, Biomed research international 2015, 1-9.
Nam et al, 2009, Genbank Accession No. AWV26017.
Pujadas et al, 2001, Mol Biol Evol, 38-54.
WO 2015-050723 A1—EBI Accession No. JE823914, 2015.
Exhibit "C", Janecek et al., "The invariant residues in the α-amylase family: just the catalytic triad," Biologia, Bratislava, 58/6: 1127-1132, 2003.
Exhibit "D", Devos et al., "Practical Limits of Function Prediction," PROTEINS: Structure, Function, and Genetics 41: 98-107 (2000).

* cited by examiner

*Primary Examiner* — Ganapathirama Raghu
(74) *Attorney, Agent, or Firm* — David Fazzolare

(57) ABSTRACT

The present invention relates to alpha-amylase variants comprising a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T E188P+K279N, E188P+K279Q, E188P+K279V, E188P+K279A, E188P+N275F, E188P+N275Y, E188P+N275W, and E188P+N275H, wherein the variant has at least 60%, at least 65%, at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27. The present invention also relates to polynucleotides encoding the variants; nucleic acid constructs, vectors, and host cells comprising the polynucleotides; and methods of using the variants.

71 Claims, No Drawings
Specification includes a Sequence Listing.

SEQUENCE LISTING

```
<160> NUMBER OF SEQ ID NOS: 27

<210> SEQ ID NO 1
<211> LENGTH: 484
<212> TYPE: PRT
<213> ORGANISM: Bacillus stearothermophilus

<400> SEQUENCE: 1

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
```

```
            145                 150                 155                 160
        Phe Asp Gly Val Asp Trp Asp Glu Ser Arg Lys Leu Ser Arg Ile Tyr
                        165                 170                 175
        Lys Phe Arg Gly Ile Gly Lys Ala Trp Asp Trp Glu Val Asp Thr Glu
                        180                 185                 190
        Asn Gly Asn Tyr Asp Tyr Leu Met Tyr Ala Asp Leu Asp Met Asp His
                        195                 200                 205
        Pro Glu Val Val Thr Glu Leu Lys Asn Trp Gly Lys Trp Tyr Val Asn
                        210                 215                 220
        Thr Thr Asn Ile Asp Gly Phe Arg Leu Asp Ala Val Lys His Ile Lys
        225                 230                 235                 240
        Phe Ser Phe Phe Pro Asp Trp Leu Ser Tyr Val Arg Ser Gln Thr Gly
                        245                 250                 255
        Lys Pro Leu Phe Thr Val Gly Glu Tyr Trp Ser Tyr Asp Ile Asn Lys
                        260                 265                 270
        Leu His Asn Tyr Ile Thr Lys Thr Asn Gly Thr Met Ser Leu Phe Asp
                        275                 280                 285
        Ala Pro Leu His Asn Lys Phe Tyr Thr Ala Ser Lys Ser Gly Gly Ala
                        290                 295                 300
        Phe Asp Met Arg Thr Leu Met Thr Asn Thr Leu Met Lys Asp Gln Pro
        305                 310                 315                 320
        Thr Leu Ala Val Thr Phe Val Asp Asn His Asp Thr Glu Pro Gly Gln
                        325                 330                 335
        Ala Leu Gln Ser Trp Val Asp Pro Trp Phe Lys Pro Leu Ala Tyr Ala
                        340                 345                 350
        Phe Ile Leu Thr Arg Gln Glu Gly Tyr Pro Cys Val Phe Tyr Gly Asp
                        355                 360                 365
        Tyr Tyr Gly Ile Pro Gln Tyr Asn Ile Pro Ser Leu Lys Ser Lys Ile
                        370                 375                 380
        Asp Pro Leu Leu Ile Ala Arg Arg Asp Tyr Ala Tyr Gly Thr Gln His
        385                 390                 395                 400
        Asp Tyr Leu Asp His Ser Asp Ile Ile Gly Trp Thr Arg Glu Gly Val
                        405                 410                 415
        Thr Glu Lys Pro Gly Ser Gly Leu Ala Ala Leu Ile Thr Asp Gly Pro
                        420                 425                 430
        Gly Gly Ser Lys Trp Met Tyr Val Gly Lys Gln His Ala Gly Lys Val
                        435                 440                 445
        Phe Tyr Asp Leu Thr Gly Asn Arg Ser Asp Thr Val Thr Ile Asn Ser
                        450                 455                 460
        Asp Gly Trp Gly Glu Phe Lys Val Asn Gly Gly Ser Val Ser Val Trp
        465                 470                 475                 480
        Val Pro Arg Lys

<210> SEQ ID NO 2
<211> LENGTH: 483
<212> TYPE: PRT
<213> ORGANISM: Bacillus licheniformis

<400> SEQUENCE: 2

Ala Asn Leu Asn Gly Thr Leu Met Gln Tyr Phe Glu Trp Tyr Met Pro
        1               5                   10                  15
        Asn Asp Gly Gln His Trp Arg Arg Leu Gln Asn Asp Ser Ala Tyr Leu
                        20                  25                  30
        Ala Glu His Gly Ile Thr Ala Val Trp Ile Pro Pro Ala Tyr Lys Gly
```

```
                35                  40                  45
Thr Ser Gln Ala Asp Val Gly Tyr Gly Ala Tyr Asp Leu Tyr Asp Leu
 50                  55                  60

Gly Glu Phe His Gln Lys Gly Thr Val Arg Thr Lys Tyr Gly Thr Lys
 65                  70                  75                  80

Gly Glu Leu Gln Ser Ala Ile Lys Ser Leu His Ser Arg Asp Ile Asn
                 85                  90                  95

Val Tyr Gly Asp Val Val Ile Asn His Lys Gly Gly Ala Asp Ala Thr
                100                 105                 110

Glu Asp Val Thr Ala Val Glu Val Asp Pro Ala Asp Arg Asn Arg Val
                115                 120                 125

Ile Ser Gly Glu His Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
                180                 185                 190

Tyr Asp Tyr Leu Met Tyr Ala Asp Ile Asp Tyr Asp His Pro Asp Val
                195                 200                 205

Ala Ala Glu Ile Lys Arg Trp Gly Thr Trp Tyr Ala Asn Glu Leu Gln
210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
                260                 265                 270

Tyr Leu Asn Lys Thr Asn Phe Asn His Ser Val Phe Asp Val Pro Leu
                275                 280                 285

His Tyr Gln Phe His Ala Ala Ser Thr Gln Gly Gly Gly Tyr Asp Met
290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
                340                 345                 350

Thr Arg Glu Ser Gly Tyr Pro Gln Val Phe Tyr Gly Asp Met Tyr Gly
                355                 360                 365

Thr Lys Gly Asp Ser Gln Arg Glu Ile Pro Ala Leu Lys His Lys Ile
                370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
                435                 440                 445

Trp His Asp Ile Thr Gly Asn Arg Ser Glu Pro Val Val Ile Asn Ser
450                 455                 460
```

```
Glu Gly Trp Gly Glu Phe His Val Asn Gly Gly Ser Val Ser Ile Tyr
465                 470                 475                 480

Val Gln Arg

<210> SEQ ID NO 3
<211> LENGTH: 481
<212> TYPE: PRT
<213> ORGANISM: Artificial
<220> FEATURE:
<223> OTHER INFORMATION: Bacillus licheniformis variant

<400> SEQUENCE: 3

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
                20                  25                  30

Ile Gly Ile Thr Ala Val Trp Ile Pro Pro Ala Tyr Lys Ala Ile Ser
            35                  40                  45

Gln Ala Asp Val Gly Tyr Gly Ala Tyr Asp Leu Tyr Asp Leu Gly Glu
        50                  55                  60

Phe His Gln Lys Gly Thr Val Arg Thr Lys Tyr Gly Thr Lys Gly Glu
65                  70                  75                  80

Leu Gln Ser Ala Ile Lys Ser Leu His Ser Arg Asp Ile Asn Val Tyr
                85                  90                  95

Gly Asp Val Val Ile Asn His Lys Ala Gly Ala Asp Ala Thr Glu Asp
                100                 105                 110

Val Thr Ala Val Glu Val Asp Pro Ala Asp Arg Asn Arg Val Ile Ser
            115                 120                 125

Gly Glu His Leu Ile Lys Ala Trp Thr His Phe His Phe Pro Gly Arg
130                 135                 140

Gly Ser Thr Tyr Ser Asp Phe Lys Trp Tyr Trp Tyr His Phe Asp Gly
145                 150                 155                 160

Thr Asp Trp Asp Glu Ser Arg Lys Leu Asn Arg Ile Tyr Lys Phe Gln
                165                 170                 175

Gly Lys Thr Trp Asp Trp Glu Val Ser Asn Glu Phe Gly Asn Tyr Asp
            180                 185                 190

Tyr Leu Met Tyr Ala Asp Phe Asp Tyr Asp His Pro Asp Val Val Ala
        195                 200                 205

Glu Ile Lys Arg Trp Gly Thr Trp Tyr Ala Asn Glu Leu Gln Leu Asp
210                 215                 220

Gly Phe Arg Leu Asp Ala Val Lys His Ile Lys Phe Ser Phe Leu Arg
225                 230                 235                 240

Asp Trp Val Asn His Val Arg Glu Lys Thr Gly Lys Glu Met Phe Thr
                245                 250                 255

Val Ala Glu Tyr Trp Ser Asn Asp Leu Gly Ala Leu Glu Asn Tyr Leu
            260                 265                 270

Asn Lys Thr Asn Phe Asn His Ser Val Phe Asp Val Pro Leu His Tyr
        275                 280                 285

Gln Phe His Ala Ala Ser Thr Gln Gly Gly Gly Tyr Asp Met Arg Lys
    290                 295                 300

Leu Leu Asn Gly Thr Val Val Ser Lys His Pro Leu Lys Ser Val Thr
305                 310                 315                 320

Phe Val Asp Asn His Asp Thr Gln Pro Gly Gln Ser Leu Glu Ser Thr
                325                 330                 335
```

```
Val Gln Thr Trp Phe Lys Pro Leu Ala Tyr Ala Phe Ile Leu Thr Arg
                340                 345                 350

Glu Ser Gly Tyr Pro Gln Val Phe Tyr Gly Asp Met Tyr Gly Thr Lys
            355                 360                 365

Gly Asp Ser Gln Arg Glu Ile Pro Ala Leu Lys His Lys Ile Glu Pro
        370                 375                 380

Ile Leu Lys Ala Arg Lys Gln Tyr Ala Tyr Gly Ala Gln His Asp Tyr
385                 390                 395                 400

Phe Asp His His Asp Ile Val Gly Trp Thr Arg Glu Gly Asp Ser Ser
                405                 410                 415

Val Ala Asn Ser Gly Leu Ala Ala Leu Ile Thr Asp Gly Pro Gly Gly
            420                 425                 430

Ala Lys Arg Met Tyr Val Gly Arg Gln Asn Ala Gly Glu Thr Trp His
        435                 440                 445

Asp Ile Thr Gly Asn Arg Ser Glu Pro Val Val Ile Asn Ser Glu Gly
    450                 455                 460

Trp Gly Glu Phe His Val Asn Gly Gly Ser Val Ser Ile Tyr Val Gln
465                 470                 475                 480

Arg

<210> SEQ ID NO 4
<211> LENGTH: 583
<212> TYPE: PRT
<213> ORGANISM: Bacillus subtilis

<400> SEQUENCE: 4

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
                20                  25                  30

Asn Leu Ser Ser Leu Gly Ile Thr Ala Leu Trp Leu Pro Pro Ala Tyr
            35                  40                  45

Lys Gly Thr Ser Gln Ser Asp Val Gly Tyr Gly Val Tyr Asp Leu Tyr
50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Thr Glu Leu Lys Asn Trp Gly Thr Trp Tyr Val
    210                 215                 220
```

```
Asn Thr Thr Asn Ile Asp Gly Phe Arg Leu Asp Ala Val Lys His Ile
225                 230                 235                 240

Lys Tyr Ser Phe Phe Pro Asp Trp Leu Thr Tyr Val Arg Asn Gln Thr
            245                 250                 255

Gly Lys Asn Leu Phe Ala Val Gly Glu Phe Trp Ser Tyr Asp Val Asn
        260                 265                 270

Lys Leu His Asn Tyr Ile Thr Lys Thr Asn Gly Ser Met Ser Leu Phe
    275                 280                 285

Asp Ala Pro Leu His Asn Asn Phe Tyr Thr Ala Ser Lys Ser Ser Gly
290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
            325                 330                 335

Gln Ser Leu Gln Ser Trp Val Glu Pro Trp Phe Lys Pro Leu Ala Tyr
        340                 345                 350

Ala Phe Ile Leu Thr Arg Gln Glu Gly Tyr Pro Cys Val Phe Tyr Gly
    355                 360                 365

Asp Tyr Tyr Gly Ile Pro Lys Tyr Asn Ile Pro Gly Leu Lys Ser Lys
370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
            405                 410                 415

Ile Asp Thr Lys Pro Asn Ser Gly Leu Ala Ala Leu Ile Thr Asp Gly
        420                 425                 430

Pro Gly Gly Ser Lys Trp Met Tyr Val Gly Lys Lys His Ala Gly Lys
    435                 440                 445

Val Phe Tyr Asp Leu Thr Gly Asn Arg Ser Asp Thr Val Thr Ile Asn
450                 455                 460

Ala Asp Gly Trp Gly Glu Phe Lys Val Asn Gly Gly Ser Val Ser Ile
465                 470                 475                 480

Trp Val Ala Lys Thr Ser Asn Val Thr Phe Thr Val Asn Asn Ala Thr
            485                 490                 495

Thr Thr Ser Gly Gln Asn Val Tyr Val Ala Asn Ile Pro Glu Leu
        500                 505                 510

Gly Asn Trp Asn Thr Ala Asn Ala Ile Lys Met Asn Pro Ser Ser Tyr
    515                 520                 525

Pro Thr Trp Lys Ala Thr Ile Ala Leu Pro Gln Gly Lys Ala Ile Glu
530                 535                 540

Phe Lys Phe Ile Lys Lys Asp Gln Ala Gly Asn Val Ile Trp Glu Ser
545                 550                 555                 560

Thr Ser Asn Arg Thr Tyr Thr Val Pro Phe Ser Ser Thr Gly Ser Tyr
            565                 570                 575

Thr Ala Ser Trp Asn Val Pro
        580

<210> SEQ ID NO 5
<211> LENGTH: 485
<212> TYPE: PRT
<213> ORGANISM: Cytophaga sp

<400> SEQUENCE: 5

Ala Ala Thr Asn Gly Thr Met Met Gln Tyr Phe Glu Trp Tyr Val Pro
1               5                   10                  15
```

```
Asn Asp Gly Gln Gln Trp Asn Arg Leu Arg Thr Asp Ala Pro Tyr Leu
            20                  25                  30

Ser Ser Val Gly Ile Thr Ala Val Trp Thr Pro Ala Tyr Lys Gly
        35                  40                  45

Thr Ser Gln Ala Asp Val Gly Tyr Gly Pro Tyr Asp Leu Tyr Asp Leu
 50                  55                  60

Gly Glu Phe Asn Gln Lys Gly Thr Val Arg Thr Lys Tyr Gly Thr Lys
 65                  70                  75                  80

Gly Glu Leu Lys Ser Ala Val Asn Thr Leu His Ser Asn Gly Ile Gln
                85                  90                  95

Val Tyr Gly Asp Val Val Met Asn His Lys Ala Gly Ala Asp Tyr Thr
            100                 105                 110

Glu Asn Val Thr Ala Val Glu Val Asn Pro Ser Asn Arg Asn Gln Glu
            115                 120                 125

Thr Ser Gly Glu Tyr Asn Ile Gln Ala Trp Thr Gly Phe Asn Phe Pro
130                 135                 140

Gly Arg Gly Thr Thr Tyr Ser Asn Phe Lys Trp Gln Trp Phe His Phe
145                 150                 155                 160

Asp Gly Thr Asp Trp Asp Gln Ser Arg Ser Leu Ser Arg Ile Phe Lys
                165                 170                 175

Phe Arg Gly Thr Gly Lys Ala Trp Asp Trp Glu Val Ser Ser Glu Asn
            180                 185                 190

Gly Asn Tyr Asp Tyr Leu Met Tyr Ala Asp Ile Asp Tyr Asp His Pro
        195                 200                 205

Asp Val Val Asn Glu Met Lys Lys Trp Gly Val Trp Tyr Ala Asn Glu
            210                 215                 220

Val Gly Leu Asp Gly Tyr Arg Leu Asp Ala Val Lys His Ile Lys Phe
225                 230                 235                 240

Ser Phe Leu Lys Asp Trp Val Asp Asn Ala Arg Ala Ala Thr Gly Lys
                245                 250                 255

Glu Met Phe Thr Val Gly Glu Tyr Trp Gln Asn Asp Leu Gly Ala Leu
            260                 265                 270

Asn Asn Tyr Leu Ala Lys Val Asn Tyr Asn Gln Ser Leu Phe Asp Ala
        275                 280                 285

Pro Leu His Tyr Asn Phe Tyr Ala Ala Ser Thr Gly Gly Gly Tyr Tyr
    290                 295                 300

Asp Met Arg Asn Ile Leu Asn Asn Thr Leu Val Ala Ser Asn Pro Thr
305                 310                 315                 320

Lys Ala Val Thr Leu Val Glu Asn His Asp Thr Gln Pro Gly Gln Ser
                325                 330                 335

Leu Glu Ser Thr Val Gln Pro Trp Phe Lys Pro Leu Ala Tyr Ala Phe
            340                 345                 350

Ile Leu Thr Arg Ser Gly Gly Tyr Pro Ser Val Phe Tyr Gly Asp Met
        355                 360                 365

Tyr Gly Thr Lys Gly Thr Thr Thr Arg Glu Ile Pro Ala Leu Lys Ser
    370                 375                 380

Lys Ile Glu Pro Leu Leu Lys Ala Arg Lys Asp Tyr Ala Tyr Gly Thr
385                 390                 395                 400

Gln Arg Asp Tyr Ile Asp Asn Pro Asp Val Ile Gly Trp Thr Arg Glu
                405                 410                 415

Gly Asp Ser Thr Lys Ala Lys Ser Gly Leu Ala Thr Val Ile Thr Asp
            420                 425                 430
```

```
Gly Pro Gly Gly Ser Lys Arg Met Tyr Val Gly Thr Ser Asn Ala Gly
            435                 440                 445

Glu Ile Trp Tyr Asp Leu Thr Gly Asn Arg Thr Asp Lys Ile Thr Ile
    450                 455                 460

Gly Ser Asp Gly Tyr Ala Thr Phe Pro Val Asn Gly Gly Ser Val Ser
465                 470                 475                 480

Val Trp Val Gln Gln
            485

<210> SEQ ID NO 6
<211> LENGTH: 485
<212> TYPE: PRT
<213> ORGANISM: Bacillus halmapalus

<400> SEQUENCE: 6

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
            85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
    130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
            165                 170                 175

Ile Tyr Lys Phe Arg Gly Asp Gly Lys Ala Trp Asp Trp Glu Val Asp
        180                 185                 190

Ser Glu Asn Gly Asn Tyr Asp Tyr Leu Met Tyr Ala Asp Val Asp Met
    195                 200                 205

Asp His Pro Glu Val Val Asn Glu Leu Arg Arg Trp Gly Glu Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
            245                 250                 255

Thr Gly Lys Glu Met Phe Ala Val Ala Glu Phe Trp Lys Asn Asp Leu
        260                 265                 270

Gly Ala Leu Glu Asn Tyr Leu Asn Lys Thr Asn Trp Asn His Ser Val
    275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320
```

His Pro Met His Ala Val Thr Phe Val Asp Asn His Asp Ser Gln Pro
              325                 330                 335

Gly Glu Ser Leu Glu Ser Phe Val Gln Glu Trp Phe Lys Pro Leu Ala
          340                 345                 350

Tyr Ala Leu Ile Leu Thr Arg Glu Gln Gly Tyr Pro Ser Val Phe Tyr
              355                 360                 365

Gly Asp Tyr Tyr Gly Ile Pro Thr His Ser Val Pro Ala Met Lys Ala
    370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
              405                 410                 415

Gly Asn Thr Thr His Pro Asn Ser Gly Leu Ala Thr Ile Met Ser Asp
              420                 425                 430

Gly Pro Gly Gly Glu Lys Trp Met Tyr Val Gly Gln Asn Lys Ala Gly
              435                 440                 445

Gln Val Trp His Asp Ile Thr Gly Asn Lys Pro Gly Thr Val Thr Ile
          450                 455                 460

Asn Ala Asp Gly Trp Ala Asn Phe Ser Val Asn Gly Ser Val Ser
465                 470                 475                 480

Ile Trp Val Lys Arg
              485

<210> SEQ ID NO 7
<211> LENGTH: 485
<212> TYPE: PRT
<213> ORGANISM: Bacillus sp

<400> SEQUENCE: 7

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
              20                  25                  30

Asn Leu Lys Asn Ala Gly Ile Thr Ala Ile Trp Ile Pro Pro Ala Trp
          35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Lys Ala Glu Leu Glu Arg Ala Ile Arg Ser Leu Lys Ala Asn Gly
              85                  90                  95

Ile Gln Val Tyr Gly Asp Val Val Met Asn His Lys Gly Gly Ala Asp
          100                 105                 110

Phe Thr Glu Arg Val Gln Ala Val Glu Val Asn Pro Gln Asn Arg Asn
      115                 120                 125

Gln Glu Val Ser Gly Thr Tyr Gln Ile Glu Ala Trp Thr Gly Phe Asn
    130                 135                 140

Phe Pro Gly Arg Gly Asn Gln His Ser Ser Phe Lys Trp Arg Trp Tyr
145                 150                 155                 160

His Phe Asp Gly Thr Asp Trp Asp Gln Ser Arg Gln Leu Ala Asn Arg
              165                 170                 175

Ile Tyr Lys Phe Arg Gly Asp Gly Lys Ala Trp Asp Trp Glu Val Asp
          180                 185                 190

Thr Glu Asn Gly Asn Tyr Asp Tyr Leu Met Tyr Ala Asp Val Asp Met

```
                195                 200                 205
Asp His Pro Glu Val Ile Asn Glu Leu Asn Arg Trp Gly Val Trp Tyr
    210                 215                 220

Ala Asn Thr Leu Asn Leu Asp Gly Phe Arg Leu Asp Ala Val Lys His
225                 230                 235                 240

Ile Lys Phe Ser Phe Met Arg Asp Trp Leu Gly His Val Arg Gly Gln
                245                 250                 255

Thr Gly Lys Asn Leu Phe Ala Val Ala Glu Tyr Trp Lys Asn Asp Leu
            260                 265                 270

Gly Ala Leu Glu Asn Tyr Leu Ser Lys Thr Asn Trp Thr Met Ser Ala
        275                 280                 285

Phe Asp Val Pro Leu His Tyr Asn Leu Tyr Gln Ala Ser Asn Ser Ser
290                 295                 300

Gly Asn Tyr Asp Met Arg Asn Leu Leu Asn Gly Thr Leu Val Gln Arg
305                 310                 315                 320

His Pro Ser His Ala Val Thr Phe Val Asp Asn His Asp Thr Gln Pro
                325                 330                 335

Gly Glu Ala Leu Glu Ser Phe Val Gln Gly Trp Phe Lys Pro Leu Ala
            340                 345                 350

Tyr Ala Thr Ile Leu Thr Arg Glu Gln Gly Tyr Pro Gln Val Phe Tyr
        355                 360                 365

Gly Asp Tyr Tyr Gly Ile Pro Ser Asp Gly Val Pro Ser Tyr Arg Gln
370                 375                 380

Gln Ile Asp Pro Leu Leu Lys Ala Arg Gln Gln Tyr Ala Tyr Gly Arg
385                 390                 395                 400

Gln His Asp Tyr Phe Asp His Trp Asp Val Ile Gly Trp Thr Arg Glu
                405                 410                 415

Gly Asn Ala Ser His Pro Asn Ser Gly Leu Ala Thr Ile Met Ser Asp
            420                 425                 430

Gly Pro Gly Gly Ser Lys Trp Met Tyr Val Gly Arg Gln Lys Ala Gly
        435                 440                 445

Glu Val Trp His Asp Met Thr Gly Asn Arg Ser Gly Thr Val Thr Ile
    450                 455                 460

Asn Gln Asp Gly Trp Gly His Phe Phe Val Asn Gly Gly Ser Val Ser
465                 470                 475                 480

Val Trp Val Lys Arg
            485

<210> SEQ ID NO 8
<211> LENGTH: 485
<212> TYPE: PRT
<213> ORGANISM: Bacillus sp

<400> SEQUENCE: 8

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80
```

```
Thr Arg Asn Gln Leu Gln Ala Ala Val Asn Ala Leu Lys Ser Asn Gly
                 85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
            115                 120                 125

Gln Glu Val Ser Gly Glu Tyr Thr Ile Glu Ala Trp Thr Lys Phe Asp
        130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
        210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
        370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
        435                 440                 445

Gln Val Trp Thr Asp Ile Thr Gly Asn Arg Ala Gly Thr Val Thr Ile
        450                 455                 460

Asn Ala Asp Gly Trp Gly Asn Phe Ser Val Asn Gly Gly Ser Val Ser
465                 470                 475                 480

Ile Trp Val Asn Lys
                485
```

```
<210> SEQ ID NO 9
<211> LENGTH: 481
<212> TYPE: PRT
<213> ORGANISM: Artificial
<220> FEATURE:
<223> OTHER INFORMATION: Variant based on SEQ ID NO: 3

<400> SEQUENCE: 9

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Ala Ile Ser
        35                  40                  45

Gln Ala Asp Val Gly Tyr Gly Ala Tyr Asp Leu Tyr Asp Leu Gly Glu
    50                  55                  60

Phe Trp Gln Lys Gly Thr Val Arg Thr Lys Tyr Gly Thr Lys Gly Glu
65                  70                  75                  80

Leu Gln Ser Ala Ile Lys Ser Leu His Ser Arg Asp Ile Asn Val Tyr
                85                  90                  95

Gly Asp Val Val Ile Asn His Lys Ala Gly Ala Asp Ala Thr Glu Asp
            100                 105                 110

Val Thr Ala Val Glu Val Asp Pro Ala Asp Arg Asn Arg Val Ile Ser
        115                 120                 125

Gly Glu His Leu Ile Lys Ala Trp Thr His Phe His Phe Pro Gly Arg
    130                 135                 140

Gly Ser Thr Tyr Ser Asp Phe Lys Trp Tyr Trp Tyr His Phe Asp Gly
145                 150                 155                 160

Thr Asp Trp Asp Glu Ser Arg Lys Leu Asn Arg Ile Tyr Leu Phe Gln
                165                 170                 175

Gly Lys Thr Trp Asp Trp Pro Val Ser Asn Glu Phe Gly Asn Tyr Asp
            180                 185                 190

Tyr Leu Met Tyr Ala Asp Tyr Asp Tyr Pro Asp Val Val Ala
        195                 200                 205

Glu Ile Thr Arg Trp Gly Thr Trp Tyr Ala Asn Glu Leu Gln Leu Asp
    210                 215                 220

Gly Phe Arg Leu Asp Ala Val Lys His Ile Lys Phe Ser Phe Leu Arg
225                 230                 235                 240

Asp Trp Val Asn His Val Arg Glu Lys Thr Gly Lys Glu Met Phe Thr
                245                 250                 255

Val Ala Glu Tyr Trp Ser Asn Asp Leu Gly Ala Leu Glu Asn Tyr Leu
            260                 265                 270

Asn Lys Thr Asn Phe Asn His Ser Val Phe Asp Val Pro Leu His Tyr
        275                 280                 285

Gln Phe His Ala Ala Ser Thr Gln Gly Gly Gly Tyr Asp Met Arg Lys
    290                 295                 300

Leu Leu Asn Gly Thr Val Val Ser Lys His Pro Leu Lys Ser Val Thr
305                 310                 315                 320

Phe Val Asp Asn His Asp Thr Gln Pro Gly Gln Ser Leu Glu Ser Thr
                325                 330                 335

Val Gln Thr Trp Phe Lys Pro Leu Ala Tyr Ala Phe Ile Leu Thr Arg
            340                 345                 350

Glu Ser Gly Tyr Pro Ser Val Phe Tyr Gly Asp Met Tyr Gly Thr Lys
        355                 360                 365

Gly Asp Ser Gln Arg Glu Ile Pro Ala Leu Lys His Lys Ile Glu Pro
```

```
              370                 375                 380
Ile Leu Lys Ala Arg Lys Gln Tyr Ala Tyr Gly Ala Gln His Asp Tyr
385                 390                 395                 400

Phe Asp His His Asp Ile Val Gly Trp Thr Arg Glu Gly Val Ser Ser
                405                 410                 415

Val Ala Asn Ser Gly Leu Ala Ala Leu Ile Thr Asp Gly Pro Gly Gly
                420                 425                 430

Ala Lys Trp Met Tyr Val Gly Arg Gln Asn Ala Gly Glu Thr Trp His
                435                 440                 445

Asp Ile Thr Gly Asn Arg Ser Glu Pro Val Val Ile Asn Ser Glu Gly
                450                 455                 460

Trp Gly Glu Phe His Val Asn Gly Gly Ser Val Ser Ile Tyr Val Gln
465                 470                 475                 480

Arg
```

<210> SEQ ID NO 10
<211> LENGTH: 481
<212> TYPE: PRT
<213> ORGANISM: Artificial
<220> FEATURE:
<223> OTHER INFORMATION: Variant based on SEQ ID NO: 3

<400> SEQUENCE: 10

```
Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
                20                  25                  30

Ile Gly Ile Thr Ala Val Trp Ile Pro Pro Ala Tyr Lys Ala Ile Ser
                35                  40                  45

Gln Ala Asp Val Gly Tyr Gly Ala Tyr Asp Leu Tyr Asp Leu Gly Glu
            50                  55                  60

Phe Trp Gln Lys Gly Thr Val Arg Thr Lys Tyr Gly Thr Lys Gly Glu
65                  70                  75                  80

Leu Gln Ser Ala Ile Lys Ser Leu His Ser Arg Asp Ile Asn Val Tyr
                85                  90                  95

Gly Asp Val Val Ile Asn His Lys Ala Gly Ala Asp Ala Thr Glu Asp
                100                 105                 110

Val Gln Ala Val Glu Val Asp Pro Ala Asp Arg Asn Arg Val Ile Ser
            115                 120                 125

Gly Glu His Leu Ile Lys Ala Trp Thr His Phe His Phe Pro Gly Arg
130                 135                 140

Gly Ser Thr Tyr Ser Asp Phe Lys Trp Tyr Trp Tyr His Phe Asp Gly
145                 150                 155                 160

Thr Asp Trp Asp Glu Ser Arg Lys Leu Asn Arg Ile Tyr Leu Phe Gln
                165                 170                 175

Gly Lys Thr Trp Asp Trp Pro Val Ser Asn Glu Phe Gly Asn Tyr Asp
            180                 185                 190

Tyr Leu Met Tyr Ala Asp Tyr Asp Tyr Asp Tyr Pro Asp Val Val Ala
            195                 200                 205

Glu Ile Thr Arg Trp Gly Thr Trp Tyr Ala Asn Glu Leu Gln Leu Asp
            210                 215                 220

Gly Phe Arg Leu Asp Ala Val Lys His Ile Lys Phe Ser Phe Leu Arg
225                 230                 235                 240

Asp Trp Val Asn His Val Arg Glu Lys Thr Gly Lys Glu Met Phe Thr
                245                 250                 255
```

-continued

Val Ala Glu Tyr Trp Ser Asn Asp Leu Gly Ala Leu Glu Asn Tyr Leu
             260                 265                 270

Asn Lys Thr Asn Phe Asn His Ser Val Phe Asp Val Pro Leu His Tyr
         275                 280                 285

Gln Phe His Ala Ala Ser Thr Gln Gly Gly Gly Tyr Asp Met Arg Lys
     290                 295                 300

Leu Leu Asn Gly Thr Val Val Ser Lys His Pro Leu Lys Ser Val Thr
305                 310                 315                 320

Phe Val Asp Asn His Asp Thr Gln Pro Gly Gln Ser Leu Glu Ser Thr
                 325                 330                 335

Val Gln Thr Trp Phe Lys Pro Leu Ala Tyr Ala Phe Ile Leu Thr Arg
             340                 345                 350

Glu Ser Gly Tyr Pro Ser Val Phe Tyr Gly Asp Met Tyr Gly Thr Lys
         355                 360                 365

Gly Asp Ser Gln Arg Glu Ile Pro Ala Leu Lys His Lys Ile Glu Pro
     370                 375                 380

Ile Leu Lys Ala Arg Lys Gln Tyr Ala Tyr Gly Ala Gln His Asp Tyr
385                 390                 395                 400

Phe Asp His His Asp Ile Val Gly Trp Thr Arg Glu Gly Val Ser Ser
                 405                 410                 415

Val Ala Asn Ser Gly Leu Ala Ala Leu Ile Thr Asp Gly Pro Gly Gly
             420                 425                 430

Ala Lys Trp Met Tyr Val Gly Arg Gln Asn Ala Gly Glu Thr Trp His
         435                 440                 445

Asp Ile Thr Gly Asn Arg Ser Glu Pro Val Val Ile Asn Ser Glu Gly
     450                 455                 460

Trp Gly Glu Phe His Val Asn Gly Gly Ser Val Ser Ile Tyr Val Gln
465                 470                 475                 480

Arg

<210> SEQ ID NO 11
<211> LENGTH: 491
<212> TYPE: PRT
<213> ORGANISM: Artificial
<220> FEATURE:
<223> OTHER INFORMATION: Variant based on SEQ ID NO: 1

<400> SEQUENCE: 11

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
             20                  25                  30

Leu Ser Ser Leu Gly Ile Thr Ala Leu Trp Leu Pro Pro Ala Tyr Lys
         35                  40                  45

Gly Thr Ser Arg Ser Asp Val Gly Tyr Gly Ala Tyr Asp Leu Tyr Asp
     50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                 85                  90                  95

Gln Val Tyr Ala Asp Val Val Phe Asp His Lys Gly Gly Ala Asp Gly
             100                 105                 110

Thr Glu Trp Val Asp Ala Val Glu Val Asn Pro Ser Asp Arg Asn Gln
         115                 120                 125

```
Val Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Leu Phe Glu Gly Lys Ala Trp Asp Trp Glu Val Asp Thr Glu Phe Gly
                180                 185                 190

Asn Tyr Asp Tyr Leu Met Tyr Ala Asp Leu Asp Met Asp His Pro Glu
            195                 200                 205

Val Thr Thr Glu Leu Lys Asn Trp Gly Lys Trp Tyr Val Asn Thr Thr
    210                 215                 220

Asn Ile Asp Gly Phe Arg Leu Asp Ala Val Lys His Ile Lys Phe Ser
225                 230                 235                 240

Phe Phe Pro Asp Trp Leu Ser Tyr Val Arg Ser Ser Thr Gly Lys Pro
                245                 250                 255

Leu Phe Thr Val Gly Glu Tyr Trp Ser Gly Asp Ile Asn Lys Leu His
                260                 265                 270

Asn Tyr Ile Thr Lys Thr Asp Gly Thr Val Ser Leu Phe Asp Ala Pro
            275                 280                 285

Leu His Tyr Lys Phe Tyr Asn Ala Ser Lys Ser Gly Gly Ala Phe Asp
    290                 295                 300

Met Arg Thr Leu Met Thr Asn Thr Leu Met Lys Asp Gln Pro Thr Leu
305                 310                 315                 320

Ala Val Thr Phe Val Asp Asn His Asp Thr Glu Pro Gly Gln Ala Leu
                325                 330                 335

Gln Ser Trp Val Asp Pro Trp Phe Lys Pro Leu Ala Tyr Ala Phe Ile
                340                 345                 350

Leu Thr Arg Gln Glu Gly Tyr Pro Cys Val Phe Tyr Gly Asp Tyr Tyr
            355                 360                 365

Gly Ile Pro Gln Tyr Asn Ile Pro Ser Leu Lys Ser Lys Ile Asp Pro
    370                 375                 380

Leu Leu Ile Ala Arg Arg Asp Tyr Ala Tyr Gly Thr Gln His Asp Tyr
385                 390                 395                 400

Leu Asp His Ser Asp Ile Ile Gly Trp Thr Arg Glu Gly Gly Thr Glu
                405                 410                 415

Lys Pro Gly Ser Gly Leu Ala Ala Leu Ile Thr Asp Gly Pro Gly Gly
                420                 425                 430

Ser Lys Trp Met Tyr Val Gly Lys Gln His Ala Gly Lys Val Phe Tyr
            435                 440                 445

Asp Leu Thr Gly Asn Arg Ser Asp Thr Val Thr Ile Asn Ser Asp Gly
    450                 455                 460

Trp Gly Glu Phe Lys Val Asn Gly Gly Ser Val Ser Val Trp Val Pro
465                 470                 475                 480

Arg Lys Thr Thr Val Ser Thr Ile Ala Arg Pro
                485                 490

<210> SEQ ID NO 12
<211> LENGTH: 489
<212> TYPE: PRT
<213> ORGANISM: Exiguobacterium acetylicum

<400> SEQUENCE: 12

Ala Gly Lys Ala Thr Ala Asp Asn Gly Thr Met Met Gln Tyr Phe Glu
1               5                   10                  15
```

Trp Tyr Val Pro Asn Asp Gly Asn His Trp Asn Arg Leu Gly Ser Asp
            20                  25                  30

Ala Thr Lys Leu Asp Gln Leu Gly Ile Thr Ser Val Trp Ile Pro Pro
            35                  40                  45

Ala Tyr Lys Gly Thr Ser Gln Asn Asp Val Gly Tyr Gly Ala Tyr Asp
50                  55                  60

Leu Tyr Asp Leu Gly Glu Phe Asn Gln Lys Gly Thr Val Arg Thr Lys
65                  70                  75                  80

Tyr Gly Thr Lys Ala Gln Leu Lys Thr Ala Ile Gly Gln Leu His Thr
                85                  90                  95

Ala Gly Ile Asp Val Tyr Gly Asp Val Val Met Asn His Lys Gly Gly
            100                 105                 110

Ala Asp Phe Thr Glu Ala Val Thr Ala Val Glu Ile Asn Pro Gly Asn
            115                 120                 125

Arg Asn Gln Glu Ile Ser Gly Asp Tyr Gln Ile Gln Ala Trp Thr Gly
130                 135                 140

Phe Asn Phe Ala Ala Arg Asn Asn Leu Tyr Ser Asn Phe Lys Trp Lys
145                 150                 155                 160

Trp Tyr His Phe Asp Gly Thr Asp Trp Asp Gln Ser Arg Ser Lys Ser
                165                 170                 175

Ala Ile Tyr Lys Phe Arg Gly Thr Gly Lys Ala Trp Asp Thr Asp Val
            180                 185                 190

Ser Thr Glu Asn Gly Asn Tyr Asp Tyr Leu Met Tyr Ala Asp Leu Asp
            195                 200                 205

Phe Asp His Pro Glu Val Gln Gln Glu Met Lys Asn Trp Gly Lys Trp
            210                 215                 220

Tyr Val Asn Glu Leu Gly Leu Asp Gly Phe Arg Leu Asp Ala Val Lys
225                 230                 235                 240

His Ile Lys His Gly Tyr Leu Ala Asp Trp Leu Ala Asn Val Arg Gln
                245                 250                 255

Thr Thr Gly Lys Pro Leu Phe Thr Val Ala Glu Tyr Trp Gln Asn Asp
            260                 265                 270

Leu Gly Thr Leu Gln Asn Tyr Leu Ser Arg Thr Asn Tyr Gln Gln Ser
            275                 280                 285

Val Phe Asp Ala Pro Leu His Tyr Lys Phe Glu Gln Ala Ser Lys Gly
            290                 295                 300

Gly Gly Tyr Tyr Asp Met Arg Thr Ile Phe Asp Gly Thr Leu Val Lys
305                 310                 315                 320

Ser Asn Pro Val Gln Ala Val Thr Leu Val Glu Asn His Asp Ser Gln
                325                 330                 335

Pro Gly Gln Ser Leu Glu Ser Thr Val Gln Ser Trp Phe Lys Pro Leu
            340                 345                 350

Ala Tyr Ala Met Ile Leu Thr Arg Glu Gln Gly Tyr Pro Ser Val Phe
            355                 360                 365

Tyr Gly Asp Tyr Tyr Gly Thr Lys Gly Thr Ser Asn Arg Glu Ile Pro
            370                 375                 380

Ala Leu Ala Ser Lys Ile Asp Pro Leu Leu Lys Ala Arg Lys Asp Phe
385                 390                 395                 400

Ala Phe Gly Lys Gln Asn Asp Tyr Leu Asp Asn Gln Asp Ile Ile Gly
                405                 410                 415

Trp Thr Arg Glu Gly Val Ser Asp Arg Ala Lys Ser Gly Leu Ala Thr
            420                 425                 430

```
Ile Leu Ser Asp Gly Pro Gly Ser Lys Trp Met Tyr Val Gly Leu
            435                 440                 445

Gln Asn Lys Gly Glu Val Trp Thr Asp Ile Thr Gly Asn Asn Thr Ala
        450                 455                 460

Ser Val Thr Ile Asn Gln Asp Gly Tyr Gly Gln Phe Phe Val Asn Gly
465                 470                 475                 480

Gly Ser Val Ser Val Tyr Arg Gln Gln
                485

<210> SEQ ID NO 13
<211> LENGTH: 483
<212> TYPE: PRT
<213> ORGANISM: Exiguobacterium sibiricum

<400> SEQUENCE: 13

Asp Asn Gly Thr Met Met Gln Tyr Phe Glu Trp Tyr Val Pro Asn Asp
1               5                   10                  15

Gly Asn His Trp Asn Arg Leu Gly Ser Asp Ser Thr Lys Leu Asp Gln
            20                  25                  30

Leu Gly Ile Thr Ser Val Trp Ile Pro Pro Ala Tyr Lys Gly Thr Thr
        35                  40                  45

Gln Asn Asp Val Gly Tyr Gly Ala Tyr Asp Leu Tyr Asp Leu Gly Glu
    50                  55                  60

Phe Asn Gln Lys Gly Thr Val Arg Thr Lys Tyr Gly Thr Lys Ala Gln
65                  70                  75                  80

Leu Lys Thr Ala Ile Asn Gln Leu His Thr Ala Gly Ile Asp Val Tyr
                85                  90                  95

Gly Asp Val Val Met Asn His Lys Gly Gly Ala Asp Phe Thr Glu Ala
            100                 105                 110

Val Thr Ala Val Glu Val Asn Gly Ser Asn Arg Asn Gln Glu Ile Ser
        115                 120                 125

Gly Asp Tyr Gln Ile Gln Ala Trp Thr Gly Phe Asp Phe Ala Ala Arg
    130                 135                 140

Asn Asn Thr Tyr Ser Asn Phe Lys Trp Lys Trp Tyr His Phe Asp Gly
145                 150                 155                 160

Thr Asp Trp Asp Gln Ser Arg Ser Lys Ser Ala Ile Tyr Lys Phe Arg
                165                 170                 175

Gly Thr Gly Lys Ala Trp Asp Thr Asp Val Ser Thr Glu Asn Gly Asn
            180                 185                 190

Tyr Asp Tyr Leu Met Tyr Ala Asp Ile Asp Phe Asp His Pro Glu Val
        195                 200                 205

Gln Gln Glu Met Lys Asn Trp Gly Lys Trp Tyr Val Asn Glu Leu Gly
    210                 215                 220

Leu Asp Gly Phe Arg Leu Asp Ala Val Lys His Ile Lys His Gly Tyr
225                 230                 235                 240

Leu Ala Asp Trp Leu Ala Asn Val Arg Gln Thr Thr Gly Lys Pro Leu
                245                 250                 255

Phe Thr Val Ala Glu Tyr Trp Gln Asn Asp Leu Gly Thr Leu Gln Asn
            260                 265                 270

Tyr Leu Ser Arg Thr Asn Tyr Gln Gln Ser Val Phe Asp Ala Pro Leu
        275                 280                 285

His Tyr Lys Phe Glu Gln Ala Ser Lys Gly Gly Tyr Tyr Asp Met
    290                 295                 300

Arg Thr Ile Phe Asp Gly Thr Leu Val Lys Thr Asn Pro Val Gln Ala
305                 310                 315                 320
```

```
Val Thr Leu Val Glu Asn His Asp Ser Gln Pro Gly Gln Ser Leu Glu
                325                 330                 335

Ser Thr Val Gln Ser Trp Phe Lys Pro Leu Ala Tyr Ala Met Ile Leu
                340                 345                 350

Thr Arg Glu Gln Gly Tyr Pro Ser Val Phe Tyr Gly Asp Tyr Tyr Gly
                355                 360                 365

Thr Lys Gly Thr Ser Asn Arg Glu Ile Pro Ala Leu Ala Ser Lys Ile
            370                 375                 380

Asp Pro Leu Leu Lys Ala Arg Lys Asp Phe Ala Phe Gly Lys Gln Asn
385                 390                 395                 400

Asp Tyr Leu Asp Asn Ala Asp Val Ile Gly Trp Thr Arg Glu Gly Val
                405                 410                 415

Thr Asp Arg Ala Lys Ser Gly Leu Ala Thr Ile Leu Ser Asp Gly Pro
                420                 425                 430

Gly Gly Ser Lys Trp Met Tyr Val Gly Leu Gln Asn Lys Gly Glu Val
                435                 440                 445

Trp Thr Asp Ile Thr Gly Asn Asn Thr Ala Ser Val Thr Ile Asn Gln
                450                 455                 460

Asp Gly Tyr Gly Gln Phe Phe Val Asn Gly Ser Val Ser Val Tyr
465                 470                 475                 480

Arg Gln Gln

<210> SEQ ID NO 14
<211> LENGTH: 480
<212> TYPE: PRT
<213> ORGANISM: Paenibacillus curdlanilyticus

<400> SEQUENCE: 14

Ala Asp Asn Gly Thr Ile Met Gln Tyr Phe Glu Trp Tyr Leu Pro Asn
1               5                   10                  15

Asp Gly Ala His Trp Asn Arg Leu Asn Asn Asp Ala Gln Asn Leu Lys
                20                  25                  30

Asn Val Gly Ile Thr Ala Val Trp Ile Pro Pro Ala Tyr Lys Gly Gly
                35                  40                  45

Ser Ser Ala Asp Val Gly Tyr Gly Val Tyr Asp Thr Tyr Asp Leu Gly
            50                  55                  60

Glu Phe Asn Gln Lys Gly Thr Val Arg Thr Lys Tyr Gly Thr Lys Ser
65                  70                  75                  80

Glu Leu Ile Ser Ala Val Asn Asn Leu His Ala Lys Gly Ile Ala Val
                85                  90                  95

Tyr Gly Asp Val Val Leu Asn His Arg Met Asn Ala Asp Ala Thr Glu
                100                 105                 110

Leu Val Asp Ala Val Glu Val Asp Pro Asn Asn Arg Asn Val Glu Thr
                115                 120                 125

Thr Ser Thr Tyr Gln Ile Gln Ala Trp Thr Gln Tyr Asp Phe Pro Gly
            130                 135                 140

Arg Gly Asn Thr Tyr Ser Ser Phe Lys Trp Arg Trp Tyr His Phe Asp
145                 150                 155                 160

Gly Val Asp Trp Asp Gln Ser Arg Gly Leu Asn Arg Ile Tyr Lys Leu
                165                 170                 175

Arg Gly Asp Gly Lys Asp Trp Asp Trp Glu Val Asp Ser Glu Tyr Gly
                180                 185                 190

Asn Tyr Asp Tyr Leu Met Gly Ala Asp Leu Asp Phe Asn His Pro Asp
            195                 200                 205
```

Val Val Asn Glu Thr Lys Thr Trp Gly Lys Trp Phe Val Asn Thr Val
    210                 215                 220

Asn Leu Asp Gly Val Arg Leu Asp Ala Val Lys His Ile Lys Phe Asp
225                 230                 235                 240

Phe Met Arg Asp Trp Val Asn Asn Val Arg Ser Thr Thr Gly Lys Asn
                245                 250                 255

Leu Phe Ala Val Gly Glu Tyr Trp His Tyr Asp Val Asn Lys Leu Asn
                260                 265                 270

Ser Tyr Ile Thr Lys Thr Asn Gly Thr Met Ser Leu Phe Asp Val Pro
            275                 280                 285

Leu His Phe Arg Phe Tyr Asp Ala Ser Asn Gly Gly Gly Tyr Asp
290                 295                 300

Met Arg Asn Leu Leu Asn Asn Thr Leu Met Ser Ser Asn Pro Met Lys
305                 310                 315                 320

Ala Val Thr Phe Val Glu Asn His Asp Thr Gln Pro Thr Gln Ala Leu
                325                 330                 335

Gln Ser Thr Val Gln Ser Trp Phe Lys Pro Leu Ala Tyr Ala Thr Ile
                340                 345                 350

Leu Thr Arg Glu Gln Gly Tyr Pro Cys Val Phe Tyr Gly Asp Tyr Tyr
            355                 360                 365

Gly Thr Ser Asp Gly Lys Ile Ser Ser Tyr Lys Pro Ile Met Asp Lys
370                 375                 380

Leu Leu Asn Ala Arg Lys Val Tyr Ala Tyr Gly Thr Gln Arg Asp Tyr
385                 390                 395                 400

Phe Asp His Pro Asp Ile Val Gly Trp Thr Arg Glu Gly Asp Ala Ala
                405                 410                 415

His Ala Gly Ser Gly Leu Ala Thr Leu Ile Thr Asp Gly Pro Gly Gly
            420                 425                 430

Ser Lys Trp Met Tyr Val Gly Thr Ser Lys Ala Gly Gln Val Trp Thr
                435                 440                 445

Asp Lys Thr Gly Asn Arg Ser Gly Thr Val Thr Ile Asp Ala Asn Gly
        450                 455                 460

Trp Gly Asn Phe Trp Val Asn Gly Gly Ser Val Ser Val Trp Ala Lys
465                 470                 475                 480

<210> SEQ ID NO 15
<211> LENGTH: 483
<212> TYPE: PRT
<213> ORGANISM: Bacillus megaterium

<400> SEQUENCE: 15

Met Glu Arg Asn His Thr Ile Met Gln Phe Phe Glu Trp His Val Pro
1               5                   10                  15

Ala Asp Gly Glu His Trp Gln Arg Leu Lys Glu Leu Ala Pro Gln Leu
                20                  25                  30

Lys Glu Gln Gly Ile Asp Ser Val Trp Ile Pro Pro Val Thr Lys Gly
            35                  40                  45

Val Ser Ser Glu Asp Asn Gly Tyr Gly Val Tyr Asp Leu Tyr Asp Leu
50                  55                  60

Gly Glu Phe Asp Gln Lys Gly Thr Val Arg Thr Lys Tyr Gly Thr Lys
65                  70                  75                  80

Gln Glu Leu His Glu Ala Ile Asp Ala Cys His Asn His Gly Ile Asn
                85                  90                  95

Val Tyr Val Asp Ile Val Met Asn His Lys Ala Ala Ala Asp Glu Lys

```
                100             105             110
Glu Thr Phe His Val Ile Glu Val Asp Pro Met Asn Arg Thr Glu Glu
            115                 120             125
Ile Ser Glu Pro Phe Glu Ile Glu Gly Trp Thr Lys Phe Thr Phe Glu
        130                 135             140
Gly Arg Gly Asp Lys Tyr Ser Ser Phe Lys Trp Asn Phe Asn His Phe
145                 150                 155                 160
Asn Gly Thr Asp Tyr Asp Asp Lys Asn Gly Lys Glu Gly Val Phe Arg
                165                 170                 175
Ile Ala Gly Glu Asn Lys Ser Trp Asn Glu Asn Val Asp Gln Glu Phe
            180                 185             190
Gly Asn Tyr Asp Tyr Leu Met Phe Ala Asn Ile Asp Tyr Asp His Pro
        195                 200             205
Glu Val Arg Glu Glu Met Ile Asn Trp Gly Lys Trp Leu Ala Asp Thr
    210                 215             220
Leu Gln Cys Asp Gly Tyr Arg Leu Asp Ala Ile Lys His Ile Asn His
225                 230                 235                 240
Asp Phe Ile Lys Glu Phe Ala His Glu Leu Ser Ser Gln Glu Lys
                245                 250                 255
Pro Phe Tyr Phe Val Gly Glu Phe Trp Asn Pro Glu Leu Thr Ala Cys
            260                 265             270
Gln Glu Phe Leu Asp Val Ile Asp Tyr Gln Ile Asp Leu Phe Asp Val
        275                 280             285
Ser Leu His Tyr Lys Leu His Glu Ala Ser Gln Gln Gly Arg Asp Phe
    290                 295             300
Asp Leu Thr Thr Ile Phe Asp Thr Leu Val Lys Thr His Pro Leu
305                 310                 315                 320
Asn Val Val Thr Phe Val Asp Asn His Asp Ser Gln Pro Asn Glu Ser
                325                 330                 335
Leu Glu Ser Trp Val Glu Asp Trp Phe Lys Gln Ser Ala Tyr Ala Leu
            340                 345             350
Ile Leu Leu Arg Glu Asp Gly Tyr Pro Cys Val Phe Tyr Gly Asp Tyr
        355                 360             365
Phe Gly Ile Gly Gly Glu His Pro Ile Glu Gly Lys Glu Lys Asp Ile
    370                 375             380
Ser Ala Leu Leu His Val Arg Tyr Asp Lys Ala Tyr Gly Gln Gln Asp
385                 390                 395                 400
Asp Tyr Phe Asp His Pro Asn Thr Ile Gly Trp Val Arg His Gly Val
                405                 410                 415
Glu Glu Phe Glu Lys Ser Gly Cys Ala Val Val Met Ser Asn Gly Glu
            420                 425             430
Asp Gly Glu Lys Arg Met Phe Val Gly Glu His Arg Ser Gly Gln Thr
        435                 440             445
Trp Ile Asp Phe Thr Asn Asn Arg Glu Asp Gln Val Val Ile Glu Glu
    450                 455             460
Asp Gly Tyr Gly Gln Phe Pro Val Asn Gly Gly Ser Val Ser Val Trp
465                 470                 475                 480
Ala Glu Ala

<210> SEQ ID NO 16
<211> LENGTH: 486
<212> TYPE: PRT
<213> ORGANISM: Alicyclobacillus Sp.18711
```

```
<400> SEQUENCE: 16

Ala Phe Ala Gly Asp Asn Gly Thr Met Met Gln Tyr Phe Glu Trp Tyr
1               5                   10                  15

Leu Pro Asn Asp Gly Thr Leu Trp Thr Lys Met Gly Ser Asp Ala Ser
            20                  25                  30

His Leu Lys Ser Ile Gly Ile Thr Gly Val Trp Phe Pro Pro Ala Tyr
        35                  40                  45

Lys Gly Gln Ser Gln Ser Asp Val Gly Tyr Gly Val Tyr Asp Met Tyr
    50                  55                  60

Asp Leu Gly Glu Phe Asn Gln Lys Gly Thr Val Arg Thr Lys Tyr Gly
65                  70                  75                  80

Thr Lys Ala Gln Leu Gln Ser Ala Ile Thr Ser Leu His Asn Asn Gly
                85                  90                  95

Ile Gln Ala Tyr Gly Asp Val Val Leu Asn His Arg Met Gly Ala Asp
            100                 105                 110

Ala Thr Glu Thr Ile Ser Ala Val Glu Val Asn Pro Ser Asn Arg Asn
        115                 120                 125

Gln Val Thr Ser Gly Ala Tyr Asn Ile Ser Ala Trp Thr Asp Phe Glu
    130                 135                 140

Phe Pro Gly Arg Gly Asn Thr Tyr Ser Ser Phe Lys Trp His Ser Tyr
145                 150                 155                 160

Tyr Phe Asp Gly Val Asp Trp Asp Gln Ser Arg Gln Leu Ser Gly Lys
                165                 170                 175

Ile Tyr Gln Ile Gln Gly Thr Gly Lys Ala Trp Asp Trp Glu Val Asp
            180                 185                 190

Ser Glu Asn Gly Asn Tyr Asp Tyr Leu Met Gly Ala Asp Ile Asp Tyr
        195                 200                 205

Asp His Pro Asp Val Gln Thr Glu Val Lys Asn Trp Gly Lys Trp Phe
    210                 215                 220

Val Asn Thr Leu Asn Leu Asp Gly Val Arg Leu Asp Ala Val Lys His
225                 230                 235                 240

Ile Lys Phe Asp Tyr Met Ser Ser Trp Leu Ser Ser Val Lys Ser Thr
                245                 250                 255

Thr Gly Lys Ser Asn Leu Phe Ala Val Gly Glu Tyr Trp Asn Thr Ser
            260                 265                 270

Leu Gly Ala Leu Glu Asn Tyr Glu Asn Lys Thr Asn Trp Ser Met Ser
        275                 280                 285

Leu Phe Asp Val Pro Leu His Met Asn Phe Gln Ala Ala Ala Asn Gly
    290                 295                 300

Gly Gly Tyr Tyr Asp Met Arg Asn Leu Leu Asn Asn Thr Met Met Lys
305                 310                 315                 320

Asn His Pro Ile Gln Ala Val Thr Phe Val Asp Asn His Asp Thr Glu
                325                 330                 335

Pro Gly Gln Ala Leu Gln Ser Trp Val Ser Asp Trp Phe Lys Pro Leu
            340                 345                 350

Ala Tyr Ala Thr Ile Leu Thr Arg Gln Glu Gly Tyr Pro Cys Val Phe
        355                 360                 365

Tyr Gly Asp Tyr Tyr Gly Ile Pro Ser Gln Ser Val Ser Ala Lys Ser
    370                 375                 380

Thr Trp Leu Asp Lys Gln Leu Ser Ala Arg Lys Ser Tyr Ala Tyr Gly
385                 390                 395                 400

Thr Gln His Asp Tyr Leu Asp Asn Gln Asp Val Ile Gly Trp Thr Arg
                405                 410                 415
```

```
Glu Gly Asp Ser Ala His Ala Gly Ser Gly Leu Ala Thr Val Met Ser
                420                 425                 430

Asp Gly Pro Gly Gly Ser Lys Thr Met Tyr Val Gly Thr Ala His Ala
            435                 440                 445

Gly Gln Val Phe Lys Asp Ile Thr Gly Asn Arg Thr Asp Thr Val Thr
        450                 455                 460

Ile Asn Ser Ala Gly Asn Gly Thr Phe Pro Cys Asn Gly Gly Ser Val
465                 470                 475                 480

Ser Ile Trp Val Lys Gln
                485

<210> SEQ ID NO 17
<211> LENGTH: 483
<212> TYPE: PRT
<213> ORGANISM: Bacillus amyloliquefaciens

<400> SEQUENCE: 17

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Val Thr Ser
        115                 120                 125

Glu Glu Tyr Gln Ile Lys Ala Trp Thr Asp Phe Arg Phe Pro Gly Arg
    130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
    210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Gly Tyr Asp Met
```

```
            290                 295                 300
Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Thr Ser Pro Lys Glu Ile Pro Ser Leu Lys Asp Asn Ile
    370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
    450                 455                 460

Asp Gly Trp Gly Glu Phe His Val Asn Asp Gly Ser Val Ser Ile Tyr
465                 470                 475                 480

Val Gln Lys

<210> SEQ ID NO 18
<211> LENGTH: 486
<212> TYPE: PRT
<213> ORGANISM: Clostridium sp

<400> SEQUENCE: 18

Met Asp Asn Gly Leu Met Phe Gln Gly Phe Glu Trp Tyr Met Pro Asp
1               5                   10                  15

Asp Gly Asn Tyr Tyr Lys Asp Leu Lys Lys Lys Leu Val Asp Met Lys
            20                  25                  30

Arg Ile Gly Val Thr Ser Val Trp Leu Pro Pro Val Cys Lys Ala Thr
        35                  40                  45

Gly Ser Asn Asp Thr Gly Tyr Gly Val Tyr Asp Leu Tyr Asp Leu Gly
    50                  55                  60

Glu Phe Asp Gln Lys Gly Ser Val Arg Thr Lys Tyr Gly Thr Lys Glu
65                  70                  75                  80

Glu Leu Leu Asp Leu Ile Lys Ala Ile His Asp Glu Gly Met Tyr Val
                85                  90                  95

Tyr Ala Asp Val Val Leu Asn His Lys Ala Gly Ala Asp Phe Glu Glu
            100                 105                 110

Glu Phe Met Ala Val Lys Val Asp Asn Asn Arg Thr Lys Glu Ile
        115                 120                 125

Glu Lys Gln Arg Asn Ile Lys Ala Trp Thr Gly Phe Asn Phe Pro Gly
    130                 135                 140

Arg Asn Gly Lys Tyr Ser Asp Phe Thr Trp Asn Tyr Asn His Phe Ser
145                 150                 155                 160

Gly Val Asp Tyr Asp Ala Ser Thr Gly Asp Lys Gly Ile Phe Arg Ile
                165                 170                 175

Ile Gly Glu Asn Lys Gly Trp Asn Trp Gly Val Ser His Asp Asn Gly
```

```
              180                 185                 190
Asn Phe Asp Tyr Leu Met Phe Ala Asp Ile Asp His Ala Asn Thr Glu
            195                 200                 205

Val Lys Glu Glu Leu Lys Arg Trp Val Asp Trp Phe Ile Glu Glu Leu
210                 215                 220

Asn Leu Asp Gly Ile Arg Phe Asp Ala Val Lys His Ile Asp Ser Ala
225                 230                 235                 240

Phe Leu Glu Glu Phe Thr Ser His Ile Lys Glu Lys Met Gly Asp Glu
                245                 250                 255

Phe Tyr Phe Leu Gly Glu Tyr Trp Asp His Asp Val Lys Asn Lys Ile
            260                 265                 270

Lys Phe Met Lys Ser Thr Lys Tyr Ser Met Asp Leu Phe Asp Val Gly
                275                 280                 285

Leu His Phe Asn Met Tyr Ala Ala Ser Gln Asn Ser Asn Tyr Asp
            290                 295                 300

Leu Arg Lys Leu Phe Asp Asn Thr Val Thr Lys Thr Asp Pro Ala Met
305                 310                 315                 320

Ser Val Thr Phe Val Asp Asn His Asp Ser Glu Pro Gly Gln Ser Leu
                325                 330                 335

Glu Ser Phe Val Lys Glu Trp Phe Lys Glu Ile Ala Tyr Gly Ile Ile
                340                 345                 350

Leu Leu Arg Lys Asp Gly Tyr Pro Cys Ile Phe Tyr Gly Asp Tyr Tyr
            355                 360                 365

Gly Ile Gly Gly Glu Phe Met Ile Lys Pro Leu Lys Glu Lys Ile Asp
        370                 375                 380

Val Leu Ser Leu Ile Arg Lys Asn His Ala Tyr Gly Ala Gln Asp Asp
385                 390                 395                 400

Tyr Phe Lys Glu Lys Asp Leu Ile Gly Trp Val Arg Gln Gly Thr Glu
                405                 410                 415

Asp His Pro Gly Lys Cys Ala Val Val Ile Ser Thr Arg Glu Lys Lys
                420                 425                 430

Thr Ile Ser Met Phe Ile Asp Lys Tyr His Ser Gly Lys Val Tyr Ala
            435                 440                 445

Asp Phe Thr Gly Asn Cys Ala Asp Lys Val Lys Val Asp Glu Glu Gly
            450                 455                 460

Tyr Gly Glu Phe Thr Ala Glu Ala Gly Ser Ile Ser Val Trp Leu Glu
465                 470                 475                 480

Glu Glu Ile Val Leu Gly
                485

<210> SEQ ID NO 19
<211> LENGTH: 413
<212> TYPE: PRT
<213> ORGANISM: Pyrococcus furiosus

<400> SEQUENCE: 19

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
        35                  40                  45

Ile Gly Trp Val Asp Phe Val Asn Gly Arg Ser Tyr Pro Tyr Asp Asp
    50                  55                  60
```

```
His Gly His Gly Thr His Val Ala Ser Ile Ala Ala Gly Thr Gly Ala
 65                  70                  75                  80

Ala Ser Asn Gly Lys Tyr Lys Gly Met Ala Pro Gly Ala Lys Leu Ala
                 85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350

Tyr Asp Pro Asn Gly Asn Gln Val Asp Tyr Ser Tyr Thr Ala Tyr Tyr
        355                 360                 365

Asp Phe Glu Lys Val Gly Tyr Tyr Asn Pro Thr Asp Gly Thr Trp Thr
370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser Pro
                405                 410

<210> SEQ ID NO 20
<211> LENGTH: 177
<212> TYPE: PRT
<213> ORGANISM: Thermoascus aurantiacus

<400> SEQUENCE: 20

Thr Arg Ile Ser Ser Cys Ser Gly Ser Arg Gln Ser Ala Leu Thr Thr
1               5                   10                  15

Ala Leu Arg Asn Ala Ala Ser Leu Ala Asn Ala Ala Ala Asp Ala Ala
            20                  25                  30
```

```
Gln Ser Gly Ser Ala Ser Lys Phe Ser Glu Tyr Phe Lys Thr Thr Ser
         35                  40                  45

Ser Ser Thr Arg Gln Thr Val Ala Ala Arg Leu Arg Ala Val Ala Arg
 50                  55                  60

Glu Ala Ser Ser Ser Ser Gly Ala Thr Thr Tyr Tyr Cys Asp Asp
 65                  70                  75                  80

Pro Tyr Gly Tyr Cys Ser Ser Asn Val Leu Ala Tyr Thr Leu Pro Ser
                 85                  90                  95

Tyr Asn Ile Ile Ala Asn Cys Asp Ile Phe Tyr Thr Tyr Leu Pro Ala
                100                 105                 110

Leu Thr Ser Thr Cys His Ala Gln Asp Gln Ala Thr Thr Ala Leu His
             115                 120                 125

Glu Phe Thr His Ala Pro Gly Val Tyr Ser Pro Gly Thr Asp Asp Leu
130                 135                 140

Ala Tyr Gly Tyr Gln Ala Ala Met Gly Leu Ser Ser Ser Gln Ala Val
145                 150                 155                 160

Met Asn Ala Asp Thr Tyr Ala Leu Tyr Ala Asn Ala Ile Tyr Leu Gly
                165                 170                 175

Cys

<210> SEQ ID NO 21
<211> LENGTH: 595
<212> TYPE: PRT
<213> ORGANISM: Penicillium oxalicum

<400> SEQUENCE: 21

Arg Pro Asp Pro Lys Gly Gly Asn Leu Thr Pro Phe Ile His Lys Glu
 1               5                  10                  15

Gly Glu Arg Ser Leu Gln Gly Ile Leu Asp Asn Leu Gly Gly Arg Gly
             20                  25                  30

Lys Lys Thr Pro Gly Thr Ala Ala Gly Leu Phe Ile Ala Ser Pro Asn
         35                  40                  45

Thr Glu Asn Pro Asn Tyr Tyr Tyr Thr Trp Thr Arg Asp Ser Ala Leu
 50                  55                  60

Thr Ala Lys Cys Leu Ile Asp Leu Phe Glu Asp Ser Arg Ala Lys Phe
 65                  70                  75                  80

Pro Ile Asp Arg Lys Tyr Leu Glu Thr Gly Ile Arg Asp Tyr Lys Ser
                 85                  90                  95

Ser Gln Ala Ile Leu Gln Ser Val Ser Asn Pro Ser Gly Thr Leu Lys
                100                 105                 110

Asp Gly Ser Gly Leu Gly Glu Pro Lys Phe Glu Ile Asp Leu Asn Pro
             115                 120                 125

Phe Ser Gly Ala Trp Gly Arg Pro Gln Arg Asp Gly Pro Ala Leu Arg
130                 135                 140

Ala Thr Ala Met Ile Thr Tyr Ala Asn Tyr Leu Ile Ser His Gly Gln
145                 150                 155                 160

Lys Ser Asp Val Ser Gln Val Met Trp Pro Ile Ile Ala Asn Asp Leu
                165                 170                 175

Ala Tyr Val Gly Gln Tyr Trp Asn Asn Thr Gly Phe Asp Leu Trp Glu
                180                 185                 190

Glu Val Asp Gly Ser Ser Phe Phe Thr Ile Ala Val Gln His Arg Ala
             195                 200                 205

Leu Val Glu Gly Ser Gln Leu Ala Lys Lys Leu Gly Lys Ser Cys Asp
210                 215                 220
```

```
Ala Cys Asp Ser Gln Pro Gln Ile Leu Cys Phe Leu Gln Ser Phe
225                 230                 235                 240

Trp Asn Gly Lys Tyr Ile Thr Ser Asn Ile Asn Thr Gln Ala Ser Arg
                245                 250                 255

Ser Gly Ile Asp Leu Asp Ser Val Leu Gly Ser Ile His Thr Phe Asp
                260                 265                 270

Pro Glu Ala Ala Cys Asp Asp Ala Thr Phe Gln Pro Cys Ser Ala Arg
                275                 280                 285

Ala Leu Ala Asn His Lys Val Tyr Val Asp Ser Phe Arg Ser Ile Tyr
                290                 295                 300

Lys Ile Asn Ala Gly Leu Ala Glu Gly Ser Ala Ala Asn Val Gly Arg
305                 310                 315                 320

Tyr Pro Glu Asp Val Tyr Gln Gly Gly Asn Pro Trp Tyr Leu Ala Thr
                325                 330                 335

Leu Gly Ala Ser Glu Leu Leu Tyr Asp Ala Leu Tyr Gln Trp Asp Arg
                340                 345                 350

Leu Gly Lys Leu Glu Val Ser Glu Thr Ser Leu Ser Phe Phe Lys Asp
                355                 360                 365

Phe Asp Ala Thr Val Lys Ile Gly Ser Tyr Ser Arg Asn Ser Lys Thr
370                 375                 380

Tyr Lys Lys Leu Thr Gln Ser Ile Lys Ser Tyr Ala Asp Gly Phe Ile
385                 390                 395                 400

Gln Leu Val Gln Gln Tyr Thr Pro Ser Asn Gly Ser Leu Ala Glu Gln
                405                 410                 415

Tyr Asp Arg Asn Thr Ala Ala Pro Leu Ser Ala Asn Asp Leu Thr Trp
                420                 425                 430

Ser Phe Ala Ser Phe Leu Thr Ala Thr Gln Arg Arg Asp Ala Val Val
                435                 440                 445

Pro Pro Ser Trp Gly Ala Lys Ser Ala Asn Lys Val Pro Thr Thr Cys
450                 455                 460

Ser Ala Ser Pro Val Val Gly Thr Tyr Lys Ala Pro Thr Ala Thr Phe
465                 470                 475                 480

Ser Ser Lys Thr Lys Cys Val Pro Ala Lys Asp Ile Val Pro Ile Thr
                485                 490                 495

Phe Tyr Leu Ile Glu Asn Thr Tyr Tyr Gly Glu Asn Val Phe Met Ser
                500                 505                 510

Gly Asn Ile Thr Ala Leu Gly Asn Trp Asp Ala Lys Lys Gly Phe Pro
                515                 520                 525

Leu Thr Ala Asn Leu Tyr Thr Gln Asp Gln Asn Leu Trp Phe Ala Ser
                530                 535                 540

Val Glu Phe Ile Pro Ala Gly Thr Pro Phe Glu Tyr Lys Tyr Tyr Lys
545                 550                 555                 560

Val Glu Pro Asn Gly Asp Ile Thr Trp Glu Lys Gly Pro Asn Arg Val
                565                 570                 575

Phe Val Ala Pro Thr Gly Cys Pro Val Gln Pro His Ser Asn Asp Val
                580                 585                 590

Trp Gln Phe
        595

<210> SEQ ID NO 22
<211> LENGTH: 598
<212> TYPE: PRT
<213> ORGANISM: Talaromyces emersonii
```

```
<400> SEQUENCE: 22

Arg Ala Pro Val Ala Arg Ala Thr Gly Ser Leu Asp Ser Phe Leu
1               5                   10                  15

Ala Thr Glu Thr Pro Ile Ala Leu Gln Gly Val Leu Asn Asn Ile Gly
            20                  25                  30

Pro Asn Gly Ala Asp Val Ala Gly Ser Ala Gly Ile Val Val Ala
        35                  40                  45

Ser Pro Ser Arg Ser Asp Pro Asn Tyr Phe Tyr Ser Trp Thr Arg Asp
50                  55                  60

Ala Ala Leu Thr Ala Lys Tyr Leu Val Asp Ala Phe Ile Ala Gly Asn
65                  70                  75                  80

Lys Asp Leu Glu Gln Thr Ile Gln Gln Tyr Ile Ser Ala Gln Ala Lys
                85                  90                  95

Val Gln Thr Ile Ser Asn Pro Ser Gly Asp Leu Ser Thr Gly Gly Leu
            100                 105                 110

Gly Glu Pro Lys Phe Asn Val Asn Glu Thr Ala Phe Thr Gly Pro Trp
        115                 120                 125

Gly Arg Pro Gln Arg Asp Gly Pro Ala Leu Arg Ala Thr Ala Leu Ile
130                 135                 140

Ala Tyr Ala Asn Tyr Leu Ile Asp Asn Gly Glu Ala Ser Thr Ala Asp
145                 150                 155                 160

Glu Ile Ile Trp Pro Ile Val Gln Asn Asp Leu Ser Tyr Ile Thr Gln
                165                 170                 175

Tyr Trp Asn Ser Ser Thr Phe Asp Leu Trp Glu Glu Val Glu Gly Ser
            180                 185                 190

Ser Phe Phe Thr Thr Ala Val Gln His Arg Ala Leu Val Glu Gly Asn
        195                 200                 205

Ala Leu Ala Thr Arg Leu Asn His Thr Cys Ser Asn Cys Val Ser Gln
210                 215                 220

Ala Pro Gln Val Leu Cys Phe Leu Gln Ser Tyr Trp Thr Gly Ser Tyr
225                 230                 235                 240

Val Leu Ala Asn Phe Gly Gly Ser Gly Arg Ser Gly Lys Asp Val Asn
                245                 250                 255

Ser Ile Leu Gly Ser Ile His Thr Phe Asp Pro Ala Gly Gly Cys Asp
            260                 265                 270

Asp Ser Thr Phe Gln Pro Cys Ser Ala Arg Ala Leu Ala Asn His Lys
        275                 280                 285

Val Val Thr Asp Ser Phe Arg Ser Ile Tyr Ala Ile Asn Ser Gly Ile
290                 295                 300

Ala Glu Gly Ser Ala Val Ala Val Gly Arg Tyr Pro Glu Asp Val Tyr
305                 310                 315                 320

Gln Gly Gly Asn Pro Trp Tyr Leu Ala Thr Ala Ala Ala Glu Gln
                325                 330                 335

Leu Tyr Asp Ala Ile Tyr Gln Trp Lys Lys Ile Gly Ser Ile Ser Ile
            340                 345                 350

Thr Asp Val Ser Leu Pro Phe Phe Gln Asp Ile Tyr Pro Ser Ala Ala
        355                 360                 365

Val Gly Thr Tyr Asn Ser Gly Ser Thr Thr Phe Asn Asp Ile Ile Ser
370                 375                 380

Ala Val Gln Thr Tyr Gly Asp Gly Tyr Leu Ser Ile Val Glu Lys Tyr
385                 390                 395                 400

Thr Pro Ser Asp Gly Ser Leu Thr Glu Gln Phe Ser Arg Thr Asp Gly
                405                 410                 415
```

```
Thr Pro Leu Ser Ala Ser Ala Leu Thr Trp Ser Tyr Ala Ser Leu Leu
                420                 425                 430

Thr Ala Ser Ala Arg Arg Gln Ser Val Val Pro Ala Ser Trp Gly Glu
            435                 440                 445

Ser Ser Ala Ser Ser Val Pro Ala Val Cys Ser Ala Thr Ser Ala Thr
450                 455                 460

Gly Pro Tyr Ser Thr Ala Thr Asn Thr Val Trp Pro Ser Ser Gly Ser
465                 470                 475                 480

Gly Ser Ser Thr Thr Thr Ser Ser Ala Pro Cys Thr Thr Pro Thr Ser
                485                 490                 495

Val Ala Val Thr Phe Asp Glu Ile Val Ser Thr Ser Tyr Gly Glu Thr
                500                 505                 510

Ile Tyr Leu Ala Gly Ser Ile Pro Glu Leu Gly Asn Trp Ser Thr Ala
            515                 520                 525

Ser Ala Ile Pro Leu Arg Ala Asp Ala Tyr Thr Asn Ser Asn Pro Leu
530                 535                 540

Trp Tyr Val Thr Val Asn Leu Pro Pro Gly Thr Ser Phe Glu Tyr Lys
545                 550                 555                 560

Phe Phe Lys Asn Gln Thr Asp Gly Thr Ile Val Trp Glu Asp Asp Pro
                565                 570                 575

Asn Arg Ser Tyr Thr Val Pro Ala Tyr Cys Gly Gln Thr Thr Ala Ile
                580                 585                 590

Leu Asp Asp Ser Trp Gln
                595

<210> SEQ ID NO 23
<211> LENGTH: 555
<212> TYPE: PRT
<213> ORGANISM: Pycnoporus sanguinea

<400> SEQUENCE: 23

Gln Ser Ser Ala Val Asp Ala Tyr Val Ala Ser Glu Ser Pro Ile Ala
1               5                   10                  15

Lys Gln Gly Val Leu Asn Asn Ile Gly Pro Asn Gly Ser Lys Ala His
                20                  25                  30

Gly Ala Lys Ala Gly Ile Val Val Ala Ser Pro Ser Thr Glu Asn Pro
            35                  40                  45

Asp Tyr Leu Tyr Thr Trp Thr Arg Asp Ser Ser Leu Val Phe Lys Leu
50                  55                  60

Leu Ile Asp Gln Phe Thr Ser Gly Asp Thr Ser Leu Arg Gly Leu
65                  70                  75                  80

Ile Asp Asp Phe Thr Ser Ala Glu Ala Ile Leu Gln Gln Val Ser Asn
                85                  90                  95

Pro Ser Gly Thr Val Ser Thr Gly Gly Leu Gly Glu Pro Lys Phe Asn
                100                 105                 110

Ile Asp Glu Thr Ala Phe Thr Gly Ala Trp Gly Arg Pro Gln Arg Asp
            115                 120                 125

Gly Pro Ala Leu Arg Ala Thr Ser Ile Ile Arg Tyr Ala Asn Trp Leu
130                 135                 140

Leu Asp Asn Gly Asn Thr Thr Tyr Val Ser Asn Thr Leu Trp Pro Val
145                 150                 155                 160

Ile Gln Leu Asp Leu Asp Tyr Val Ala Asp Asn Trp Asn Gln Ser Thr
                165                 170                 175

Phe Asp Leu Trp Glu Glu Val Asp Ser Ser Ser Phe Phe Thr Thr Ala
```

```
            180                 185                 190
Val Gln His Arg Ala Leu Arg Glu Gly Ala Thr Phe Ala Ser Arg Ile
            195                 200                 205
Gly Gln Ser Ser Val Val Ser Gly Tyr Thr Thr Gln Ala Asp Asn Leu
            210                 215                 220
Leu Cys Phe Leu Gln Ser Tyr Trp Asn Pro Ser Gly Gly Tyr Val Thr
225                 230                 235                 240
Ala Asn Thr Gly Gly Arg Ser Gly Lys Asp Ser Asn Thr Val Leu
                245                 250                 255
Thr Ser Ile His Thr Phe Asp Pro Ala Ala Gly Cys Asp Ala Ala Thr
            260                 265                 270
Phe Gln Pro Cys Ser Asp Lys Ala Leu Ser Asn Leu Lys Val Tyr Val
            275                 280                 285
Asp Ala Phe Arg Ser Ile Tyr Thr Ile Asn Asn Gly Ile Ala Ser Asn
            290                 295                 300
Ala Ala Val Ala Thr Gly Arg Tyr Pro Glu Asp Ser Tyr Met Gly Gly
305                 310                 315                 320
Asn Pro Trp Tyr Leu Thr Thr Ser Ala Val Ala Glu Gln Leu Tyr Asp
                325                 330                 335
Ala Leu Tyr Val Trp Asp Gln Leu Gly Gly Leu Asn Val Thr Ser Thr
            340                 345                 350
Ser Leu Ala Phe Phe Gln Gln Phe Ala Ser Gly Leu Ser Thr Gly Thr
            355                 360                 365
Tyr Ser Ala Ser Ser Ser Thr Tyr Ala Thr Leu Thr Ser Ala Ile Arg
            370                 375                 380
Ser Phe Ala Asp Gly Phe Leu Ala Ile Asn Ala Lys Tyr Thr Pro Ala
385                 390                 395                 400
Asp Gly Gly Leu Ala Glu Gln Tyr Ser Arg Asn Asp Gly Thr Pro Leu
                405                 410                 415
Ser Ala Val Asp Leu Thr Trp Ser Tyr Ala Ala Ala Leu Thr Ala Phe
            420                 425                 430
Ala Ala Arg Glu Gly Lys Thr Tyr Gly Ser Trp Gly Ala Ala Gly Leu
            435                 440                 445
Thr Val Pro Ala Ser Cys Ser Gly Gly Gly Ala Thr Val Ala Val
            450                 455                 460
Thr Phe Asn Val Gln Ala Thr Val Phe Gly Glu Asn Ile Tyr Ile
465                 470                 475                 480
Thr Gly Ser Val Ala Ala Leu Gln Asn Trp Ser Pro Asp Asn Ala Leu
                485                 490                 495
Ile Leu Ser Ala Ala Asn Tyr Pro Thr Trp Ser Ile Thr Val Asn Leu
            500                 505                 510
Pro Ala Asn Thr Val Val Gln Tyr Lys Tyr Ile Arg Lys Phe Asn Gly
            515                 520                 525
Gln Val Thr Trp Glu Ser Asp Pro Asn Asn Gln Ile Thr Thr Pro Ser
            530                 535                 540
Gly Gly Ser Phe Thr Gln Asn Asp Val Trp Arg
545                 550                 555

<210> SEQ ID NO 24
<211> LENGTH: 556
<212> TYPE: PRT
<213> ORGANISM: Gloeophyllum sepiarium

<400> SEQUENCE: 24
```

```
Gln Ser Val Asp Ser Tyr Val Ser Glu Gly Pro Ile Ala Lys Ala
  1               5                  10                  15

Gly Val Leu Ala Asn Ile Gly Pro Asn Gly Ser Lys Ala Ser Gly Ala
             20                  25                  30

Ser Ala Gly Val Val Ala Ser Pro Ser Thr Ser Asp Pro Asp Tyr
             35                  40                  45

Trp Tyr Thr Trp Thr Arg Asp Ser Ser Leu Val Phe Lys Ser Leu Ile
 50                  55                  60

Asp Gln Tyr Thr Thr Gly Ile Asp Ser Thr Ser Ser Leu Arg Thr Leu
 65                  70                  75                  80

Ile Asp Asp Phe Val Thr Ala Glu Ala Asn Leu Gln Gln Val Ser Asn
                 85                  90                  95

Pro Ser Gly Thr Leu Thr Thr Gly Gly Leu Gly Glu Pro Lys Phe Asn
                100                 105                 110

Val Asp Glu Thr Ala Phe Thr Gly Ala Trp Gly Arg Pro Gln Arg Asp
            115                 120                 125

Gly Pro Ala Leu Arg Ser Thr Ala Leu Ile Thr Tyr Gly Asn Trp Leu
        130                 135                 140

Leu Ser Asn Gly Asn Thr Ser Tyr Val Thr Ser Asn Leu Trp Pro Ile
145                 150                 155                 160

Ile Gln Asn Asp Leu Gly Tyr Val Val Ser Tyr Trp Asn Gln Ser Thr
                165                 170                 175

Tyr Asp Leu Trp Glu Glu Val Asp Ser Ser Phe Phe Thr Thr Ala
            180                 185                 190

Val Gln His Arg Ala Leu Arg Glu Gly Ala Ala Phe Ala Thr Ala Ile
        195                 200                 205

Gly Gln Thr Ser Gln Val Ser Ser Tyr Thr Thr Gln Ala Asp Asn Leu
        210                 215                 220

Leu Cys Phe Leu Gln Ser Tyr Trp Asn Pro Ser Gly Gly Tyr Ile Thr
225                 230                 235                 240

Ala Asn Thr Gly Gly Gly Arg Ser Gly Lys Asp Ala Asn Thr Leu Leu
                245                 250                 255

Ala Ser Ile His Thr Tyr Asp Pro Ser Ala Gly Cys Asp Ala Ala Thr
            260                 265                 270

Phe Gln Pro Cys Ser Asp Lys Ala Leu Ser Asn Leu Lys Val Tyr Val
        275                 280                 285

Asp Ser Phe Arg Ser Val Tyr Ser Ile Asn Ser Gly Val Ala Ser Asn
        290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Glu Ser Gln Gly Ser Leu Glu Val Thr Ser Thr
            340                 345                 350

Ser Leu Ala Phe Phe Gln Gln Phe Ser Ser Gly Val Thr Ala Gly Thr
        355                 360                 365

Tyr Ser Ser Ser Ser Ser Thr Tyr Ser Thr Leu Thr Ser Ala Ile Lys
        370                 375                 380

Asn Phe Ala Asp Gly Phe Val Ala Ile Asn Ala Lys Tyr Thr Pro Ser
385                 390                 395                 400

Asn Gly Gly Leu Ala Glu Gln Tyr Ser Lys Ser Asp Gly Ser Pro Leu
                405                 410                 415

Ser Ala Val Asp Leu Thr Trp Ser Tyr Ala Ser Ala Leu Thr Ala Phe
```

```
              420                 425                 430
Glu Ala Arg Asn Asn Thr Gln Phe Ala Gly Trp Gly Ala Ala Gly Leu
            435                 440                 445

Thr Val Pro Ser Ser Cys Ser Gly Asn Ser Gly Pro Thr Val Ala
        450                 455                 460

Val Thr Phe Asn Val Asn Ala Glu Thr Val Trp Gly Glu Asn Ile Tyr
465                 470                 475                 480

Leu Thr Gly Ser Val Asp Ala Leu Glu Asn Trp Ser Ala Asp Asn Ala
                485                 490                 495

Leu Leu Leu Ser Ser Ala Asn Tyr Pro Thr Trp Ser Ile Thr Val Asn
            500                 505                 510

Leu Pro Ala Ser Thr Ala Ile Glu Tyr Lys Tyr Ile Arg Lys Asn Asn
        515                 520                 525

Gly Ala Val Thr Trp Glu Ser Asp Pro Asn Asn Ser Ile Thr Thr Pro
    530                 535                 540

Ala Ser Gly Ser Thr Thr Glu Asn Asp Thr Trp Arg
545                 550                 555

<210> SEQ ID NO 25
<211> LENGTH: 559
<212> TYPE: PRT
<213> ORGANISM: Gloeophyllum trabeum

<400> SEQUENCE: 25

Gln Ser Val Asp Ser Tyr Val Gly Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ala Ala Gly Val Val Val Ala Ser Pro Ser Lys Ser Asp Pro Asp Tyr
        35                  40                  45

Trp Tyr Thr Trp Thr Arg Asp Ser Ser Leu Val Phe Lys Ser Leu Ile
    50                  55                  60

Asp Gln Tyr Thr Thr Gly Ile Asp Ser Thr Ser Ser Leu Arg Ser Leu
65                  70                  75                  80

Ile Asp Ser Phe Val Ile Ala Glu Ala Asn Ile Gln Gln Val Ser Asn
                85                  90                  95

Pro Ser Gly Thr Leu Thr Thr Gly Gly Leu Gly Glu Pro Lys Phe Asn
            100                 105                 110

Val Asp Glu Thr Ala Phe Thr Gly Ala Trp Gly Arg Pro Gln Arg Asp
        115                 120                 125

Gly Pro Ala Leu Arg Ala Thr Ala Leu Ile Thr Tyr Gly Asn Trp Leu
    130                 135                 140

Leu Ser Asn Gly Asn Thr Thr Trp Val Thr Ser Thr Leu Trp Pro Ile
145                 150                 155                 160

Ile Gln Asn Asp Leu Asn Tyr Val Val Gln Tyr Trp Asn Gln Thr Thr
                165                 170                 175

Phe Asp Leu Trp Glu Glu Val Asn Ser Ser Phe Phe Thr Thr Ala
            180                 185                 190

Val Gln His Arg Ala Leu Arg Glu Gly Ala Ala Phe Ala Thr Lys Ile
        195                 200                 205

Gly Gln Thr Ser Ser Val Ser Ser Tyr Thr Thr Gln Ala Ala Asn Leu
    210                 215                 220

Leu Cys Phe Leu Gln Ser Tyr Trp Asn Pro Thr Ser Gly Tyr Ile Thr
225                 230                 235                 240
```

Ala Asn Thr Gly Gly Gly Arg Ser Gly Lys Asp Ala Asn Thr Leu Leu
                245                 250                 255

Ala Ser Ile His Thr Tyr Asp Pro Ser Ala Gly Cys Asp Ala Thr Thr
            260                 265                 270

Phe Gln Pro Cys Ser Asp Lys Ala Leu Ser Asn Leu Lys Val Tyr Val
        275                 280                 285

Asp Ser Phe Arg Ser Val Tyr Ser Ile Asn Ser Gly Ile Ala Ser Asn
    290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Ala Ala Gln Gly Ser Leu Asn Val Thr Ser Ile
            340                 345                 350

Ser Leu Pro Phe Phe Gln Gln Phe Ser Ser Val Thr Ala Gly Thr
        355                 360                 365

Tyr Ala Ser Ser Thr Thr Tyr Thr Thr Leu Thr Ser Ala Ile Lys
    370                 375                 380

Ser Phe Ala Asp Gly Phe Val Ala Ile Asn Ala Gln Tyr Thr Pro Ser
385                 390                 395                 400

Asn Gly Gly Leu Ala Glu Gln Phe Ser Arg Ser Asn Gly Ala Pro Val
                405                 410                 415

Ser Ala Val Asp Leu Thr Trp Ser Tyr Ala Ser Ala Leu Thr Ala Phe
            420                 425                 430

Glu Ala Arg Asn Asn Thr Gln Phe Ala Gly Trp Gly Ala Val Gly Leu
        435                 440                 445

Thr Val Pro Thr Ser Cys Ser Ser Asn Ser Gly Gly Gly Gly Ser
    450                 455                 460

Thr Val Ala Val Thr Phe Asn Val Asn Ala Gln Thr Val Trp Gly Glu
465                 470                 475                 480

Asn Ile Tyr Ile Thr Gly Ser Val Asp Ala Leu Ser Asn Trp Ser Pro
                485                 490                 495

Asp Asn Ala Leu Leu Leu Ser Ser Ala Asn Tyr Pro Thr Trp Ser Ile
            500                 505                 510

Thr Val Asn Leu Pro Ala Ser Thr Ala Ile Gln Tyr Lys Tyr Ile Arg
        515                 520                 525

Lys Asn Asn Gly Ala Val Thr Trp Glu Ser Asp Pro Asn Asn Ser Ile
    530                 535                 540

Thr Thr Pro Ala Ser Gly Ser Val Thr Glu Asn Asp Thr Trp Arg
545                 550                 555

<210> SEQ ID NO 26
<211> LENGTH: 583
<212> TYPE: PRT
<213> ORGANISM: Artificial
<220> FEATURE:
<223> OTHER INFORMATION: Rhizomucor pusilus alpha-amylase core having a
      linker and starch binding domain from A. niger glucoamylase

<400> SEQUENCE: 26

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

-continued

Tyr Ile Ser Gly Met Gly Phe Asp Ala Ile Trp Ile Ser Pro Ile Pro
                50                  55                  60
Lys Asn Ser Asp Gly Gly Tyr His Gly Tyr Trp Ala Thr Asp Phe Tyr
 65                  70                  75                  80
Gln Leu Asn Ser Asn Phe Gly Asp Glu Ser Gln Leu Lys Ala Leu Ile
                    85                  90                  95
Gln Ala Ala His Glu Arg Asp Met Tyr Val Met Leu Asp Val Val Ala
                100                 105                 110
Asn His Ala Gly Pro Thr Ser Asn Gly Tyr Ser Gly Tyr Thr Phe Gly
            115                 120                 125
Asp Ala Ser Leu Tyr His Pro Lys Cys Thr Ile Asp Tyr Asn Asp Gln
130                 135                 140
Thr Ser Ile Glu Gln Cys Trp Val Ala Asp Glu Leu Pro Asp Ile Asp
145                 150                 155                 160
Thr Glu Asn Ser Asp Asn Val Ala Ile Leu Asn Asp Ile Val Ser Gly
                165                 170                 175
Trp Val Gly Asn Tyr Ser Phe Asp Gly Ile Arg Ile Asp Thr Val Lys
                180                 185                 190
His Ile Arg Lys Asp Phe Trp Thr Gly Tyr Ala Glu Ala Ala Gly Val
            195                 200                 205
Phe Ala Thr Gly Glu Val Phe Asn Gly Asp Pro Ala Tyr Val Gly Pro
210                 215                 220
Tyr Gln Lys Tyr Leu Pro Ser Leu Ile Asn Tyr Pro Met Tyr Tyr Ala
225                 230                 235                 240
Leu Asn Asp Val Phe Val Ser Lys Ser Lys Gly Phe Ser Arg Ile Ser
                245                 250                 255
Glu Met Leu Gly Ser Asn Arg Asn Ala Phe Glu Asp Thr Ser Val Leu
            260                 265                 270
Thr Thr Phe Val Asp Asn His Asp Asn Pro Arg Phe Leu Asn Ser Gln
            275                 280                 285
Ser Asp Lys Ala Leu Phe Lys Asn Ala Leu Thr Tyr Val Leu Leu Gly
290                 295                 300
Glu Gly Ile Pro Ile Val Tyr Tyr Gly Ser Glu Gln Gly Phe Ser Gly
305                 310                 315                 320
Gly Ala Asp Pro Ala Asn Arg Glu Val Leu Trp Thr Thr Asn Tyr Asp
                325                 330                 335
Thr Ser Ser Asp Leu Tyr Gln Phe Ile Lys Thr Val Asn Ser Val Arg
            340                 345                 350
Met Lys Ser Asn Lys Ala Val Tyr Met Asp Ile Tyr Val Gly Asp Asn
            355                 360                 365
Ala Tyr Ala Phe Lys His Gly Asp Ala Leu Val Val Leu Asn Asn Tyr
370                 375                 380
Gly Ser Gly Ser Thr Asn Gln Val Ser Phe Ser Val Ser Gly Lys Phe
385                 390                 395                 400
Asp Ser Gly Ala Ser Leu Met Asp Ile Val Ser Asn Ile Thr Thr Thr
                405                 410                 415
Val Ser Ser Asp Gly Thr Val Thr Phe Asn Leu Lys Asp Gly Leu Pro
            420                 425                 430
Ala Ile Phe Thr Ser Ala Thr Gly Gly Thr Thr Thr Ala Thr Pro
            435                 440                 445
Thr Gly Ser Gly Ser Val Thr Ser Thr Ser Lys Thr Thr Ala Thr Ala
450                 455                 460

-continued

```
Ser Lys Thr Ser Thr Ser Thr Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
                500                 505                 510

Ser Asp Gly Ile Ala Leu Ser Ala Asp Lys Tyr Thr Ser Ser Asp Pro
                515                 520                 525

Leu Trp Tyr Val Thr Val Thr Leu Pro Ala Gly Glu Ser Phe Glu Tyr
                530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
                580

<210> SEQ ID NO 27
<211> LENGTH: 484
<212> TYPE: PRT
<213> ORGANISM: Bacillus stearothermophilus

<400> SEQUENCE: 27

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
                35                  40                  45

Gly Thr Ser Arg Ser Asp Val Gly Tyr Gly Val Tyr Asp Leu Tyr Asp
                50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
                100                 105                 110

Thr Glu Trp Val Asp Ala Val Glu Val Asn Pro Ser Asp Arg Asn Gln
                115                 120                 125

Glu Ile Ser Gly Thr Tyr Gln Ile Gln Ala Trp Thr Lys Phe Asp Phe
                130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
                180                 185                 190

Asn Gly Asn Tyr Asp Tyr Leu Met Tyr Ala Asp Leu Asp Met Asp His
                195                 200                 205

Pro Glu Val Val Thr Glu Leu Lys Asn Trp Gly Lys Trp Tyr Val Asn
                210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255
```

```
Lys Pro Leu Phe Thr Val Gly Glu Tyr Trp Ser Tyr Asp Ile Asn Lys
            260                 265                 270

Leu His Asn Tyr Ile Thr Lys Thr Asp Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys
```

US 11,326,153 B2

ALPHA-AMYLASE VARIANTS AND POLYNUCLEOTIDES ENCODING SAME

CROSS-REFERENCE TO RELATED APPLICATIONS

This application is a 35 U.S.C. 371 national application of international application no. PCT/US2018/064413 filed Dec. 7, 2018, which claims priority or the benefit under 35 U.S.C. 119 of Indian application nos. 201741044156 and 201841031044 filed Dec. 8, 2017 and Aug. 20, 2018, respectively, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to alpha-amylase variants, polynucleotides encoding the variants, methods of producing the variants, and methods of using the variants.

Description of the Related Art

Alpha-amylases (alpha-1,4-glucan-4-glucanohydrolases, E.C. 3.2.1.1) constitute a group of enzymes, which catalyze hydrolysis of starch and other linear and branched 1,4-glucosidic oligo- and polysaccharides.

Alpha-amylases are used commercially for a variety of purposes such as in the initial stages of starch processing (e.g., liquefaction); in wet milling processes; and in alcohol production from carbohydrate sources. They are also used as cleaning agents or adjuncts in detergent matrices; in the textile industry for starch desizing; in baking applications; in the beverage industry; in oil fields in drilling processes; in recycling processes, e.g., for de-inking paper; and in animal feed.

Fermentation products, such as ethanol, are typically produced by first grinding starch-containing material in a dry-grind or wet-milling process, then degrading the material into fermentable sugars using enzymes and finally converting the sugars directly or indirectly into the desired fermentation product using a fermenting organism. Liquid fermentation products are recovered from the fermented mash (often referred to as "beer mash"), e.g., by distillation, which separate the desired fermentation product from other liquids and/or solids.

For an alpha-amylase to be used in a starch liquefaction process it is of particular interest that it is thermostable and able to function at low pH and low calcium concentrations. Altered $Ca^{2+}$ stability means the stability of the enzyme under $Ca^{2+}$ depletion has been improved, i.e., higher or lower stability. In the context of the present invention, mutations (including amino acid substitutions) of importance are mutations achieving altered $Ca^{2+}$ stability, in particular improved $Ca^{2+}$ stability, i.e., higher stability, at especially low pH (i.e., pH 4-6). For use in detergents increased chelator stability is also desirable.

The DE target after liquefaction in starch processing for food application is set to achieve a starch negative liquefact but also perform the most efficient in saccharification when using a glucoamylase. So the average length of the dextrins (DE) created in liquefaction is very important to target for the most efficient DX generation in saccharification. Preferably a DE number in the range from 10-16 is desirable.

WO2000/060059 disclose Termamyl like alpha-amylase variants having increased stability at low $Ca^{2+}$ levels. WO2013/057143 and WO2013/057141 disclose variants of alpha-amylases from Bacillus liquefaciens having improved properties such as increased stability at low calcium concentrations.

An alpha-amylase from Bacillus stearothermophilus is disclosed in WO 99/19467 as SEQ ID NO: 3, and variants thereof have been disclosed in WO1996/023873, and WO1999/019467. Further variants of the Bacillus stearothermophilus alpha-amylase are disclosed in WO 2011/082425.

WO 2012/088303 (Novozymes) discloses processes for producing fermentation products by liquefying starch-containing material at a pH in the range from 4.5-5.0 at a temperature in the range from 80-90° C. using a combination of alpha-amylase having a T ½ (min) at pH 4.5, 85° C., 0.12 mM CaCl2) of at least 10 and a protease having a thermostability value of more than 20% determined as Relative Activity at 80° C./70° C.; followed by saccharification and fermentation.

WO 2013/082486 (Novozymes) discloses processes for producing fermentation products by liquefying starch-containing material at a pH in the range between from above 5.0-7.0 at a temperature above the initial gelatinization temperature using an alpha-amylase variant.

U.S. Pat. No. 8,084,240 discloses the E188P substitution in a Bacillus stearothermophilus alpha-amylase resulting in increased stability.

WO2009/061381 describes substitutions at position 242 resulting in improved performance when S is substituted with A, Q, E, D, or M whereas other substitutions resulted in less activity compared to wild type.

The present invention provides alpha-amylase variants with improved properties compared to its parent.

SUMMARY OF THE INVENTION

According to the present invention it has surprisingly been found that substitutions at a position corresponding to positions 242, 279, or 275 (using SEQ ID NO: 1 for numbering), which alone will result in decreased performance, will result in a synergistic improvement in combination with an E188P substitution.

In a first aspect the present invention relates to an alpha-amylase variant comprising a substitution at a position corresponding to position 188 and at least one further substitution at a position corresponding to position 242 or 279 or 275 of SEQ ID NO: 1, in particular one or more combinations of substitutions selected from the group consisting of the group consisting of E188P+S242Y, E188P+S242F, E188P+S242H, E188P+S242W, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, wherein the variant has at least 60%, at least 65%, at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of: SEQ ID NO: 1, SEQ ID NO: 2, SEQ ID NO: 3, SEQ ID NO:

4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

The present invention also relates to polynucleotides encoding the variants; nucleic acid constructs, vectors, and host cells comprising the polynucleotides; and methods of producing the variants. Furthermore, the invention relates to compositions comprising the alpha-amylase variants of the invention.

The present invention also relates to methods of producing an alpha-amylase variant of the invention, comprising:
a) cultivating the host cell of the invention under conditions suitable for expression of the variant; and
b) optionally recovering the variant.

The present invention also relates to a process for producing a syrup from starch-containing material comprising the steps of:
a) liquefying the starch-containing material at a temperature above the initial gelatinization temperature in the presence of a variant alpha-amylase according to the invention or a composition of of the invention; and
b) saccharifying the product of step a) in the presence of a glucoamylase.

In a further aspect, the present invention relates to a method for increasing stability of a parent alpha-amylase comprising introducing a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H.

Definitions

Alpha-amylase variants: Alpha-amylases (E.C. 3.2.1.1) are a group of enzymes which catalyze the hydrolysis of starch and other linear and branched 1,4 glucosidic oligo- and polysaccharides. The skilled person will know how to determine alpha-amylase activity. It may be determined according to the procedure described in the Examples, e.g., by the PNP-G7 assay, the EnzCheck assay, or the Phadebas activity assay. In one aspect, the variants of the present invention have at least 20%, e.g., at least 40%, at least 50%, at least 60%, at least 70%, at least 80%, at least 90%, at least 95%, or at least 100% of the alpha-amylase activity of the polypeptide of SEQ ID NO: 1-18. In one aspect, a variant of the present application has at least 20%, e.g., at least 40%, at least 50%, at least 60%, at least 70%, at least 80%, at least 90%, at least 95%, or at least 100% of the alpha-amylase activity of its parent.

In a further embodiment the variant alpha-amylases of the invention have an increased stability compared to a parent alpha-amylase, particularly the parent disclosed as SEQ ID NO: 1-18, and 27. In particular, the increased stability may be determined using any suitable alpha-amylase activity assay. The skilled person will know how to select a suitable assay. Examples of suitable assays and conditions have been provided in the examples herein. Such increased stability may include increased thermo-stability at pH 4.5 over the parent alpha-amylase, or increased chelator stability in model detergent A over the parent alpha-amylase. In one particular embodiment the variant alpha-amylases according to the invention have increased thermo-stability at pH 4.5, particularly increased stability determined as an improvement factor (IF) over the parent alpha-amylase, wherein the IF is determined as residual activity of the variant alpha-amylase (ratio of activity in a thermo-stressed sample over activity in a sample incubated at 4° C.) over residual activity of the parent alpha-amylase (ratio of activity in a thermo-stressed sample over activity in a sample incubated at 4° C.), in particular the variants have an IF of at least 1.1, at least 1.2, at least 1.3, at least 1.4, at least 1.5, at least 1.6, at least 1.7, at least 1.8, at least 1.9, at least 2.0.

In another particular embodiment the variant alpha-amylases according to the invention have increased chelator stability in model detergent A, particularly increased stability determined as an improvement factor (IF) over the parent alpha-amylase, wherein the IF is determined as residual activity (ratio of activity in a thermo-stressed sample over activity in a sample incubated at 4° C.) of the variant over residual activity (ratio of activity in a thermo-stressed sample over activity in a sample incubated at 4° C.) of the parent alpha-amylase, in particular the variants have an IF of at least 1.1, at least 1.2, at least 1.3, at least 1.4, at least 1.5, at least 1.6, at least 1.7, at least 1.8, at least 1.9, at least 2.0. The residual activity may be determined using any suitable alpha-amylase assay known to the skilled person, e.g., any of the assays disclosed in the examples herein. In a particular embodiment, residual activity may be determined using the Phadebas activity assay.

In another embodiment the variant alpha-amylases of the invention are capable of generating a liquefact having a dextrose equivalent (DE) value higher than the DE value generated by a parent alpha-amylase, particularly the parent disclosed in SEQ ID NO: 1-18, and 27. In particular the DE value is at least 1.5×, 2× higher than the DE value generated by the parent alpha amylse.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has alpha-amylase activity.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include increased thermo-stability at pH 4.5 over the parent alpha-amylase, or increased chelator stability in model detergent A over the parent alpha-amylase. In one particular embodiment the variant alpha-amylases according to the invention have increased thermo-stability at pH 4.5, particularly increased stability determined as an improvement factor (IF) over the parent alpha-amylase, wherein the IF is determined as residual activity of the variant alpha-amylase (ratio of activity in a themo-stressed sample over activity in a sample incubated at 4° C.) over residual activity of the parent alpha-amylase (ratio of activity in a themo-stressed sample over activity in a sample incubated at 4° C.), in particular the variants have an IF of at least 1.1, at least 1.2, at least 1.3, at least 1.4, at least 1.5, at least 1.6, at least 1.7, at least 1.8, at least 1.9, at least 2.0.

In another particular embodiment the variant alpha-amylases according to the invention have increased chelator stability in model detergent A, particularly increased stability determined as an improvement factor (IF) over the parent alpha-amylase, wherein the IF is determined as residual activity (ratio of activity in a themo-stressed sample over activity in a sample incubated at 4° C.) of the variant over residual activity (ratio of activity in a themo-stressed sample over activity in a sample incubated at 4° C.) of the parent alpha-amylase, in particular the variants have an IF of at least 1.1, at least 1.2, at least 1.3, at least 1.4, at least 1.5, at least 1.6, at least 1.7, at least 1.8, at least 1.9, at least 2.0. The residual activity may be determined using any suitable alpha-amylase assay known to the skilled person, e.g., any of the assays disclosed in the examples herein. In particular, residual activity may be determined using the Phadebas activity assay. In other embodiment the improved property comprises increased stability measured as residual alpha-amylase activity determined by EnzCheck assay after 20 min incubation at 90° C., pH 4.5, 5 ppm $Ca^{2+}$; and/or the variants are capable of generating a liquefact having a dextrose equivalent (DE) value higher than the DE value generated by a parent alpha-amylase, or the variants are capable of generating a liquefact having decreased viscosity compared to the liquefact generated by a parent alpha-amylase.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is the polypeptides disclosed as SEQ ID NO: 1-18.

It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having glucoamylase activity.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent alpha-amylase: The term "parent" or "parent alpha-amylase" means any polypeptide with alpha-amylase activity to which an alteration is made to produce the enzyme variants of the present invention.

S8A Protease: The term "S8A protease" means an S8 protease belonging to subfamily A. Subtilisins, EC 3.4.21.62, are a subgroup in subfamily S8A. The S8A protease hydrolyses the substrate Suc-Ala-Ala-Pro-Phe-pNA. The release of p-nitroaniline (pNA) results in an increase of absorbance at 405 nm and is proportional to the enzyme activity.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

Variant: The term "variant" means a polypeptide having alpha-amylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. In one embodiment the parent alpha-amylaase is selected from the group consisting of the polypeptides of SEQ ID NO: 1, 2, 3, 4, 5, 6, 7, 8, 9, 10, 11, 12, 13, 14, 15, 16, 17, and 18.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type alpha-amylase: The term "wild-type" alpha-amylase means an alpha-amylase expressed by a naturally occurring microorganism, such as a bacterium, yeast, or filamentous fungus found in nature.

Conventions for Designation of Variants

For purposes of the present invention, the mature polypeptide disclosed in SEQ ID NO: 1 is used to determine the corresponding amino acid residue in another alpha-amylase unless otherwise is stated. The amino acid sequence of another alpha-amylase is aligned with the polypeptide disclosed in SEQ ID NO: 1, and based on the alignment, the amino acid position number corresponding to any amino acid residue in the polypeptide disclosed as SEQ ID NO: 1 is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another alpha-amylase can be determined by an alignment of multiple polypeptide sequences using several computer programs including, but not limited to, MUSCLE (multiple sequence comparison by log-expectation; version 3.5 or later; Edgar, 2004, Nucleic Acids Research 32: 1792-1797), MAFFT (version 6.857 or later; Katoh and Kuma, 2002, Nucleic Acids Research 30: 3059-3066; Katoh et al., 2005, Nucleic Acids Research 33: 511-518; Katoh and Toh, 2007, Bioinformatics 23: 372-374; Katoh et al., 2009, Methods in Molecular Biology 537:_39-64; Katoh and Toh, 2010, Bioinformatics 26:1899-1900), and EMBOSS EMMA employing ClustalW (1.83 or later; Thompson et al., 1994, Nucleic Acids Research 22: 4673-4680), using their respective default parameters.

When the other enzyme has diverged from the mature polypeptide of SEQ ID NO: 1 such that traditional sequence-based comparison fails to detect their relationship (Lindahl and Elofsson, 2000, J. Mol. Biol. 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Aa" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
| --- | --- |
| 195 | 195 195a 195b |
| G | G - K - A |

Multiple Alterations.

Variants comprising multiple alterations are separated by addition marks ("+"), e.g., "Arg170Tyr+Gly195Gu" or "R170Y+G195E" representing a substitution of arginine and glycine at positions 170 and 195 with tyrosine and glutamic acid, respectively.

Different Alterations.

Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gy,Aa" designates the following variants: "Tyr167Gly+Arg170Gly", "Tyr167Gly+Arg170Ala", "Tyr167Ala+Arg170Gy", and "Tyr167Ala+Arg170Ala".

DETAILED DESCRIPTION OF THE INVENTION

The present invention relates to an alpha-amylase variant comprising at least a substitution at a position corresponding to position 188 of SEQ ID NO: 1 and at least one further substitution at a position corresponding to position 242 or 279 or 275 of SEQ ID NO: 1.

The substitution E188P in the *Bacillus stearothermophilus* alpha-amylase has previously been shown to improve stability (U.S. Pat. No. 8,084,240). The same has been shown to be the case for substitutions at position 242 when S is substituted with A, Q, E, D, or M whereas other substitutions, C, F, G, H, I, K, L, N, P, R, T, V, W, Y resulted in less activity compared to wild type (WO2009061381).

Variants

The present inventors have surprisingly found that a substitution at position 242 selected from S242Y, F, H, W, P, I, T, L, which alone will result in decreased performance, will result in a synergistic improvement in combination with an E188P substitution.

Further, the present inventors have surprisingly found that a substitution at position 279 selected from K279Y, F, H, W, I, T, L, D, M, S, N, Q, V, A which alone will result in decreased performance, will result in a synergistic improvement in combination with an E188P substitution.

Further, the present inventors have surprisingly found that a substitution at position 275 selected from N275Y, F, H, W which alone will result in decreased performance, will result in a synergistic improvement in combination with an E188P substitution.

In an embodiment, the variant has sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent alpha-amylase.

In one embodiment, the invention relates to an alpha-amylase variant comprising a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W, E188P+S242P, E188P+S242, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, wherein the variant has at least 60%, at least 65%, at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

In another embodiment, the alpha-amylase variant comprises a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H,E188P+S242W,E188P+S242P,E188P+S242I, E188P+S242T,E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1 or SEQ ID NO: 27.

In another embodiment, the alpha-amylase variant comprises a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H,E188P+S242W,E188P+S242P,E188P+S242I, E188P+S242T,E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 2.

In another embodiment, the alpha-amylase variant comprises a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3.

In another embodiment, the alpha-amylase variant comprises a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 4.

In another embodiment, the alpha-amylase variant comprises a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 5.

In another embodiment, the alpha-amylase variant comprises a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 6.

In another embodiment, the alpha-amylase variant comprises a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 7.

In another embodiment, the alpha-amylase variant comprises a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 8.

In another embodiment, the alpha-amylase variant comprises a substitution at a position corresponding to position 185 and at least one further substitution at a position corresponding to position 239 or 276 or 272 of SEQ ID NO: 2, in particular one or more combinations of substitutions selected from the group consisting of E185P+S239Y, E185P+S239F, E185P+S239H, E185P+S239W, E185P+S239P, E185P+S239I, E185P+S239T, E185P+S239L, E185P+K276W, E185P+K276Y, E185P+K276F, E185P+K276H, E185P+K276I, E185P+K276L, E185P+K276D, E185P+K276M, E185P+K276S, E185P+K276T, E185P+K276N, E185P+K276Q, E185P+K276V, E185P+K276A, E185P+N272F, E185P+N272Y, E185P+N272W, and E185P+N272H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3, and wherein the variant further comprises the specific substitutions corresponding to G48A+T49I+H68W+G107A+H156Y+A181T+I201Y+A209V+Q264S+K176L+H205Y+K213T+E255P+Q360S+D416V+R437W and optionally N190F using SEQ ID NO: 2 for numbering.

In another embodiment, the alpha-amylase variant comprises a substitution at a position corresponding to position 185 and at least one further substitution at a position corresponding to position 239 or 276 or 272 of SEQ ID NO: 2, in particular one or more combinations of substitutions selected from the group consisting of E185P+S239Y, E185P+S239F, E185P+S239H, E185P+S239W, E185P+S239P, E185P+S239I, E185P+S239T, E185P+S239L, E185P+K276W, E185P+K276Y, E185P+K276F, E185P+K276H, E185P+K276I, E185P+K276L, E185P+K276D, E185P+K276M, E185P+K276S, E185P+K276T, E185P+K276N, E185P+K276Q, E185P+K276V, E185P+K276A, E185P+N272F, E185P+N272Y, E185P+N272W, and E185P+N272H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3, and wherein the variant further comprises the specific substitutions corresponding to G48A+T49I+H68W+G107A+T116Q+H156Y+A181T+I201Y+A209V+Q264S+K176L+H205Y+K213T+E255P+Q360S+D416V+R437W and optionally N190F using SEQ ID NO: 2 for numbering.

In another embodiment, the alpha-amylase variant comprises a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H,E188P+S242W,E188P+S242P,E188P+S242I, E188P+S242T,E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1 or SEQ ID NO: 27, and wherein the variant further comprises the specific substitutions corresponding to V59A+E129V+E177L+R179E+I181*+G182*+Q254S+M284V+V212T+Y268G+N293Y+T297N and optionally N193F using SEQ ID NO: 1 for numbering.

In one embodiment, the invention relates to an alpha-amylase variant comprising a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W, E188P+S242P, E188P+S242, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, wherein the variant has at least 60%, at least 65%, at least 70%, at least 75%, at least 80%, at least 85%, at least 90%, at least 95%, at least 96%, at least 97%, at least 98%, or at least 99%, but less than 100% sequence identity to a parent alpha amylase selected from SEQ ID NO: 12.

In one embodiment, the invention relates to an alpha-amylase variant comprising a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W, E188P+S242P, E188P+S242, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, wherein the variant has at least 60%, at least 65%, at least 70%, at least 75%, at least 80%, at least 85%, at least 90%, at least 95%, at least 96%, at least 97%, at least 98%, or at least 99%, but less than 100% sequence identity to a parent alpha amylase selected from SEQ ID NO: 13.

In one embodiment, the invention relates to an alpha-amylase variant comprising a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, wherein the variant has at least 60%, at least 65%, at least 70%, at least 75%, at least 80%, at least 85%, at least 90%, at least 95%, at least 96%, at least 97%, at least 98%, or at least 99%, but less than 100% sequence identity to a parent alpha amylase selected from SEQ ID NO: 14.

In one embodiment, the invention relates to an alpha-amylase variant comprising a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, wherein the variant has at least 60%, at least 65%, at least 70%, at least 75%, at least 80%, at least 85%, at least 90%, at least 95%, at least 96%, at least 97%, at least 98%, or at least 99%, but less than 100% sequence identity to a parent alpha amylase selected from SEQ ID NO: 15.

In one embodiment, the invention relates to an alpha-amylase variant comprising a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W,E188P+S242P,E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, wherein the variant has at least 60%, at least 65%, at least 70%, at least 75%, at least 80%, at least 85%, at least 90%, at least 95%, at least 96%, at least 97%, at least 98%, or at least 99%, but less than 100% sequence identity to a parent alpha amylase selected from SEQ ID NO: 16.

In one embodiment, the invention relates to an alpha-amylase variant comprising a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W, E188P+S242P, E188P+S242, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, wherein the variant has at least 60%, at least 65%, at least 70%, at least 75%, at least 80%, at least 85%, at least 90%, at least 95%, at least 96%, at least 97%, at least 98%, or at least 99%, but less than 100% sequence identity to a parent alpha amylase selected from SEQ ID NO: 17.

In one embodiment, the invention relates to an alpha-amylase variant comprising a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W, E188P+S242P, E188P+S242, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, wherein the variant has at least 60%, at least 65%, at least 70%, at least 75%, at least 80%, at least 85%, at least 90%, at least 95%, at least 96%, at least 97%, at least 98%, or at least 99%, but less than 100% sequence identity to a parent alpha amylase selected from SEQ ID NO: 18.

In another embodiment, the alpha-amylase variant comprises a substitution at a position corresponding to position 185 and at least one further substitution at a position corresponding to position 239 or 276 or 272 of SEQ ID NO: 2, in particular one or more combinations of substitutions selected from the group consisting of E185P+S239Y, E185P+S239F, E185P+S239P, E185P+S239I, E185P+S239T, E185P+S239L, E185P+K276W, E185P+K276Y, E185P+K276F, E185P+K276H, E185P+K276I, E185P+K276L, E185P+K276D, E185P+K276M, E185P+K276S, E185P+K276T, E185P+K276N, E185P+K276Q, E185P+K276V, E185P+K276A, E185P+N272F, E185P+N272Y, E185P+N272W, and E185P+N272H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3, and wherein the variant further comprises the specific substitutions corresponding to G48A+T49I+H68W+G107A+H156Y+A181T+I201Y+A209V+Q264S+K176L+H205Y+K213T+E255P+Q360S+D416V+R437W and optionally N190F using SEQ ID NO: 2 for numbering, and wherein the variant has increased residual alpha-amylase activity determined by EnzCheck assay after 20 min incubation at 90° C., pH 4.5, 5 ppm $Ca^{2+}$ compared to SEQ ID NO: 9.

In another embodiment, the alpha-amylase variant comprises a substitution at a position corresponding to position 185 and at least one further substitution at a position corresponding to position 239 or 276 or 272 of SEQ ID NO: 2, in particular one or more combinations of substitutions selected from the group consisting of E185P+S239Y, E185P+S239F, E185P+S239P, E185P+S239I, E185P+S239T, E185P+S239L, E185P+K276W, E185P+K276Y, E185P+K276F, E185P+K276H, E185P+K276I, E185P+K276L, E185P+K276D, E185P+K276M, E185P+K276S, E185P+K276T, E185P+K276N, E185P+K276Q, E185P+K276V, E185P+K276A, E185P+N272F, E185P+N272Y, E185P+N272W, and E185P+N272H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3, and wherein the variant comprises the specific substitutions corresponding to G48A+T49I+H68W+G107A+T116Q+H156Y+A181T+I201Y+A209V+Q264S+K176L+H205Y+K213T+E255P+Q360S+D416V+R437W and optionally N190F using SEQ ID NO: 2 for numbering, and wherein the variant has increased residual alpha-amylase activity determined by EnzCheck assay after 20 min incubation at 90° C., pH 4.5, 5 ppm $Ca^{2+}$ compared to SEQ ID NO: 10.

In another embodiment, the alpha-amylase variant comprises a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 1 or SEQ ID NO: 27, and wherein the variant comprises the specific substitutions corresponding to V59A+E129V+E177L+R179E+I181*+G182*+Q254S+M284V+V212T+Y268G+N293Y+T297N and optionally N193F using SEQ ID NO: 1 for numbering, and wherein the variant has increased residual alpha-amylase activity determined by EnzCheck assay after 20 min incubation at 90° C., pH 4.5, 5 ppm $Ca^{2+}$ compared to SEQ ID NO: 11.

In another embodiment, the alpha-amylase variant comprises a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 4, and wherein the variant further comprises the specific substitutions R180*+S181*+S243Q+G475K and a C-terminal deletion of amino acids 484-583 using SEQ ID NO: 4 for numbering, and wherein the variant has increased thermo-stability and/or increased chelator stability compared to an alpha-amylase of SEQ ID NO: 4 having the specific substitutions R180*+S181*+S243Q+G475K and a C-terminal deletion of amino acids 484-583.

In another embodiment, the alpha-amylase variant comprises a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T E188P+K279N, E188P+K279Q, E188P+K279V, E188P+K279A, E188P+N275F, E188P+N275Y, E188P+N275W, and E188P+N275H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 5, and wherein the variant further comprises the specific substitutions R178*+G179*+E187P+I203Y+R458N+T459S+D460T+G476K using SEQ ID NO: 5 for numbering, and wherein the variant has increased increased thermo-stability and/or increased chelator stability compared to an alpha-amylase of SEQ ID NO: 5 having the specific substitutions R178*+G179*+E187P+I203Y+R458N+T459S+D460T+G476K.

In another embodiment, the alpha-amylase variant comprises a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T E188P+K279N, E188P+K279Q, E188P+K279V, E188P+K279A, E188P+N275F, E188P+N275Y, E188P+N275W, and E188P+N275H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 5, and wherein the variant further comprises the specific substitutions N126Y+E132H+R178*+G179*+T180D+E187P+I203Y+Y303D+G476T+G477E using SEQ ID NO: 5 for numbering, and wherein the variant has increased thermo-stability and/or increased chelator stability compared to an alpha-amylase of SEQ ID NO: 5 having the specific substitutions N126Y+E132H+R178*+G179*+T180D+E187P+I203Y+Y303D+G476T+G477E.

In another embodiment, the alpha-amylase variant comprises a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T E188P+K279N, E188P+K279Q, E188P+K279V, E188P+K279A, E188P+N275F, E188P+N275Y, E188P+N275W, and E188P+N275H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 5, and wherein the variant further comprises the specific substitutions N126Y+F153W+R178*+G179*+T180H+E187P+I203Y using SEQ ID NO: 5 for numbering, and wherein the variant has increased thermo-stability and/or increased chelator stability compared to an alpha-amylase of SEQ ID NO: 5 having the specific substitutions N126Y+F153W+R178*+G179*+T180H+E187P+I203Y.

In another embodiment, the alpha-amylase variant comprises a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T E188P+K279N, E188P+K279Q, E188P+K279V, E188P+K279A, E188P+N275F, E188P+N275Y, E188P+N275W, and E188P+N275H, and wherein the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 5, and wherein the variant further comprises the specific substitutions N126Y+F153W+R178*+G179*+T180H+I203Y+S239Q using SEQ ID NO: 5 for numbering, and wherein the variant has increased thermo-stability and/or increased chelator stability compared to an alpha-amylase of SEQ ID NO: 5 having the specific substitutions N126Y+F153W+R178*+G179*+T180H+I203Y+S239Q.

In a further aspect the present invention relates to an alpha-amylase variant comprising a substitution at a position corresponding to position 188 and further substitutions at positions corresponding to positions 242 and 279 of SEQ ID NO: 1, in particular the specific combinations selected from:
E188P+S242Y+K279;
E188P+S242L+K279W;
E188P+S242P+K279W;
E188P+S242L+K279I;
E188P+S242Y+K279W;
E188P+S242Y+K279F;
E188P+S242Y+K279H;
E188P+S242Y+K279L;
E188P+S242Y+K279Y;
E188P+S242P+K279;
E188P+S242F+K279W;
E188P+S242H+K279W;
E188P+S242W+K279W;
wherein the variant has at least 60%, e.g., at least 65%, at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of the polypeptides of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9. SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

In a still further aspect the present invention relates to an alpha-amylase variant comprising substitutions corresponding to E188P and I204Y, and further at least one substitution at a position corresponding to positions 242 or 279 of SEQ ID NO: 1, in particular the specific combinations selected from:
E188P+I204Y+S242Y;
E188P+I204Y+S242F;
E188P+I204Y+K279W;
E188P+I204Y+K279Y;
E188P+I204Y+K279F;
E188P+I204Y+K279H;
E188P+I204Y+K279I;
E188P+I204Y+K279L; and
wherein the variant has at least 60%, e.g., at least 65%, at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of the polypeptides of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9. SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

In one aspect, the number of alterations in the variants of the present invention is 1-20, e.g., 1-10 and 1-5, such as 1, 2, 3, 4, 5, 6, 7, 8, 9 or 10 alterations.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gy.

Alternatively, the amino acid changes are of such a nature that the physico-chemical properties of the polypeptides are altered.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for alpha-amylase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

The variants may consist of C-terminally truncated versions, e.g., the variant is truncated, preferably to have a length of around 490 amino acids, such as from 482-493 amino acids.

In another embodiment the variant alpha-amylase is truncated, preferably after position 484 of SEQ ID NO: 1, particularly after position 485, particularly after position 486, particularly after position 487, particularly after position 488, particularly after position 489, particularly after position 490, particularly after position 491, particularly after position 492, more particularly after position 493.

The variant alpha-amylases of the invention have an increased stability compared to a parent alpha-amylase, particularly the parents disclosed as SEQ ID NO: 1-18. In particular, the increased stability may be determined using any suitable alpha-amylase activity assay. The skilled person will know how to select a suitable assay. Examples of suitable assays and conditions have been provided in the examples herein. Such increased stability may include increased thermo-stability at pH 4.5 over the parent alpha-amylase, or increased chelator stability in model detergent A over the parent alpha-amylase. In one particular embodiment the variant alpha-amylases according to the invention have increased thermo-stability at pH 4.5, particularly increased stability determined as an improvement factor (IF) over the parent alpha-amylase, wherein the IF is determined as residual activity of the variant alpha-amylase (ratio of activity in a themo-stressed sample over activity in a sample incubated at 4° C.) over residual activity of the parent alpha-amylase (ratio of activity in a themo-stressed sample over activity in a sample incubated at 4° C.), in particular the variants have an IF of at least 1.1, at least 1.2, at least 1.3, at least 1.4, at least 1.5, at least 1.6, at least 1.7, at least 1.8, at least 1.9, at least 2.0.

In another particular embodiment the variant alpha-amylases according to the invention have increased chelator stability in model detergent A, particularly increased stability determined as an improvement factor (IF) over the parent alpha-amylase, wherein the IF is determined as residual activity (ratio of activity in a themo-stressed sample over activity in a sample incubated at 4° C.) of the variant over residual activity (ratio of activity in a themo-stressed sample over activity in a sample incubated at 4° C.) of the parent alpha-amylase, in particular the variants have an IF of at least 1.1, at least 1.2, at least 1.3, at least 1.4, at least 1.5, at least 1.6, at least 1.7, at least 1.8, at least 1.9, at least 2.0. The residual activity may be determined using any suitable alpha-amylase assay known to the skilled person, e.g., any of the assays disclosed in the examples herein. In a particular embodiment, residual activity may be determined using the Phadebas activity assay.

In another embodiment, the variants have increased thermo-stability, particularly increased stability measured as residual alpha-amylase activity determined by EnzCheck assay after 20 min incubation at 90° C., pH 4.5, 5 ppm $Ca^{2+}$ compared to a parent alpha-amylase, particularly a parent amylase selected from the group consisting of the polypeptides of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11.

In an embodiment the variants are capable of generating a liquefact having a dextrose equivalent (DE) value higher than the DE value generated by a parent alpha-amylase, particularly a parent amylase selected from the group consisting of the polypeptides of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11.

In an embodiment the variants are capable of generating a liquefact having decreased viscosity compared to the liquefact generated by a parent alpha-amylase not having the claimed double substitution, particularly a parent amylase selected from the group consisting of the polypeptides of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and SEQ ID NO: 11.

The variant polypeptide may be a hybrid polypeptide in which a region of one polypeptide is fused at the N-terminus or the C-terminus of a region of another polypeptide.

The variant may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial alpha-amylase. For example, the parent may be a Gram-positive bacterial polypeptide such as a *Bacillus, Geobacillus, Cytophaga*.

In one aspect, the parent is a *Bacillus alkalophilus, Bacillus amyloliquefaciens, Bacillus brevis, Bacillus circulans, Bacillus clausii, Bacillus coaguans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* alpha-amylase.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes.

Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7:127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a variant of the present invention. In one embodiment the polynucleotide is isolated.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the

*Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. In one embodiment the one or more control sequences are heterologous to the polynucleotide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circuans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, J. Bacteriol. 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification,* Janson and Ryden, editors, VCH Publishers, New York, 1989) to obtain substantially pure variants.

In an alternative aspect, the variant is not recovered, but rather a host cell of the present invention expressing the variant is used as a source of the variant.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Compositions

The present invention also relates to compositions comprising a variant alpha-amylase of the present invention.

The compositions may comprise a variant alpha-amylase of the present invention as the major enzymatic component, e.g., a mono-component composition. Alternatively, the compositions may comprise multiple enzymatic activities, such as one or more (e.g., several) enzymes selected from the group consisting of protease, glucoamylase, beta-amylase, pullulanase. In a particular embodiment the composition comprises a variant alpha-amylase of the present invention and a protease, particularly a protease from *Pyrococcus* sp., or *Thermococcus* sp., or a protease from *Thermoascus aurantiacus.*

In one embodiment the protease is selected from a S8 protease from *Pyrococcus furiosus* shown in SEQ ID NO: 19 or a protease having at least 85%, at least 90%, at least 95%, at least 96%, at least 97%, at least 98%, or at least 99%, or 100% sequence identity to the polypeptide of SEQ ID NO: 19.

In another embodiment the protease is selected from a variant *Thermoascus aurantiacus* protease, wherein the variant protease comprises one of the following combinations of mutations:
D79L+S87P+A112P+D142L;
D79L+S87P+D142L; or
A27K+D79L+Y82F+S87G+D104P+A112P+A126V+ D142L; and the protease variant has at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 20.

For use of the alpha-amylase variants of the invention in detergent compositions the non-limiting list of composition components illustrated hereinafter are suitable for such use, e.g. to assist or enhance cleaning performance, for treatment of the substrate to be cleaned, or to modify the aesthetics of the composition as is the case with perfumes, colorants, dyes or the like. The levels of any such components incorporated in any compositions are in addition to any materials previously recited for incorporation. The precise nature of these additional components, and levels of incorporation thereof, will depend on the physical form of the composition and the nature of the cleaning operation for which it is to be used. Although components mentioned below are categorized by general header according to a particular functionality, this is not to be construed as a limitation, as a component may comprise additional functionalities as will be appreciated by the skilled artisan. Unless otherwise indicated the amounts in percentage is by weight of the composition (wt %).

Suitable component materials include, but are not limited to, surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems, structure elasticizing agents, fabric softeners, carriers, hydrotropes, processing aids, solvents and/or pigments. In addition to the disclosure below, suitable examples of such other components and levels of use are found in U.S. Pat. Nos. 5,576,282, 6,306,812, and 6,326,348 hereby incorporated by reference.

Thus, in certain embodiments the invention do not contain one or more of the following adjuncts materials: surfactants, soaps, builders, chelating agents, dye transfer inhibiting agents, dispersants, additional enzymes, enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, perfume delivery systems, structure elasticizing agents, fabric softeners, carriers, hydrotropes, processing aids, solvents and/or pigments. However, when one or more components are present, such one or more components may be present as detailed below:

Surfactants—

The compositions according to the present invention may comprise a surfactant or surfactant system wherein the surfactant can be selected from nonionic surfactants, anionic surfactants, cationic surfactants, ampholytic surfactants, zwitterionic surfactants, semi-polar nonionic surfactants and mixtures thereof. When present, surfactant is typically present at a level of from 0.1 to 60 wt %, from 0.2 to 40 wt %, from 0.5 to 30 wt %, from 1 to 50 wt %, from 1 to 40 wt %, from 1 to 30 wt %, from 1 to 20 wt %, from 3 to 10 wt %, from 3 to 5 wt %, from 5 to 40 wt %, from 5 to 30 wt %, from 5 to 15 wt %, from 3 to 20 wt %, from 3 to 10 wt %, from 8 to 12 wt %, from 10 to 12 wt %, from 20 to 25 wt % or from 25-60%.

Suitable anionic detersive surfactants include sulphate and sulphonate detersive surfactants.

Suitable sulphonate detersive surfactants include alkyl benzene sulphonate, in one aspect, $C_{10-13}$ alkyl benzene sulphonate. Suitable alkyl benzene sulphonate (LAS) may be obtained, by sulphonating commercially available linear alkyl benzene (LAB); suitable LAB includes low 2-phenyl LAB, such as Isochem® or Petrelab®, other suitable LAB include high 2-phenyl LAB, such as Hyblene®. A suitable anionic detersive surfactant is alkyl benzene sulphonate that is obtained by DETAL catalyzed process, although other synthesis routes, such as HF, may also be suitable. In one aspect a magnesium salt of LAS is used.

Suitable sulphate detersive surfactants include alkyl sulphate, in one aspect, $C_{8-18}$ alkyl sulphate, or predominantly $C_{12}$ alkyl sulphate.

Another suitable sulphate detersive surfactant is alkyl alkoxylated sulphate, in one aspect, alkyl ethoxylated sulphate, in one aspect, a $C_{8-18}$ alkyl alkoxylated sulphate, in another aspect, a $C_{8-18}$ alkyl ethoxylated sulphate, typically the alkyl alkoxylated sulphate has an average degree of alkoxylation of from 0.5 to 20, or from 0.5 to 10, typically the alkyl alkoxylated sulphate is a $C_{8-18}$ alkyl ethoxylated sulphate having an average degree of ethoxylation of from 0.5 to 10, from 0.5 to 7, from 0.5 to 5 or from 0.5 to 3.

The alkyl sulphate, alkyl alkoxylated sulphate and alkyl benzene sulphonates may be linear or branched, substituted or un-substituted.

The detersive surfactant may be a mid-chain branched detersive surfactant, in one aspect, a mid-chain branched anionic detersive surfactant, in one aspect, a mid-chain branched alkyl sulphate and/or a mid-chain branched alkyl benzene sulphonate, e.g. a mid-chain branched alkyl sulphate. In one aspect, the mid-chain branches are $C_{1-4}$ alkyl groups, typically methyl and/or ethyl groups.

Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

Suitable non-ionic detersive surfactants are selected from the group consisting of: $C_8$-$C_{18}$ alkyl ethoxylates, such as, NEODOL®; $C_6$-$C_{12}$ alkyl phenol alkoxylates wherein the alkoxylate units may be ethyleneoxy units, propyleneoxy units or a mixture thereof; $C_{12}$-$C_{18}$ alcohol and $C_6$-$C_{12}$ alkyl phenol condensates with ethylene oxide/propylene oxide block polymers such as Pluronic®; $C_{14}$-$C_{22}$ mid-chain branched alcohols; $C_{14}$-$C_{22}$ mid-chain branched alkyl alkoxylates, typically having an average degree of alkoxylation of from 1 to 30; alkylpolysaccharides, in one aspect, alkylpolyglycosides; polyhydroxy fatty acid amides; ether capped poly(oxyalkylated) alcohol surfactants; and mixtures thereof.

Suitable non-ionic detersive surfactants include alkyl polyglucoside and/or an alkyl alkoxylated alcohol.

In one aspect, non-ionic detersive surfactants include alkyl alkoxylated alcohols, in one aspect $C_{8-18}$ alkyl alkoxylated alcohol, e.g. a $C_{8-18}$ alkyl ethoxylated alcohol, the alkyl alkoxylated alcohol may have an average degree of alkoxylation of from 1 to 50, from 1 to 30, from 1 to 20, or from 1 to 10. In one aspect, the alkyl alkoxylated alcohol may be a $C_{8-18}$ alkyl ethoxylated alcohol having an average degree of ethoxylation of from 1 to 10, from 1 to 7, more from 1 to 5 or from 3 to 7. The alkyl alkoxylated alcohol can be linear or branched, and substituted or un-substituted. Suitable nonionic surfactants include Lutensol®.

Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

Suitable cationic detersive surfactants include alkyl pyridinium compounds, alkyl quaternary ammonium compounds, alkyl quaternary phosphonium compounds, alkyl ternary sulphonium compounds, and mixtures thereof.

Suitable cationic detersive surfactants are quaternary ammonium compounds having the general formula: $(R)(R_1)(R_2)(R_3)N^+\ X^-$, wherein, R is a linear or branched, substituted or unsubstituted $C_{6-18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, suitable anions include: halides, e.g. chloride; sulphate; and sulphonate. Suitable cationic detersive surfactants are mono-$C_{6-18}$ alkyl mono-hydroxyethyl di-methyl quaternary ammonium chlorides. Highly suitable cationic detersive surfactants are mono-$C_{8-10}$ alkyl mono-hydroxyethyl di-methyl quaternary ammonium chloride, mono-$C_{10-12}$ alkyl mono-hydroxyethyl di-methyl quaternary ammonium chloride and mono-$C_{10}$ alkyl mono-hydroxyethyl di-methyl quaternary ammonium chloride.

Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

Suitable amphoteric/zwitterionic surfactants include amine oxides and betaines such as alkyldimethylbetaines, sulfobetaines, or combinations thereof. Amine-neutralized anionic surfactants—Anionic surfactants of the present invention and adjunct anionic cosurfactants, may exist in an acid form, and said acid form may be neutralized to form a surfactant salt which is desirable for use in the present detergent compositions. Typical agents for neutralization include the metal counterion base such as hydroxides, eg, NaOH or KOH. Further preferred agents for neutralizing anionic surfactants of the present invention and adjunct anionic surfactants or cosurfactants in their acid forms include ammonia, amines, or alkanolamines. Alkanolamines are preferred. Suitable non-limiting examples including monoethanolamine, diethanolamine, triethanolamine, and other linear or branched alkanolamines known in the art; e.g., highly preferred alkanolamines include 2-amino-1-propanol, 1-aminopropanol, monoisopropanolamine, or 1-amino-3-propanol. Amine neutralization may be done to a full or partial extent, e.g. part of the anionic surfactant mix may be neutralized with sodium or potassium and part of the anionic surfactant mix may be neutralized with amines or alkanolamines.

Non-limiting examples of semipolar surfactants include amine oxides (AO) such as alkyldimethylamineoxide Surfactant systems comprising mixtures of one or more anionic and in addition one or more nonionic surfactants optionally with an additional surfactant such as a cationic surfactant, may be preferred. Preferred weight ratios of anionic to nonionic surfactant are at least 2:1, or at least 1:1 to 1:10.

In one aspect, a surfactant system may comprise a mixture of isoprenoid surfactants represented by formula A and formula B:

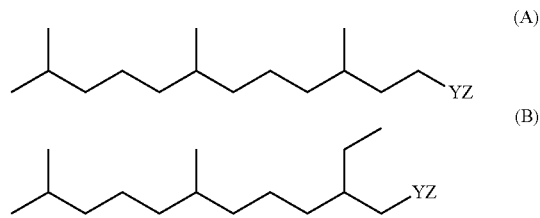

where Y is $CH_2$ or null, and Z may be chosen such that the resulting surfactant is selected from the following surfactants: an alkyl carboxylate surfactant, an alkyl polyalkoxy surfactant, an alkyl anionic polyalkoxy sulfate surfactant, an alkyl glycerol ester sulfonate surfactant, an alkyl dimethyl amine oxide surfactant, an alkyl polyhydroxy based surfactant, an alkyl phosphate ester surfactant, an alkyl glycerol sulfonate surfactant, an alkyl polygluconate surfactant, an alkyl polyphosphate ester surfactant, an alkyl phosphonate surfactant, an alkyl polyglycoside surfactant, an alkyl monoglycoside surfactant, an alkyl diglycoside surfactant, an alkyl sulfosuccinate surfactant, an alkyl disulfate surfactant, an alkyl disulfonate surfactant, an alkyl sulfosuccinamate surfactant, an alkyl glucamide surfactant, an alkyl taurinate surfactant, an alkyl sarcosinate surfactant, an alkyl glycinate surfactant, an alkyl isethionate surfactant, an alkyl dialkanolamide surfactant, an alkyl monoalkanolamide surfactant, an alkyl monoalkanolamide sulfate surfactant, an alkyl diglycolamide surfactant, an alkyl diglycolamide sulfate surfactant, an alkyl glycerol ester surfactant, an alkyl glycerol ester sulfate surfactant, an alkyl glycerol ether surfactant, an alkyl glycerol ether sulfate surfactant, alkyl methyl ester sulfonate surfactant, an alkyl polyglycerol ether surfactant, an alkyl polyglycerol ether sulfate surfactant, an alkyl sorbitan ester surfactant, an alkyl ammonioalkanesulfonate surfactant, an alkyl amidopropyl betaine surfactant, an alkyl allylated quat based surfactant, an alkyl monohydroxyalkyl-di-alkylated quat based surfactant, an alkyl di-hydroxyalkyl monoalkyl quat based surfactant, an alkylated quat surfactant, an alkyl trimethylammonium quat surfactant, an alkyl polyhydroxalkyl oxypropyl quat based surfactant, an alkyl glycerol ester quat surfactant, an alkyl glycol amine quat surfactant, an alkyl monomethyl dihydroxyethyl quaternary ammonium surfactant, an alkyl dimethyl monohydroxyethyl quaternary ammonium surfactant, an alkyl trimethylammonium surfactant, an alkyl imidazoline-based surfactant, an alken-2-yl-succinate surfactant, an alkyl a-sulfonated carboxylic acid surfactant, an alkyl a-sulfonated carboxylic acid alkyl ester surfactant, an alpha olefin sulfonate surfactant, an alkyl phenol ethoxylate surfactant, an alkyl benzenesulfonate surfactant, an alkyl sulfobetaine surfactant, an alkyl hydroxysulfobetaine surfactant, an alkyl ammoniocarboxylate betaine surfactant, an alkyl sucrose ester surfactant, an alkyl alkanolamide surfactant, an alkyl di(polyoxyethylene) monoalkyl ammonium surfactant, an alkyl mono(polyoxyethylene) dialkyl ammonium surfactant, an alkyl benzyl dimethylammonium surfactant, an alkyl aminopropionate surfactant, an alkyl amidopropyl dimethylamine surfactant, or a mixture thereof; and if Z is a charged moiety, Z is charge-balanced by a suitable metal or organic counter ion. Suitable counter ions include a metal counter ion, an amine, or an alkanolamine, e.g., C1-C6 alkanolammonium. More specifically, suitable counter ions include Na+, Ca+, Li+, K+, Mg+, e.g., monoethanolamine (MEA), diethanolamine (DEA), triethanolamine (TEA), 2-amino-I-propanol, 1-aminopropanol, methyldiethanolamine, dimethylethanolamine, monoisopropanolamine, triisopropanolamine, I-amino-3-propanol, or mixtures thereof. In one embodiment, the compositions contain from 5% to 97% of one or more non-isoprenoid surfactants; and one or more adjunct cleaning additives; wherein the weight ratio of surfactant of formula A to surfactant of formula B is from 50:50 to 95:5.

Soap—

The compositions herein may contain soap. Without being limited by theory, it may be desirable to include soap as it acts in part as a surfactant and in part as a builder and may be useful for suppression of foam and may furthermore interact favorably with the various cationic compounds of the composition to enhance softness on textile fabrics treaded with the inventive compositions. Any soap known in the art for use in laundry detergents may be utilized. In one embodiment, the compositions contain from 0 wt % to 20 wt %, from 0.5 wt % to 20 wt %, from 4 wt % to 10 wt %, or from 4 wt % to 7 wt % of soap.

Examples of soap useful herein include oleic acid soaps, palmitic acid soaps, palm kernel fatty acid soaps, and mixtures thereof. Typical soaps are in the form of mixtures of fatty acid soaps having different chain lengths and degrees of substitution. One such mixture is topped palm kernel fatty acid.

In one embodiment, the soap is selected from free fatty acid. Suitable fatty acids are saturated and/or unsaturated and can be obtained from natural sources such a plant or animal esters (e.g., palm kernel oil, palm oil, coconut oil, babassu oil, safflower oil, tall oil, castor oil, tallow and fish oils, grease, and mixtures thereof), or synthetically prepared (e.g., via the oxidation of petroleum or by hydrogenation of carbon monoxide via the Fisher Tropsch process).

Examples of suitable saturated fatty acids for use in the compositions of this invention include captic, lauric, myristic, palmitic, stearic, arachidic and behenic acid. Suitable unsaturated fatty acid species include: palmitoleic, oleic, linoleic, linolenic and ricinoleic acid. Examples of preferred fatty acids are saturated Cn fatty acid, saturated $C_2$-$C_4$ fatty acids, and saturated or unsaturated Cn to $C_8$ fatty acids, and mixtures thereof.

When present, the weight ratio of fabric softening cationic cosurfactant to fatty acid is preferably from about 1:3 to about 3:1, more preferably from about 1:1.5 to about 1.5:1, most preferably about 1:1.

Levels of soap and of nonsoap anionic surfactants herein are percentages by weight of the detergent composition, specified on an acid form basis. However, as is commonly understood in the art, anionic surfactants and soaps are in practice neutralized using sodium, potassium or alkanolammonium bases, such as sodium hydroxide or monoethanolamine.

Hydrotropes—

The compositions of the present invention may comprise one or more hydrotropes. A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined mesophases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain from 0 to 10 wt %, such as from 0 to 5 wt %, 0.5 to 5 wt %, or from 3% to 5 wt %, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders—

The compositions of the present invention may comprise one or more builders, co-builders, builder systems or a mixture thereof. When a builder is used, the cleaning composition will typically comprise from 0 to 65 wt %, at least 1 wt %, from 2 to 60 wt % or from 5 to 10 wt % builder. In a dish wash cleaning composition, the level of builder is typically 40 to 65 wt % or 50 to 65 wt %. The composition may be substantially free of builder; substantially free means "no deliberately added" zeolite and/or phosphate. Typical zeolite builders include zeolite A, zeolite P and zeolite MAP. A typical phosphate builder is sodium tri-polyphosphate.

The builder and/or co-builder may particularly be a chelating agent that forms water-soluble complexes with Ca and Mg. Any builder and/or co-builder known in the art for use in detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), iminodiethanol (DEA) and 2,2',2"-nitrilotriethanol (TEA), and carboxymethylinulin (CMI), and combinations thereof.

The cleaning composition may include a co-builder alone, or in combination with a builder, e.g. a zeolite builder. Non-limiting examples of co-builders include homopolymers of polyacrylates or copolymers thereof, such as poly (acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), etheylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diyl-bis(phosphonic acid) (HEDP), ethylenediaminetetrakis(methylene)tetrakis(phosphonic acid) (EDTMPA), diethylentriaminepentakis(methylene)pentakis(phosphonic acid) (DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N, N-diacetic acid (TUDA) and sulfomethyl-N,N-diacetic acid (SMDA), N-(hydroxyethyl)-ethylidenediaminetriacetate (HEDTA), diethanolglycine (DEG), Diethylenetriamine Penta (Methylene Phosphonic acid) (DTPMP), aminotris(methylenephosphonic acid) (ATMP), and combinations and salts thereof. Further exemplary builders and/or co-builders are described in, e.g., WO09/102854, U.S. Pat. No. 5,977,053.

Chelating Agents and Crystal Growth Inhibitors—

The compositions herein may contain a chelating agent and/or a crystal growth inhibitor. Suitable molecules include copper, iron and/or manganese chelating agents and mixtures thereof. Suitable molecules include DTPA (Diethylene triamine pentaacetic acid), HEDP (Hydroxyethane diphosphonic acid), DTPMP (Diethylene triamine penta(methylene phosphonic acid)), 1,2-Dihydroxybenzene-3,5-disulfonic acid disodium salt hydrate, ethylenediamine, diethylene triamine, ethylenediaminedisuccinic acid (EDDS), N-hydroxyethylethylenediaminetri-acetic acid (HEDTA), triethylenetetraaminehexaacetic acid (TTHA), N-hydroxyethyl-iminodiacetic acid (HEIDA), dihydroxyethylglycine (DHEG), ethylenediaminetetrapropionic acid (EDTP), carboxymethyl inulin and 2-Phosphonobutane 1,2,4-tricarboxylic acid (Bayhibit® AM) and derivatives thereof. Typically the composition may comprise from 0.005 to 15 wt % or from 3.0 to 10 wt % chelating agent or crystal growth inhibitor.

Bleach Component—

The bleach component suitable for incorporation in the methods and compositions of the invention comprise one or a mixture of more than one bleach component. Suitable bleach components include bleaching catalysts, photobleaches, bleach activators, hydrogen peroxide, sources of hydrogen peroxide, pre-formed peracids and mixtures thereof. In general, when a bleach component is used, the compositions of the present invention may comprise from 0 to 30 wt %, from 0.00001 to 90 wt %, 0.0001 to 50 wt %, from 0.001 to 25 wt % or from 1 to 20 wt %. Examples of suitable bleach components include:

(1) Pre-formed peracids: Suitable preformed peracids include, but are not limited to, compounds selected from the group consisting of pre-formed peroxyacids or salts thereof, typically either a peroxycarboxylic acid or salt thereof, or a peroxysulphonic acid or salt thereof.

The pre-formed peroxyacid or salt thereof is preferably a peroxycarboxylic acid or salt thereof, typically having a chemical structure corresponding to the following chemical formula:

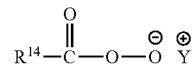

wherein: $R^{14}$ is selected from alkyl, aralkyl, cycloalkyl, aryl or heterocyclic groups; the $R^{14}$ group can be linear or branched, substituted or unsubstituted; and Y is any suitable counter-ion that achieves electric charge neutrality, preferably Y is selected from hydrogen, sodium or potassium. Preferably, $R^{14}$ is a linear or branched, substituted or unsubstituted $C_{6-9}$ alkyl. Preferably, the peroxyacid or salt thereof is selected from peroxyhexanoic acid, peroxyheptanoic acid, peroxyoctanoic acid, peroxynonanoic acid, peroxydecanoic acid, any salt thereof, or any combination thereof. Particularly preferred peroxyacids are phthalimido-peroxy-alkanoic acids, in particular ε-phthahlimido peroxy hexanoic acid (PAP). Preferably, the peroxyacid or salt thereof has a melting point in the range of from 30° C. to 60° C.

The pre-formed peroxyacid or salt thereof can also be a peroxysulphonic acid or salt thereof, typically having a chemical structure corresponding to the following chemical formula:

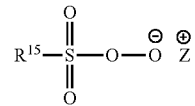

wherein: $R^{15}$ is selected from alkyl, aralkyl, cycloalkyl, aryl or heterocyclic groups; the $R^{15}$ group can be linear or branched, substituted or unsubstituted; and Z is any suitable counter-ion that achieves electric charge neutrality, preferably Z is selected from hydrogen, sodium or potassium. Preferably $R^{15}$ is a linear or branched, substituted or unsubstituted $C_{6-9}$ alkyl. Preferably such bleach components may be present in the compositions of the invention in an amount from 0.01 to 50 wt % or from 0.1 to 20 wt %.

(2) Sources of hydrogen peroxide include e.g., inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts such as those selected from the group consisting of sodium salts of perborate, percarbonate and mixtures thereof. When employed, inorganic perhydrate salts are typically present in amounts of 0.05 to 40 wt % or 1 to 30 wt % of the overall composition and are typically incorporated into such compositions as a crystalline solid that may be coated. Suitable coatings include: inorganic salts such as alkali metal silicate, carbonate or borate salts or mixtures thereof, or organic materials such as water-soluble or dispersible polymers, waxes, oils or fatty soaps. Preferably such bleach components may be present in the compositions of the invention in an amount of 0.01 to 50 wt % or 0.1 to 20 wt %.

(3) The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable bleach activators are those having R—(C=O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED), sodium 4-[(3,5,5-trimethylhexanoyl)oxy] benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), and/or those disclosed in WO98/17767. A family of bleach activators is disclosed in EP624154 and particularly preferred in that family is acetyl triethyl citrate (ATC). ATC or a short chain triglyceride like triacetin has the advantage that it is environmentally friendly. Furthermore acetyl triethyl citrate and triacetin have good hydrolytical stability in the product upon storage and are efficient bleach activators. Finally ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido)peroxyhexanoic acid (PAP). Suitable bleach activators are also disclosed in WO98/17767. While any suitable bleach activator may be employed, in one aspect of the invention the subject cleaning composition may comprise NOBS, TAED or mixtures thereof. When present, the peracid and/or bleach activator is generally present in the composition in an amount of 0.1 to 60 wt %, 0.5 to 40 wt % or 0.6 to 10 wt % based on the fabric and home care composition. One or more hydrophobic peracids or precursors thereof may be used in combination with one or more hydrophilic peracid or precursor thereof. Preferably such bleach components may be present in the compositions of the invention in an amount of 0.01 to 50 wt %, or 0.1 to 20 wt %.

The amounts of hydrogen peroxide source and peracid or bleach activator may be selected such that the molar ratio of available oxygen (from the peroxide source) to peracid is from 1:1 to 35:1, or even 2:1 to 10:1.

(4) Diacyl peroxides—preferred diacyl peroxide bleaching species include those selected from diacyl peroxides of the general formula: $R^1$—C(O)—OO—(O)C—$R^2$, in which $R^1$ represents a $C_6$-$C_{18}$ alkyl, preferably $C_6$-$C_{12}$ alkyl group containing a linear chain of at least 5 carbon atoms and optionally containing one or more substituents (e.g. —N$^+$(CH$_3$)$_3$, —COOH or —CN) and/or one or more interrupting moieties (e.g. —CONH— or —CH=CH—) interpolated between adjacent carbon atoms of the alkyl radical, and $R^2$ represents an aliphatic group compatible with a peroxide moiety, such that $R^1$ and $R^2$ together contain a total of 8 to 30 carbon atoms. In one preferred aspect $R^1$ and R2 are linear unsubstituted $C_6$-$C_{12}$ alkyl chains. Most preferably $R^1$ and R2 are identical. Diacyl peroxides, in which both $R^1$ and $R^2$ are $C_6$-$C_{12}$ alkyl groups, are particularly preferred. Preferably, at least one of, most preferably only one of, the R groups ($R_1$ or $R_2$), does not contain branching or pendant rings in the alpha position, or preferably neither in the alpha nor beta positions or most preferably in none of the alpha or beta or gamma positions. In one further preferred embodiment, the DAP may be asymmetric, such that preferably the hydrolysis of R1 acyl group is rapid to generate peracid, but the hydrolysis of R2 acyl group is slow.

The tetraacyl peroxide bleaching species is preferably selected from tetraacyl peroxides of the general formula: $R^3$—C(O)—OO—C(O)—(CH$_2$)n-C(O)—OO—C(O)—$R^3$, in which $R^3$ represents a $C_1$-$C_9$ alkyl, or $C_3$-$C_7$ group and n represents an integer from 2 to 12, or 4 to 10 inclusive.

Preferably, the diacyl and/or tetraacyl peroxide bleaching species is present in an amount sufficient to provide at least 0.5 ppm, at least 10 ppm, or at least 50 ppm by weight of the wash liquor. In a preferred embodiment, the bleaching species is present in an amount sufficient to provide from 0.5 to 300 ppm, from 30 to 150 ppm by weight of the wash liquor.

Preferably the bleach component comprises a bleach catalyst (5 and 6).

(5) Preferred are organic (non-metal) bleach catalysts include bleach catalyst capable of accepting an oxygen atom from a peroxyacid and/or salt thereof, and transferring the oxygen atom to an oxidizeable substrate. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof.

Suitable iminium cations and polyions include, but are not limited to, N-methyl-3,4-dihydroisoquinolinium tetrafluoroborate, prepared as described in Tetrahedron (1992), 49(2), 423-38 (e.g. compound 4, p. 433); N-methyl-3,4-dihydroisoquinolinium p-toluene sulphonate, prepared as described in U.S. Pat. No. 5,360,569 (e.g. Column 11, Example 1); and N-octyl-3,4-dihydroisoquinolinium p-toluene sulphonate, prepared as described in U.S. Pat. No. 5,360,568 (e.g. Column 10, Ex. 3).

Suitable iminium zwitterions include, but are not limited to, N-(3-sulfopropyl)-3,4-dihydroisoquinolinium, inner salt, prepared as described in U.S. Pat. No. 5,576,282 (e.g. Column 31, Ex. II); N-[2-(sulphooxy)dodecyl]-3,4-dihydroisoquinolinium, inner salt, prepared as described in U.S. Pat. No. 5,817,614 (e.g. Column 32, Ex. V); 2-[3-[(2-ethylhexyl)oxy]-2-(sulphooxy)propyl]-3,4-dihydroisoquinolinium, inner salt, prepared as described in WO05/047264 (e.g. p. 18, Ex. 8), and 2-[3-[(2-butyloctyl)oxy]-2-(sulphooxy)propyl]-3,4-dihydroisoquinolinium, inner salt.

Suitable modified amine oxygen transfer catalysts include, but are not limited to, 1,2,3,4-tetrahydro-2-methyl-1-isoquinolinol, which can be made according to the procedures described in Tetrahedron Letters (1987), 28(48), 6061-6064. Suitable modified amine oxide oxygen transfer catalysts include, but are not limited to, sodium 1-hydroxy-N-oxy-N-[2-(sulphooxy)decyl]-1,2,3,4-tetrahydroisoquinoline.

Suitable N-sulphonyl imine oxygen transfer catalysts include, but are not limited to, 3-methyl-1,2-benzisothiazole 1,1-dioxide, prepared according to the procedure described in the Journal of Organic Chemistry (1990), 55(4), 1254-61.

Suitable N-phosphonyl imine oxygen transfer catalysts include, but are not limited to, [R-(E)]-N-[(2-chloro-5-nitrophenyl)methylene]-P-phenyl-P-(2,4,6-trimethylphenyl)-phosphinic amide, which can be made according to the procedures described in the Journal of the Chemical Society, Chemical Communications (1994), (22), 2569-70.

Suitable N-acyl imine oxygen transfer catalysts include, but are not limited to, [N(E)]-N-(phenylmethylene)acetamide, which can be made according to the procedures described in Polish Journal of Chemistry (2003), 77(5), 577-590.

Suitable thiadiazole dioxide oxygen transfer catalysts include but are not limited to, 3-methyl-4-phenyl-1,2,5-thiadiazole 1,1-dioxide, which can be made according to the procedures described in U.S. Pat. No. 5,753,599 (Column 9, Ex. 2).

Suitable perfluoroimine oxygen transfer catalysts include, but are not limited to, (Z)-2,2,3,3,4,4,4-heptafluoro-N-(nonafluorobutyl)butanimidoyl fluoride, which can be made according to the procedures described in Tetrahedron Letters (1994), 35(34), 6329-30.

Suitable cyclic sugar ketone oxygen transfer catalysts include, but are not limited to, 1,2:4,5-di-O-isopropylidene-D-erythro-2,3-hexodiuro-2,6-pyranose as prepared in U.S. Pat. No. 6,649,085 (Column 12, Ex. 1).

Preferably, the bleach catalyst comprises an iminium and/or carbonyl functional group and is typically capable of forming an oxaziridinium and/or dioxirane functional group upon acceptance of an oxygen atom, especially upon acceptance of an oxygen atom from a peroxyacid and/or salt thereof. Preferably, the bleach catalyst comprises an oxaziridinium functional group and/or is capable of forming an oxaziridinium functional group upon acceptance of an oxygen atom, especially upon acceptance of an oxygen atom from a peroxyacid and/or salt thereof. Preferably, the bleach catalyst comprises a cyclic iminium functional group, preferably wherein the cyclic moiety has a ring size of from five to eight atoms (including the nitrogen atom), preferably six atoms. Preferably, the bleach catalyst comprises an aryliminium functional group, preferably a bi-cyclic aryliminium functional group, preferably a 3,4-dihydroisoquinolinium functional group.

Typically, the imine functional group is a quaternary imine functional group and is typically capable of forming a quaternary oxaziridinium functional group upon acceptance of an oxygen atom, especially upon acceptance of an oxygen atom from a peroxyacid and/or salt thereof. In another aspect, the detergent composition comprises a bleach component having a log $P_{o/w}$ no greater than 0, no greater than $-0.5$, no greater than $-1.0$, no greater than $-1.5$, no greater than $-2.0$, no greater than $-2.5$, no greater than $-3.0$, or no greater than $-3.5$. The method for determining log $P_{o/w}$ is described in more detail below.

Typically, the bleach ingredient is capable of generating a bleaching species having a $X_{SO}$ of from 0.01 to 0.30, from 0.05 to 0.25, or from 0.10 to 0.20. The method for determining $X_{SO}$ is described in more detail below. For example, bleaching ingredients having an isoquinolinium structure are capable of generating a bleaching species that has an oxaziridinium structure. In this example, the $X_{SO}$ is that of the oxaziridinium bleaching species.

Preferably, the bleach catalyst has a chemical structure corresponding to the following chemical formula:

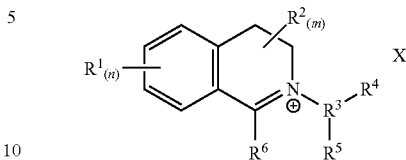

wherein: n and m are independently from 0 to 4, preferably n and m are both 0; each $R^1$ is independently selected from a substituted or unsubstituted radical selected from the group consisting of hydrogen, alkyl, cycloalkyl, aryl, fused aryl, heterocyclic ring, fused heterocyclic ring, nitro, halo, cyano, sulphonato, alkoxy, keto, carboxylic, and carboalkoxy radicals; and any two vicinal $R^1$ substituents may combine to form a fused aryl, fused carbocyclic or fused heterocyclic ring; each $R^2$ is independently selected from a substituted or unsubstituted radical independently selected from the group consisting of hydrogen, hydroxy, alkyl, cycloalkyl, alkaryl, aryl, aralkyl, alkylenes, heterocyclic ring, alkoxys, arylcarbonyl groups, carboxyalkyl groups and amide groups; any $R^2$ may be joined together with any other of $R^2$ to form part of a common ring; any geminal $R^2$ may combine to form a carbonyl; and any two $R^2$ may combine to form a substituted or unsubstituted fused unsaturated moiety; $R^3$ is a $C_1$ to $C_{20}$ substituted or unsubstituted alkyl; $R^4$ is hydrogen or the moiety $Q_t$-A, wherein: Q is a branched or unbranched alkylene, t=0 or 1 and A is an anionic group selected from the group consisting of $OSO_3^-$, $SO_3^-$, $CO_2^-$, $OCO_2^-$, $OPO_3^{2-}$, $OPO_3H^-$ and $OPO_2^-$; $R^5$ is hydrogen or the moiety $-CR^{11}R^{12}-Y-G_b-Y_c-[(CR^9R^{10})_y-O]_k-R^8$, wherein: each Y is independently selected from the group consisting of O, S, N—H, or N—$R^8$; and each $R^8$ is independently selected from the group consisting of alkyl, aryl and heteroaryl, said moieties being substituted or unsubstituted, and whether substituted or unsubstituted said moieties having less than 21 carbons; each G is independently selected from the group consisting of CO, $SO_2$, SO, PO and $PO_2$; $R^9$ and $R^{10}$ are independently selected from the group consisting of H and $C_1$-$C_4$ alkyl; $R^{11}$ and $R^{12}$ are independently selected from the group consisting of H and alkyl, or when taken together may join to form a carbonyl; b=0 or 1; c can=0 or 1, but c must=0 if b=0; y is an integer from 1 to 6; k is an integer from 0 to 20; $R^0$ is H, or an alkyl, aryl or heteroaryl moiety; said moieties being substituted or unsubstituted; and X, if present, is a suitable charge balancing counterion, preferably X is present when $R^4$ is hydrogen, suitable X, include but are not limited to: chloride, bromide, sulphate, methosulphate, sulphonate, p-toluenesulphonate, borontetraflouride and phosphate.

In one embodiment of the present invention, the bleach catalyst has a structure corresponding to general formula below:

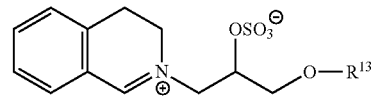

wherein $R^{13}$ is a branched alkyl group containing from three to 24 carbon atoms (including the branching carbon atoms) or a linear alkyl group containing from one to 24 carbon atoms; preferably $R^{13}$ is a branched alkyl group containing from eight to 18 carbon atoms or linear alkyl group containing from eight to eighteen carbon atoms; preferably $R^{13}$ is selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl; preferably $R^{13}$ is selected from the group consisting of 2-butyloctyl, 2-pentylnonyl, 2-hexyldecyl, iso-tridecyl and iso-pentadecyl.

Preferably the bleach component comprises a source of peracid in addition to bleach catalyst, particularly organic bleach catalyst. The source of peracid may be selected from (a) pre-formed peracid; (b) percarbonate, perborate or persulfate salt (hydrogen peroxide source) preferably in combination with a bleach activator; and (c) perhydrolase enzyme and an ester for forming peracid in situ in the presence of water in a textile or hard surface treatment step.

When present, the peracid and/or bleach activator is generally present in the composition in an amount of from 0.1 to 60 wt %, from 0.5 to 40 wt % or from 0.6 to 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or 2:1 to 10:1.

(6) Metal-containing Bleach Catalysts—The bleach component may be provided by a catalytic metal complex. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methylenephosphonic acid) and water-soluble salts thereof. Such catalysts are disclosed in U.S. Pat. No. 4,430,243. Preferred catalysts are described in WO09/839406, U.S. Pat. No. 6,218,351 and WO00/012667. Particularly preferred are transition metal catalyst or ligands therefore that are cross-bridged polydentate N-donor ligands.

If desired, the compositions herein can be catalyzed by means of a manganese compound. Such compounds and levels of use are well known in the art and include, e.g., the manganese-based catalysts disclosed in U.S. Pat. No. 5,576,282.

Cobalt bleach catalysts useful herein are known, and are described e.g. in U.S. Pat. No. 5,597,936; 5,595,967. Such cobalt catalysts are readily prepared by known procedures, such as taught e.g. in U.S. Pat. Nos. 5,597,936 and 5,595,967.

Compositions herein may also suitably include a transition metal complex of ligands such as bispidones (U.S. Pat. No. 7,501,389) and/or macropolycyclic rigid ligands—abbreviated as "MRLs". As a practical matter, and not by way of limitation, the compositions and processes herein can be adjusted to provide on the order of at least one part per hundred million of the active MRL species in the aqueous washing medium, and will typically provide from 0.005 to 25 ppm, from 0.05 to 10 ppm, or from 0.1 to 5 ppm, of the MRL in the wash liquor.

Suitable transition-metals in the instant transition-metal bleach catalyst include e.g. manganese, iron and chromium. Suitable MRLs include 5,12-diethyl-1,5,8,12-tetraazabicyclo[6.6.2]hexadecane. Suitable transition metal MRLs are readily prepared by known procedures, such as taught e.g. in U.S. Pat. No. 6,225,464 and WO00/32601.

(7) Photobleaches—suitable photobleaches include e.g. sulfonated zinc phthalocyanine sulfonated aluminium phthalocyanines, xanthene dyes and mixtures thereof. Preferred bleach components for use in the present compositions of the invention comprise a hydrogen peroxide source, bleach activator and/or organic peroxyacid, optionally generated in situ by the reaction of a hydrogen peroxide source and bleach activator, in combination with a bleach catalyst. Preferred bleach components comprise bleach catalysts, preferably organic bleach catalysts, as described above.

Particularly preferred bleach components are the bleach catalysts in particular the organic bleach catalysts.

Exemplary bleaching systems are also described, e.g. in WO2007/087258, WO2007/087244, WO2007/087259 and WO2007/087242.

Fabric Hueing Agents—

The composition may comprise a fabric hueing agent. Suitable fabric hueing agents include dyes, dye-clay conjugates, and pigments. Suitable dyes include small molecule dyes and polymeric dyes. Suitable small molecule dyes include small molecule dyes selected from the group consisting of dyes falling into the Color Index (C.I.) classifications of Direct Blue, Direct Red, Direct Violet, Acid Blue, Acid Red, Acid Violet, Basic Blue, Basic Violet and Basic Red, or mixtures thereof.

In another aspect, suitable small molecule dyes include small molecule dyes selected from the group consisting of Color Index (Society of Dyers and Colorists, Bradford, UK) numbers Direct Violet 9, Direct Violet 35, Direct Violet 48, Direct Violet 51, Direct Violet 66, Direct Violet 99, Direct Blue 1, Direct Blue 71, Direct Blue 80, Direct Blue 279, Acid Red 17, Acid Red 73, Acid Red 88, Acid Red 150, Acid Violet 15, Acid Violet 17, Acid Violet 24, Acid Violet 43, Acid Red 52, Acid Violet 49, Acid Violet 50, Acid Blue 15, Acid Blue 17, Acid Blue 25, Acid Blue 29, Acid Blue 40, Acid Blue 45, Acid Blue 75, Acid Blue 80, Acid Blue 83, Acid Blue 90 and Acid Blue 113, Acid Black 1, Basic Violet 1, Basic Violet 3, Basic Violet 4, Basic Violet 10, Basic Violet 35, Basic Blue 3, Basic Blue 16, Basic Blue 22, Basic Blue 47, Basic Blue 66, Basic Blue 75, Basic Blue 159 and mixtures thereof. In another aspect, suitable small molecule dyes include small molecule dyes selected from the group consisting of Color Index (Society of Dyers and Colorists, Bradford, UK) numbers Acid Violet 17, Acid Violet 43, Acid Red 52, Acid Red 73, Acid Red 88, Acid Red 150, Acid Blue 25, Acid Blue 29, Acid Blue 45, Acid Blue 113, Acid Black 1, Direct Blue 1, Direct Blue 71, Direct Violet 51 and mixtures thereof. In another aspect, suitable small molecule dyes include small molecule dyes selected from the group consisting of Color Index (Society of Dyers and Colorists, Bradford, UK) numbers Acid Violet 17, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing conjugated chromogens (dye-polymer conjugates) and polymers with chromogens co-polymerized into the backbone of the polymer and mixtures thereof.

In another aspect, suitable polymeric dyes include polymeric dyes selected from the group consisting of fabric-substantive colorants sold under the name of Liquitint® (Milliken), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colorants, alkoxylated thiophene polymeric colorants, and mixtures thereof.

Preferred hueing dyes include the whitening agents found in WO08/87497. These whitening agents may be characterized by the following structure (1):

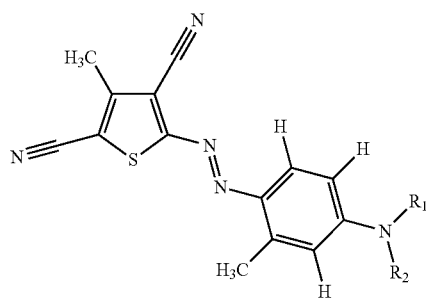

wherein $R_1$ and $R_2$ can independently be selected from:

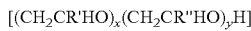  a)

wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein $x+y \leq 5$; wherein $y \geq 1$; and wherein $z=0$ to 5;

$R_1$=alkyl, aryl or aryl alkyl and $R_2$=[(CH$_2$CR'HO)$_x$ (CH$_2$CR"HO)$_y$H]    b)

wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein $x+y \leq 10$; wherein $y \geq 1$; and wherein $z=0$ to 5;

$R_1$=[CH$_2$CH$_2$(OR$_3$)CH$_2$OR$_4$] and $R_2$=[CH$_2$CH$_2$ (OR$_3$)CH$_2$OR$_4$]    c)

wherein $R_3$ is selected from the group consisting of H, $(CH_2CH_2O)_zH$, and mixtures thereof; and wherein $z=0$ to 10;

wherein $R_4$ is selected from the group consisting of $(C_1-C_{16})$alkyl, aryl groups, and mixtures thereof; and d) wherein R1 and R2 can independently be selected from the amino addition product of styrene oxide, glycidyl methyl ether, isobutyl glycidyl ether, isopropylglycidyl ether, t-butyl glycidyl ether, 2-ethylhexylgycidyl ether, and glycidylhexadecyl ether, followed by the addition of from 1 to 10 alkylene oxide units.

A preferred whitening agent of the present invention may be characterized by the following structure (II):

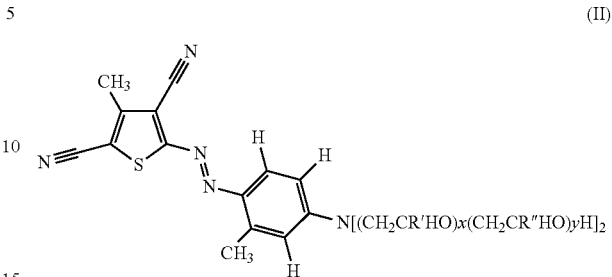

wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein $x+y \leq 5$; wherein $y \geq 1$; and wherein $z=0$ to 5.

A further preferred whitening agent of the present invention may be characterized by the following structure (III):

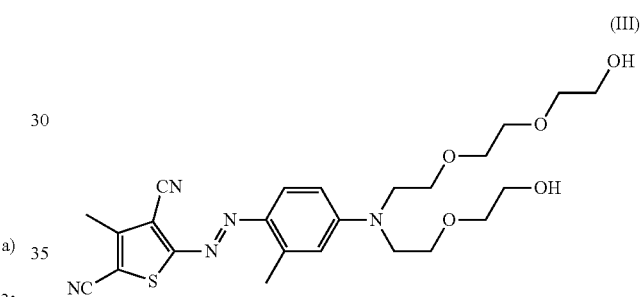

typically comprising a mixture having a total of 5 EO groups. Suitable preferred molecules are those in Structure I having the following pendant groups in "part a" above.

|   | R1 | | | | R2 | | | |
|---|---|---|---|---|---|---|---|---|
|   | R' | R" | X | y | R' | R" | x | y |
| A | H | H | 3 | 1 | H | H | 0 | 1 |
| B | H | H | 2 | 1 | H | H | 1 | 1 |
| c = b | H | H | 1 | 1 | H | H | 2 | 1 |
| d = a | H | H | 0 | 1 | H | H | 3 | 1 |

Further whitening agents of use include those described in US2008/34511 (Unilever). A preferred agent is "Violet 13".

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, C.I. Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I.

42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by C1-C3-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof.

In another aspect, suitable pigments include pigments selected from the group consisting of Ultramarine Blue (C.I. Pigment Blue 29), Ultramarine Violet (C.I. Pigment Violet 15) and mixtures thereof.

The aforementioned fabric hueing agents can be used in combination (any mixture of fabric hueing agents can be used). Suitable hueing agents are described in more detail in U.S. Pat. No. 7,208,459. Preferred levels of dye in compositions of the invention are 0.00001 to 0.5 wt %, or 0.0001 to 0.25 wt %. The concentration of dyes preferred in water for the treatment and/or cleaning step is from 1 ppb to 5 ppm, 10 ppb to 5 ppm or 20 ppb to 5 ppm. In preferred compositions, the concentration of surfactant will be from 0.2 to 3 g/l.

Encapsulates—

The composition may comprise an encapsulate. In one aspect, an encapsulate comprising a core, a shell having an inner and outer surface, said shell encapsulating said core.

In one aspect of said encapsulate, said core may comprise a material selected from the group consisting of perfumes; brighteners; dyes; insect repellants; silicones; waxes; flavors; vitamins; fabric softening agents; skin care agents in one aspect, paraffins; enzymes; anti-bacterial agents; bleaches; sensates; and mixtures thereof; and said shell may comprise a material selected from the group consisting of polyethylenes; polyamides; polyvinylalcohols, optionally containing other co-monomers; polystyrenes; polyisoprenes; polycarbonates; polyesters; polyacrylates; aminoplasts, in one aspect said aminoplast may comprise a polyureas, polyurethane, and/or polyureaurethane, in one aspect said polyurea may comprise polyoxymethyleneurea and/or melamine formaldehyde; polyolefins; polysaccharides, in one aspect said polysaccharide may comprise alginate and/or chitosan; gelatin; shellac; epoxy resins; vinyl polymers; water insoluble inorganics; silicone; and mixtures thereof.

In one aspect of said encapsulate, said core may comprise perfume.

In one aspect of said encapsulate, said shell may comprise melamine formaldehyde and/or cross linked melamine formaldehyde.

In a one aspect, suitable encapsulates may comprise a core material and a shell, said shell at least partially surrounding said core material, is disclosed. At least 75%, 85% or 90% of said encapsulates may have a fracture strength of from 0.2 to 10 MPa, from 0.4 to 5 MPa, from 0.6 to 3.5 MPa, or from 0.7 to 3 MPa; and a benefit agent leakage of from 0 to 30%, from 0 to 20%, or from 0 to 5%.

In one aspect, at least 75%, 85% or 90% of said encapsulates may have a particle size from 1 to 80 microns, from 5 to 60 microns, from 10 to 50 microns, or from 15 to 40 microns.

In one aspect, at least 75%, 85% or 90% of said encapsulates may have a particle wall thickness from 30 to 250 nm, from 80 to 180 nm, or from 100 to 160 nm.

In one aspect, said encapsulates' core material may comprise a material selected from the group consisting of a perfume raw material and/or optionally a material selected from the group consisting of vegetable oil, including neat and/or blended vegetable oils including castor oil, coconut oil, cottonseed oil, grape oil, rapeseed, soybean oil, corn oil, palm oil, linseed oil, safflower oil, olive oil, peanut oil, coconut oil, palm kernel oil, castor oil, lemon oil and mixtures thereof; esters of vegetable oils, esters, including dibutyl adipate, dibutyl phthalate, butyl benzyl adipate, benzyl octyl adipate, tricresyl phosphate, trioctyl phosphate and mixtures thereof; straight or branched chain hydrocarbons, including those straight or branched chain hydrocarbons having a boiling point of greater than about 80° C.; partially hydrogenated terphenyls, dialkyl phthalates, alkyl biphenyls, including monoisopropylbiphenyl, alkylated naphthalene, including dipropylnaphthalene, petroleum spirits, including kerosene, mineral oil and mixtures thereof; aromatic solvents, including benzene, toluene and mixtures thereof; silicone oils; and mixtures thereof.

In one aspect, said encapsulates' wall material may comprise a suitable resin including the reaction product of an aldehyde and an amine, suitable aldehydes include, formaldehyde. Suitable amines include melamine, urea, benzoguanamine, glycoluril, and mixtures thereof. Suitable melamines include methylol melamine, methylated methylol melamine, imino melamine and mixtures thereof. Suitable ureas include dimethylol urea, methylated dimethylol urea, urea-resorcinol, and mixtures thereof.

In one aspect, suitable formaldehyde scavengers may be employed with the encapsulates e.g. in a capsule slurry and/or added to a composition before, during or after the encapsulates are added to such composition. Suitable capsules may be made by the following teaching of US2008/0305982; and/or US2009/0247449.

In a preferred aspect the composition can also comprise a deposition aid, preferably consisting of the group comprising cationic or nonionic polymers. Suitable polymers include cationic starches, cationic hydroxyethylcellulose, polyvinylformaldehyde, locust bean gum, mannans, xyloglucans, tamarind gum, polyethyleneterephthalate and polymers containing dimethylaminoethyl methacrylate, optionally with one or monomers selected from the group comprising acrylic acid and acrylamide.

Perfumes—

In one aspect the composition comprises a perfume that comprises one or more perfume raw materials selected from the group consisting of 1,1'-oxybis-2-propanol; 1,4-cyclohexanedicarboxylic acid, diethyl ester; (ethoxymethoxy)cyclododecane; 1,3-nonanediol, monoacetate; (3-methylbutoxy)acetic acid, 2-propenyl ester; beta-methyl cyclododecaneethanol; 2-methyl-3-[(1,7,7-trimethylbicyclo[2.2.1]hept-2-yl)oxy]-1-propanol; oxacyclohexadecan-2-one; alpha-methyl-benzenemethanol acetate; trans-3-ethoxy-1,1,5-trimethylcyclohexane; 4-(1,1-dimethylethyl)cyclohexanol acetate; dodecahydro-3a,6,6,9a-tetramethylnaphtho[2,1-b]furan; beta-methyl benzenepropanal; beta-methyl-3-(1-methylethyl)benzenepropanal; 4-phenyl-2-butanone; 2-methylbutanoic acid, ethyl ester; benzaldehyde; 2-methylbutanoic acid, 1-methylethyl ester; dihydro-5-pentyl-2(3H)furanone; (2E)-1-(2,6,6-trimethyl-2-cyclohexen-1-yl)-2-buten-1-one; dodecanal; undecanal; 2-ethyl-alpha, alpha-dimethylbenzenepropanal; decanal; alpha, alpha-dimethylbenzeneethanol acetate; 2-(phenylmethylene)octanal; 2-[[3-[4-(1,1-dimethylethyl)phenyl]-2-methylpropylidene]amino]benzoic acid, methyl ester; 1-(2,6,6-trimethyl-3-cyclohexen-1-yl)-2-buten-1-one; 2-pentylcyclopentanone; 3-oxo-2-pentyl cyclopentaneacetic acid, methyl ester; 4-hydroxy-3-methoxybenzaldehyde; 3-ethoxy-4-hydroxybenzaldehyde; 2-heptylcyclopentanone; 1-(4-methylphenyl)ethanone; (3E)-4-(2,6,6-trimethyl-1-cyclohexen-1-yl)-3-buten-2-one; (3E)-4-(2,6,6-trimethyl-1-cyclohexen-1-yl)-3-buten-2-one; benzeneethanol; 2H-1-benzopyran-2-one; 4-methoxybenzaldehyde; 10-undecenal; propanoic acid, phenylmethyl ester; beta-methylbenzenepentanol; 1,1-diethoxy-3,7-dimethyl-2,6-octadiene; alpha, alpha-dimethylbenzeneethanol; (2E)-1-(2,6,6-trimethyl-1-cyclohexen-1-yl)-2-buten-1-one; acetic acid, phenylmethyl ester; cyclohexanepropanoic acid, 2-propenyl ester; hexanoic acid, 2-propenyl ester; 1,2-dimethoxy-4-(2-propenyl)benzene; 1,5-dimethyl-bicyclo[3.2.1]octan-8-one oxime; 4-(4-hydroxy-4-methylpentyl)-3-cyclohexene-1-carboxaldehyde; 3-buten-2-ol; 2-[[[2,4(or 3,5)-dimethyl-3-cyclohexen-1-yl]methylene]amino]benzoic acid, methyl ester; 8-cyclohexadecen-1-one; methyl ionone; 2,6-dimethyl-7-octen-2-ol; 2-methoxy-4-(2-propenyl)phenol; (2E)-3,7-dimethyl-2,6-Octadien-1-ol; 2-hydroxy-Benzoic acid, (3Z)-3-hexenyl ester; 2-tridecenenitrile; 4-(2,2-dimethyl-6-methylenecyclohexyl)-3-methyl-3-buten-2-one; tetrahydro-4-methyl-2-(2-methyl-1-propenyl)-2H-pyran; Acetic acid, (2-methylbutoxy)-, 2-propenyl ester; Benzoic acid, 2-hydroxy-3-methylbutyl ester; 2-Buten-1-one, 1-(2,6,6-trimethyl-1-cyclohexen-1-yl)-, (Z)-; Cyclopentanecarboxylic acid, 2-hexyl-3-oxo-, methyl ester; Benzenepropanal, 4-ethyl-.alpha.,.alpha.-dimethyl-; 3-Cyclohexene-1-carboxaldehyde, 3-(4-hydroxy-4-methylpentyl)-; Ethanone, 1-(2,3,4,7,8,8a-hexahydro-3,6,8,8-tetramethyl-1H-3a,7-methanoazulen-5-yl)-, [3R-(3.alpha.,3a.beta.,7.beta.,8a.alpha.)]-; Undecanal, 2-methyl-2H-Pyran-2-one, 6-butyltetrahydro-; Benzenepropanal, 4-(1,1-dimethylethyl)-.alpha.-methyl-; 2(3H)-Furanone, 5-heptyldihydro-; Benzoic acid, 2-[(7-hydroxy-3,7-dimethyloctylidene)amino]-, methyl; Benzoic acid, 2-hydroxy-, phenylmethyl ester; Naphthalene, 2-methoxy-; 2-Cyclopenten-1-one, 2-hexyl-; 2(3H)-Furanone, 5-hexyldihydro-; Oxiranecarboxylic acid, 3-methyl-3-phenyl-, ethyl ester; 2-Oxabicyclo[2.2.2]octane, 1,3,3-trimethyl-; Benzenepentanol, .gamma.-methyl-; 3-Octanol, 3,7-dimethyl-; 3,7-dimethyl-2,6-octadienenitrile; 3,7-dimethyl-6-octen-1-ol; Terpineol acetate; 2-methyl-6-methylene-7-Octen-2-ol, dihydro derivative; 3a,4,5,6,7,7a-hexahydro-4,7-Methano-1H-inden-6-ol propanoate; 3-methyl-2-buten-1-ol acetate; (Z)-3-Hexen-1-ol acetate; 2-ethyl-4-(2,2,3-trimethyl-3-cyclopenten-1-yl)-2-buten-1-ol; 4-(octahydro-4,7-methano-5H-inden-5-ylidene)-butanal; 3-2,4-dimethyl-cyclohexene-1-carboxaldehyde; 1-(1,2,3,4,5,6,7,8-octahydro-2,3,8,8-tetramethyl-2-naphthalenyl)-ethanone; 2-hydroxy-benzoic acid, methyl ester; 2-hydroxy-benzoic acid, hexyl ester; 2-phenoxy-ethanol; 2-hydroxy-benzoic acid, pentyl ester; 2,3-heptanedione; 2-hexen-1-ol; 6-Octen-2-ol, 2,6-dimethyl-; damascone (alpha, beta, gamma or delta or mixtures thereof), 4,7-Methano-1H-inden-6-ol, 3a,4,5,6,7,7a-hexahydro-, acetate; 9-Undecenal; 8-Undecenal; Isocyclocitral; Ethanone, 1-(1,2,3,5,6,7,8,8a-octahydro-2,3,8,8-tetramethyl-2-naphthalenyl)-; 3-Cyclohexene-1-carboxaldehyde, 3,5-dimethyl-; 3-Cyclohexene-1-carboxaldehyde, 2,4-dimethyl-; 1,6-Octadien-3-ol, 3,7-dimethyl-; 1,6-Octadien-3-ol, 3,7-dimethyl-, acetate; Lilial (p-t-Bucinal), and Cyclopentanone, 2-[2-(4-methyl-3-cyclohexen-1-yl)propyl]- and 1-methyl-4-(1-methylethenyl)cyclohexene and mixtures thereof.

In one aspect, the composition may comprise an encapsulated perfume particle comprising either a water-soluble hydroxylic compound or melamine-formaldehyde or modified polyvinyl alcohol. In one aspect the encapsulate comprises (a) an at least partially water-soluble solid matrix comprising one or more water-soluble hydroxylic compounds, preferably starch; and (b) a perfume oil encapsulated by the solid matrix.

In a further aspect, the perfume may be pre-complexed with a polyamine, preferably a polyethylenimine so as to form a Schiff base.

Polymers—

The composition may comprise one or more polymers. Examples are carboxymethylcellulose, poly(vinyl-pyrrolidone), poly (ethylene glycol), poly(vinyl alcohol), poly (vinylpyridine-N-oxide), poly(vinylimidazole), polycarboxylates such as polyacrylates, maleic/acrylic acid copolymers and lauryl methacrylate/acrylic acid co-polymers.

The composition may comprise one or more amphiphilic cleaning polymers such as the compound having the following general structure: bis$((C_2H_5O)(C_2H_4O)n)(CH_3)$—$N^+$—$C_xH_{2x}$—$N^+$—$(CH_3)$-bis$((C_2H_5O)(C_2H_4O)n)$, wherein n=from 20 to 30, and x=from 3 to 8, or sulphated or sulphonated variants thereof.

The composition may comprise amphiphilic alkoxylated grease cleaning polymers which have balanced hydrophilic and hydrophobic properties such that they remove grease particles from fabrics and surfaces. Specific embodiments of the amphiphilic alkoxylated grease cleaning polymers of the present invention comprise a core structure and a plurality of alkoxylate groups attached to that core structure. These may comprise alkoxylated polyalkylenimines, preferably having an inner polyethylene oxide block and an outer polypropylene oxide block.

Alkoxylated polycarboxylates such as those prepared from polyacrylates are useful herein to provide additional grease removal performance. Such materials are described in WO91/08281 and PCT90/01815. Chemically, these materials comprise polyacrylates having one ethoxy side-chain per every 7-8 acrylate units. The side-chains are of the formula —$(CH_2CH_2O)_m$ $(CH_2)_n CH_3$ wherein m is 2-3 and n is 6-12. The side-chains are ester-linked to the polyacrylate "backbone" to provide a "comb" polymer type structure. The molecular weight can vary, but is typically in the range of 2000 to 50,000. Such alkoxylated polycarboxylates can comprise from 0.05 wt % to 10 wt % of the compositions herein.

The isoprenoid-derived surfactants of the present invention, and their mixtures with other cosurfactants and other adjunct ingredients, are particularly suited to be used with an amphilic graft co-polymer, preferably the amphilic graft co-polymer comprises (i) polyethyelene glycol backbone; and (ii) and at least one pendant moiety selected from polyvinyl acetate, polyvinyl alcohol and mixtures thereof. A preferred amphilic graft co-polymer is Sokalan HP22, supplied from BASF. Suitable polymers include random graft copolymers, preferably a polyvinyl acetate grafted polyethylene oxide copolymer having a polyethylene oxide backbone and multiple polyvinyl acetate side chains. The molecular weight of the polyethylene oxide backbone is preferably 6000 and the weight ratio of the polyethylene oxide to polyvinyl acetate is 40 to 60 and no more than 1 grafting point per 50 ethylene oxide units.

Carboxylate Polymer—

The composition of the present invention may also include one or more carboxylate polymers such as a maleate/acrylate random copolymer or polyacrylate homopolymer. In one aspect, the carboxylate polymer is a polyacrylate homopolymer having a molecular weight of from 4,000 to 9,000 Da, or from 6,000 to 9,000 Da.

Soil Release Polymer—

The composition of the present invention may also include one or more soil release polymers having a structure as defined by one of the following structures (I), (II) or (III):

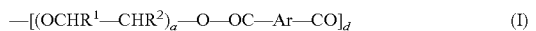  (I)

  (II)

  (III)

wherein:
a, b and c are from 1 to 200;
d, e and f are from 1 to 50;
Ar is a 1,4-substituted phenylene;
sAr is 1,3-substituted phenylene substituted in position 5 with $SO_3Me$;
Me is Li, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or mixtures thereof;
$R^1$, $R^2$, $R^3$, $R^4$, $R^5$ and $R^6$ are independently selected from H or $C_1$-$C_{18}$ n- or iso-alkyl; and
$R^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group.

Suitable soil release polymers are polyester soil release polymers such as Repel-o-tex polymers, including Repel-o-tex, SF-2 and SRP6 supplied by Rhodia. Other suitable soil release polymers include Texcare polymers, including Texcare SRA100, SRA300, SRN100, SRN170, SRN240, SRN300 and SRN325 supplied by Clariant. Other suitable soil release polymers are Marloquest polymers, such as Marloquest SL supplied by Sasol.

Cellulosic Polymer—

The composition of the present invention may also include one or more cellulosic polymers including those selected from alkyl cellulose, alkyl alkoxyalkyl cellulose, carboxyalkyl cellulose, alkyl carboxyalkyl cellulose. In one aspect, the cellulosic polymers are selected from the group comprising carboxymethyl cellulose, methyl cellulose, methyl hydroxyethyl cellulose, methyl carboxymethyl cellulose, and mixtures thereof. In one aspect, the carboxymethyl cellulose has a degree of carboxymethyl substitution from 0.5 to 0.9 and a molecular weight from 100,000 to 300,000 Da.

The compositions may be prepared in accordance with methods known in the art and may be in the form of a liquid or a dry composition. The compositions may be stabilized in accordance with methods known in the art.

Methods of Using the Variant Alpha-Amylase of the Invention—Industrial Applications The variant alpha-amylases of the present invention possess valuable properties allowing for a variety of industrial applications. In particular, the alpha-amylases may be used in ethanol production, and starch conversion processes.

Further, the alpha-amylases of the invention are particularly useful in the production of sweeteners/syrups and ethanol (see, e.g., U.S. Pat. No. 5,231,017, which is hereby incorporated by reference), such as fuel, drinking and industrial ethanol, from starch or whole grains.

In one embodiment the present invention relates to a use of the alpha-amylase according to the invention in a liquefaction process. The produced liquefact may be further processed into a syrup and/or a fermentation product.

Starch Processing

Native starch consists of microscopic granules, which are insoluble in water at room temperature. When aqueous starch slurry is heated, the granules swell and eventually burst, dispersing the starch molecules into the solution. At temperatures up to about 50° C. to 75° C. the swelling may be reversible. However, with higher temperatures an irreversible swelling called "gelatinization" begins. During this "gelatinization" process there is a dramatic increase in viscosity. Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. In dry milling whole kernels are milled and used. Wet milling gives a good separation of germ and meal (starch granules and protein) and is often applied at locations where the starch hydrolyzate is used in the production of, e.g., syrups. Both dry and wet milling is well known in the art of starch processing and may be used in a process of the invention. Methods for reducing the particle size of the starch containing material are well known to those skilled in the art.

As the solids level is 30-40% in a typical industrial process, the starch has to be thinned or "liquefied" so that it can be suitably processed. This reduction in viscosity is primarily attained by enzymatic degradation in current commercial practice.

Liquefaction is carried out in the presence of an alpha-amylase, preferably a bacterial alpha-amylase and/or acid fungal alpha-amylase. In one embodiment a protease is also present during liquefaction. In an embodiment, a phytase is also present during liquefaction. In an embodiment, viscosity reducing enzymes such as a xylanase and/or beta-glucanase is also present during liquefaction.

During liquefaction, the long-chained starch is degraded into branched and linear shorter units (maltodextrins) by an alpha-amylase. Liquefaction may be carried out as a three-step hot slurry process. The slurry is heated to between 60-95° C. (e.g., 70-90° C., such as 77-86° C., 80-85° C., 83-85° C.) and an alpha-amylase is added to initiate liquefaction (thinning).

The slurry may in an embodiment be jet-cooked at between 95-140° C., e.g., 105-125° C., for about 1-15 minutes, e.g., about 3-10 minutes, especially around 5 minutes. The slurry is then cooled to 60-95° C. and more alpha-amylase is added to obtain final hydrolysis (secondary liquefaction). The jet-cooking process is carried out at pH 4.5-6.5, typically at a pH between 5 and 6. The alpha-amylase may be added as a single dose, e.g., before jet cooking.

The liquefaction process is carried out at between 70-95° C., such as 80-90° C., such as around 85° C., for about 10 minutes to 5 hours, typically for 1-2 hours. The pH is between 4 and 7, such as between 5.5 and 6.2. In order to ensure optimal enzyme stability under these conditions, calcium may optionally be added (to provide 1-60 ppm free calcium ions, such as about 40 ppm free calcium ions). After such treatment, the liquefied starch will typically have a "dextrose equivalent" (DE) of 10-16.

Generally liquefaction and liquefaction conditions are well known in the art.

Saccharification may be carried out using conditions well-known in the art with a carbohydrate-source generating enzyme, in particular a glucoamylase, or a beta-amylase and optionally a debranching enzyme, such as an isoamylase or a pullulanase. For instance, a full saccharification step may last from about 24 to about 72 hours. However, it is common to do a pre-saccharification of typically 40-90 minutes at a temperature between 30-65° C., typically about 60° C., followed by complete saccharification during fermentation in a simultaneous saccharification and fermentation (SSF) process. Saccharification is typically carried out at a temperature in the range of 20–75° C., e.g., 25-65° C. and 40-70° C., typically around 60° C., and at a pH between about 4 and 5, normally at about pH 4.5.

The saccharification and fermentation steps may be carried out either sequentially or simultaneously. In an embodiment, saccharification and fermentation are performed simultaneously (referred to as "SSF"). However, it is common to perform a pre-saccharification step for about 30 minutes to 2 hours (e.g., 30 to 90 minutes) at a temperature of 30 to 65° C., typically around 60° C. which is followed by a complete saccharification during fermentation referred to as simultaneous saccharification and fermentation (SSF). The pH is usually between 4.2-4.8, e.g., pH 4.5. In a simultaneous saccharification and fermentation (SSF) process, there is no holding stage for saccharification, rather, the yeast and enzymes are added together.

In a typical saccharification process, maltodextrins produced during liquefaction are converted into dextrose by adding a glucoamylase and optionally a debranching enzyme, such as an isoamylase (U.S. Pat. No. 4,335,208) or a pullulanase. The temperature is lowered to 60° C., prior to the addition of the glucoamylase and debranching enzyme. The saccharification process proceeds for 24-72 hours. Prior to addition of the saccharifying enzymes, the pH is reduced to below 4.5, while maintaining a high temperature (above 95° C.), to inactivate the liquefying alpha-amylase. This process reduces the formation of short oligosaccharide called "panose precursors," which cannot be hydrolyzed properly by the debranching enzyme. Normally, about 0.2-0.5% of the saccharification product is the branched trisaccharide panose (Glc pα1-6Glc pα1-4Glc), which cannot be degraded by a pullulanase. If active amylase from the liquefaction remains present during saccharification (i.e., no denaturing), the amount of panose can be as high as 1-2%, which is highly undesirable since it lowers the saccharification yield significantly.

Other fermentation products may be fermented at conditions and temperatures well known to persons skilled in the art, suitable for the fermenting organism in question.

The fermentation product may be recovered by methods well known in the art, e.g., by distillation.

In a particular embodiment, the process of the invention further comprises, prior to the conversion of a starch-containing material to sugars/dextrins the steps of:

(x) reducing the particle size of the starch-containing material; and (y) forming a slurry comprising the starch-containing material and water.

In an embodiment, the starch-containing material is milled to reduce the particle size. In an embodiment the particle size is reduced to between 0.05-3.0 mm, preferably 0.1-0.5 mm, or so that at least 30%, preferably at least 50%, more preferably at least 70%, even more preferably at least 90% of the starch-containing material fits through a sieve with a 0.05-3.0 mm screen, preferably 0.1-0.5 mm screen.

The aqueous slurry may contain from 10-55 wt. % dry solids (DS), preferably 25-45 wt. % dry solids (DS), more preferably 30-40 wt. % dry solids (DS) of starch-containing material.

Conventional starch-conversion processes, such as liquefaction and saccharification processes are described, e.g., in U.S. Pat. No. 3,912,590, EP 252730 and EP 063909, which are incorporated herein by reference.

In an embodiment, the conversion process degrading starch to lower molecular weight carbohydrate components such as sugars or fat replacers includes a debranching step.

In the case of converting starch into a sugar, the starch is depolymerized. Such a depolymerization process consists of, e.g., a pre-treatment step and two or three consecutive process steps, i.e., a liquefaction process, a saccharification process, and depending on the desired end-product, an optional isomerization process.

When the desired final sugar product is, e.g., high fructose syrup the dextrose syrup may be converted into fructose. After the saccharification process, the pH is increased to a value in the range of 6-8, e.g., pH 7.5, and the calcium is removed by ion exchange. The dextrose syrup is then converted into high fructose syrup using, e.g., an immobilized glucose isomerase.

Production of Fermentation Products

Fermentable sugars (e.g., dextrins, monosaccharides, particularly glucose) are produced from enzymatic saccharification. These fermentable sugars may be further purified and/or converted to useful sugar products. In addition, the sugars may be used as a fermentation feedstock in a microbial fermentation process for producing end-products, such as alcohol (e.g., ethanol, and butanol), organic acids (e.g., succinic acid, 3-HP and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof).

In an embodiment, the fermentable sugars obtained during the liquefaction process steps are used to produce alcohol and particularly ethanol. In ethanol production, an SSF process is commonly used wherein the saccharifying enzymes and fermenting organisms (e.g., yeast) are added together and then carried out at a temperature of 30-40° C.

The organism used in fermentation will depend on the desired end-product. Typically, if ethanol is the desired end product yeast will be used as the fermenting organism. In some preferred embodiments, the ethanol-producing microorganism is a yeast and specifically *Saccharomyces* such as strains of *S. cerevisiae* (U.S. Pat. No. 4,316,956). A variety of *S. cerevisiae* are commercially available and these include but are not limited to FALI (Fleischmann's Yeast), SUPERSTART (Alltech), FERMIOL (DSM Specialties), RED STAR (Lesaffre) and Angel alcohol yeast (Angel Yeast Company, China), Ethanol Red (Lesaffre), Innova Drive (Novozymes A/S), Innova Lift (Novozymes A/S). The amount of starter yeast employed in the methods is an amount effective to produce a commercially significant amount of ethanol in a suitable amount of time, (e.g., to produce at least 10% ethanol from a substrate having between 25-40% DS in less than 72 hours). Yeast cells are generally supplied in amounts of about 104 to about $10^{12}$, and preferably from about $10^7$ to about $10^{10}$ viable yeast count per mL of fermentation broth. After yeast is added to the mash, it is typically subjected to fermentation for about 24-96 hours, e.g., 35-60 hours. The temperature is between about 26-34° C., typically at about 32° C., and the pH is from pH 3-6, e.g., around pH 4-5.

The fermentation may include, in addition to a fermenting microorganisms (e.g., yeast), nutrients, and additional enzymes, including phytases. The use of yeast in fermentation is well known in the art.

In further embodiments, use of appropriate fermenting microorganisms, as is known in the art, can result in fermentation end product including, e.g., glycerol, 1,3-propanediol, gluconate, 2-keto-D-gluconate, 2,5-diketo-D-gluconate, 2-keto-L-gulonic acid, succinic acid, lactic acid, amino acids, and derivatives thereof. More specifically when lactic acid is the desired end product, a *Lactobacillus* sp. (*L. casei*) may be used; when glycerol or 1,3-propanediol are the desired end-products *E. coli* may be used; and when 2-keto-D-gluconate, 2,5-diketo-D-gluconate, and 2-keto-L-gulonic acid are the desired end products, *Pantoea citrea* may be used as the fermenting microorganism. The above enumerated list are only examples and one skilled in the art will be aware of a number of fermenting microorganisms that may be used to obtain a desired end product.

Processes for Producing Fermentation Products from Gelatinized Starch-Containing Material In this aspect, the invention relates to processes for producing fermentation products, especially ethanol, from starch-containing material, which process includes a liquefaction step and sequentially or simultaneously performed saccharification and fermentation steps. Consequently, the invention relates to processes for producing fermentation products from starch-containing material comprising the steps of:

(a) liquefying starch-containing material in the presence of a variant alpha-amylase of the invention;

(b) saccharifying the liquefied material obtained in step (a) using a glucoamylase;

(c) fermenting the product of step b) using a fermenting organism.

In an embodiment, a protease, such as an acid fungal protease or a metallo protease is added before, during and/or after liquefaction. In an embodiment the metalloprotease is derived from a strain of *Thermoascus*, e.g., a strain of *Thermoascus aurantiacus*, especially *Thermoascus aurantiacus* CGMCC No. 0670. In another embodiment the protease is a bacterial protease, particularly a serine protease, more particularly an S8 protease, particularly a protease derived from a strain of *Pyrococcus*, more particularly from *Pyrococcus furiosus* disclosed in U.S. Pat. No. 6,358,726. A glucoamylase is added/is present in the saccharification step. The glucoamylase may be derived from a strain of *Aspergillus*, e.g., *Aspergillus niger* or *Aspergillus awamori*, a strain of *Talaromyces*, especially *Talaromyces emersonii*; or a strain of *Athelia*, especially *Athelia rofsii*; a strain of *Trametes*, e.g., *Trametes cingulata*; a strain of *Gloeophyllum*, especially *Gloeophyllum trabeum* or *Gloeophyllum sepiarium*; or a mixture thereof. Other suitable glucoamy-lases may also be used, see section on "Glucoamylase Present And/Or Added In Saccharification And/Or Fermentation".

Saccharification step (b) and fermentation step (c) may be carried out either sequentially or simultaneously. A pullulanase and/or protease may be added during saccharification and/or fermentation when the process is carried out as a sequential saccharification and fermentation process and before or during fermentation when steps (b) and (c) are carried out simultaneously (SSF process). The pullulanase and/or protease may also advantageously be added before liquefaction (pre-liquefaction treatment), i.e., before or during step (a), and/or after liquefaction (post liquefaction treatment), i.e., after step (a). The pullulanase is most advantageously added before or during liquefaction, i.e., before or during step (a). The fermentation product, such as especially ethanol, may optionally be recovered after fermentation, e.g., by distillation. The fermenting organism is preferably yeast, preferably a strain of *Saccharomyces cerevisiae*. In a preferred embodiment, the yeast is expressing the variant glucoamylase of the invention. In a particular embodiment, the process of the invention further comprises, prior to step (a), the steps of:

x) reducing the particle size of the starch-containing material, preferably by milling (e.g., using a hammer mill);

y) forming a slurry comprising the starch-containing material and water.

In an embodiment, the particle size is smaller than a #7 screen, e.g., a #6 screen. A #7 screen is usually used in conventional prior art processes. The aqueous slurry may contain from 10-55, e.g., 25-45 and 30-40, w/w % dry solids (DS) of starch-containing material. The slurry is heated to above the gelatinization temperature and an alpha-amylase variant may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C. at pH 4-6, preferably 4.5-5.5, and alpha-amylase variant, optionally together with a pullulanase and/or protease, preferably metalloprotease, are added to initiate liquefaction (thinning). In an embodiment the slurry may then be jet-cooked at a temperature between 95-140° C., preferably 100-135° C., such as 105-125° C., for about 1-15 minutes, preferably for about 3-10 minutes, especially around about 5 minutes. The slurry is cooled to 60-95° C. and more alpha-amylase and optionally pullulanase and/or protease, is(are) added to finalize hydrolysis (secondary liquefaction). The liquefaction process is usually carried out at pH 4.0-6, in particular at a pH from 4.5 to 5.5. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 20-75° C., preferably from 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

Processes for Producing Syrup from Geleatinized Starch-Containing Material

In this aspect the fermentation step is left out, however, conditions are generally as described above for "Processes for producing fermentation products from gelatinized starch-containing material". Thus in this aspect the present invention relates to a process for producing a syrup from starch-containing material comprising the steps of:

a) liquefying the starch-containing material at a temperature above the initial gelatinization temperature in the presence of a variant alpha-amylase of the invention or a composition of the invention; and b) saccharifying the produce of Step a) in the Presence of a Glucoamylase.

In one embodiment step b) is performed in the presence of a glucoamylase and:
i) a fungal alpha-amylase;
ii) an isoamylase;
iii) a fungal alpha-amylase and an isoamylase.

In a particularly embodiment a pullulanase is present in step a) and/or b).

Protease Present and/or Added During Liquefaction

According to the invention a thermostable protease may in one embodiment be present and/or added during liquefaction together with an alpha-amylase, such as a thermostable alpha-amylase, and optionally a carbohydrate-source generating enzyme, in particular a thermostable glucoamylase or thermostable pullulanase.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

There are no limitations on the origin of the protease used in a process of the invention as long as it fulfills the thermostability properties defined below.

The protease may be a variant of, e.g., a wild-type protease as long as the protease has the thermostability properties defined herein.

In an embodiment the protease has a thermostability above 60%, such as above 90%, such as above 100%, such as above 110% at 85° C. as determined using the Zein-BCA assay.

In an embodiment protease has a thermostability between 60-120, such as between 70-120%, such as between 80-120%, such as between 90-120%, such as between 100-120%, such as 110-120% at 85° C. as determined using the Zein-BCA assay.

In one embodiment the thermostable protease is a variant of a metallo protease as defined above.

In an embodiment the thermostable protease used in a process of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In an embodiment the thermostable protease is a variant of the mature part of the metallo protease shown in SEQ ID NO: 2 disclosed in WO 2003/048353 or the mature part of SEQ ID NO: 1 in WO 2010/008841 and shown as SEQ ID NO: 20 herein further with mutations selected from below list:

S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L;
D79L+S87P+D142L.

In an preferred embodiment the thermostable protease is a variant of the metallo protease disclosed as the mature part of SEQ ID NO: 2 disclosed in WO 2003/048353 or the mature part of SEQ ID NO: 1 in WO 2010/008841 or SEQ ID NO: 20 herein with the following mutations:
D79L+S87P+A112P+D142L;
D79L+S87P+D142L; or
A27K+D79L+Y82F+S87G+D104P+A112P+A126V+D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 20 herein.

The thermostable protease may also be derived from a bacterium, particularly an S8 protease, more particularly an S8 protease from *Pyrococcus* sp or *Thermococcus* sp.

In an embodiment the thermostable protease is derived from a strain of the bacterium *Pyrococcus*, such as a strain of *Pyrococcus furiosus* (pfu protease).

In an embodiment the protease is one shown as SEQ ID NO: 1 in U.S. Pat. No. 6,358,726-E1 (Takara Shuzo Company) and SEQ ID NO: 19 herein.

In another embodiment the thermostable protease is one disclosed in SEQ ID NO: 19 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-E1 or SEQ ID NO: 19 herein.

Glucoamylase Present and/or Added in Liquefaction

In an embodiment a glucoamylase is present and/or added in liquefaction step a) in a process of the invention (i.e., oil recovery process and fermentation product production process).

In a preferred embodiment the glucoamylase present and/or added in liquefaction step a) is derived from a strain of the genus *Penicillium*, especially a strain of *Penicillium oxalicum* disclosed as SEQ ID NO: 2 in WO 2011/127802 or SEQ ID NO: 21 herein.

In an embodiment the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NO: 21 herein.

In a preferred embodiment the glucoamylase is a variant of the *Penicillium oxalicum* glucoamylase shown in SEQ ID NO: 2 in WO 2011/127802 or SEQ ID NO: 21 herein having a K79V substitution (using the mature sequence shown in SEQ ID NO: 21 for numbering), such as a variant disclosed in WO 2013/053801.

In an embodiment the *Penicillium oxalicum* glucoamylase has a K79V substitution (using SEQ ID NO: 21 for numbering) and preferably further one of the following substitutions:
T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*;
E501V+Y504T; or
T65A+K161S; or
T65A+Q405T; or
T65A+Q327W; or
T65A+Q327F; or
T65A+Q327Y; or
P11F+T65A+Q327F; or
R1K+D3W+K5Q+G7V+N8S+T10K+P11S+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
R1E+D3N+P4G+G6R+G7A+N8A+T10D+P11D+T65A+Q327F; or
P11F+T65A+Q327W; or
P2N+P4S+P11F+T65A+Q327F+E501V+Y504T; or
P11F+T65A+Q327W+E501V+Y504T; or
T65A+Q327F+E501V+Y504T; or
T65A+S105P+Q327W; or
T65A+S105P+Q327F; or
T65A+Q327W+S364P; or
T65A+Q327F+S364P; or
T65A+S103N+Q327F; or
P2N+P4S+P11F+K34Y+T65A+Q327F; or
P2N+P4S+P11F+T65A+Q327F+D445N+V447S; or
P2N+P4S+P11F+T65A+I172V+Q327F; or
P2N+P4S+P11F+T65A+Q327F+N502*; or
P2N+P4S+P11F+T65A+Q327F+N502T+P563S+K571E; or
P2N+P4S+P11F+R31S+K33V+T65A+Q327F+N564D+K571S; or
P2N+P4S+P11F+T65A+Q327F+S377T; or
P2N+P4S+P11F+T65A+V325T+Q327W; or
P2N+P4S+P11F+T65A+Q327F+D445N+V447S+E501V+Y504T; or
P2N+P4S+P11F+T65A+I172V+Q327F+E501V+Y504T; or
P2N+P4S+P11F+T65A+Q327F+S377T+E501V+Y504T; or
P2N+P4S+P11F+D26N+K34Y+T65A+Q327F; or
P2N+P4S+P11F+T65A+Q327F+I375A+E501V+Y504T; or
P2N+P4S+P11F+T65A+K218A+K221D+Q327F+E501V+Y504T; or
P2N+P4S+P11F+T65A+S103N+Q327F+E501V+Y504T; or
P2N+P4S+T10D+T65A+Q327F+E501V+Y504T; or
P2N+P4S+F12Y+T65A+Q327F+E501V+Y504T; or
K5A+P11F+T65A+Q327F+E501V+Y504T; or
P2N+P4S+T10E+E18N+T65A+Q327F+E501V+Y504T; or
P2N+T10E+E18N+T65A+Q327F+E501V+Y504T; or P2N+P4S+P11F+T65A+Q327F+E501V+Y504T+T568N; or
P2N+P4S+P11F+T65A+Q327F+E501V+Y504T+K524T+ G526A; or
P2N+P4S+P11F+K34Y+T65A+Q327F+D445N+V447S+ E501V+Y504T; or
P2N+P4S+P11F+R31S+K33V+T65A+Q327F+D445N+ V447S+E501V+Y504T; or
P2N+P4S+P11F+D26N+K34Y+T65A+Q327F+E501V+ Y504T; or
P2N+P4S+P11F+T65A+F80*+Q327F+E501V+Y504T; or
P2N+P4S+P11F+T65A+K112S+Q327F+E501V+Y504T; or
P2N+P4S+P11F+T65A+Q327F+E501V+Y504T+T516P+ K524T+G526A; or
P2N+P4S+P11F+T65A+Q327F+E501V+N502T+Y504*; or
P2N+P4S+P11F+T65A+Q327F+E501V+Y504T; or
P2N+P4S+P11F+T65A+S103N+Q327F+E501V+Y504T; or
K5A+P11F+T65A+Q327F+E501V+Y504T; or
P2N+P4S+P11F+T65A+Q327F+E501V+Y504T+T516P+ K524T+G526A; or
P2N+P4S+P11F+T65A+K79A+Q327F+E501V+Y504T; or
P2N+P4S+P11F+T65A+K79G+Q327F+E501V+Y504T; or
P2N+P4S+P11F+T65A+K79I+Q327F+E501V+Y504T; or
P2N+P4S+P11F+T65A+K79L+Q327F+E501V+Y504T; or
P2N+P4S+P11F+T65A+K79S+Q327F+E501V+Y504T; or
P2N+P4S+P11F+T65A+L72V+Q327F+E501V+Y504T; or
S255N+Q327F+E501V+Y504T; or
P2N+P4S+P11F+T65A+E74N+V79K+Q327F+E501V+ Y504T; or
P2N+P4S+P11F+T65A+G220N+Q327F+E501V+Y504T; or
P2N+P4S+P11F+T65A+Y245N+Q327F+E501V+Y504T; or
P2N+P4S+P11F+T65A+Q253N+Q327F+E501V+Y504T; or
P2N+P4S+P11F+T65A+D279N+Q327F+E501V+Y504T; or
P2N+P4S+P11F+T65A+Q327F+S359N+E501V+Y504T; or
P2N+P4S+P11F+T65A+Q327F+D370N+E501V+Y504T; or
P2N+P4S+P11F+T65A+Q327F+V460S+E501V+Y504T; or
P2N+P4S+P11F+T65A+Q327F+V460T+P468T+E501V+ Y504T; or
P2N+P4S+P11F+T65A+Q327F+T463N+E501V+Y504T; or
P2N+P4S+P11F+T65A+Q327F+S465N+E501V+Y504T; or
P2N+P4S+P11F+T65A+Q327F+T477N+E501V+Y504T.

In a preferred embodiment the glucoamylase present and/or added in liquefaction is the *Penicillium oxalicum* glucoamylase having a K79V substitution and preferably further one of the following substitutions:
P11F+T65A+Q327F;
P2N+P4S+P11F+T65A+Q327F (using SEQ ID NO: 21 for numbering).

In an embodiment the glucoamylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 21 herein.

The glucoamylase may be added in amounts from 0.1-100 micro grams EP/g, such as 0.5-50 micro grams EP/g, such as 1-25 micrograms EP/g, such as 2-12 micrograms EP/g DS.

Glucoamylase Present and/or Added in Saccharification and/or Fermentation

A glucoamylase is present and/or added in saccharification and/or fermentation, preferably simultaneous saccharification and fermentation (SSF), in a process of the invention (i.e., oil recovery process and fermentation product production process).

In an embodiment the glucoamylase present and/or added in saccharification and/or fermentation is of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *T. emersonii* or a strain of *Trametes*, preferably *T. cingulata*, or a strain of *Pycnoporus*, or a strain of *Gloeophyllum*, such as *G. sepiarium* or *G. trabeum*, or a strain of the *Nigrofomes*.

In an embodiment the glucoamylase is derived from *Talaromyces*, such as a strain of *Talaromyces emersonii*, such as the one shown in SEQ ID NO: 22 herein, In an embodiment the glucoamylase is selected from the group consisting of:
(i) a glucoamylase comprising the polypeptide of SEQ ID NO: 22 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 22 herein.

In an embodiment the glucoamylase is derived from a strain of the genus *Pycnoporus*, in particular a strain of *Pycnoporus sanguineus* described in WO 2011/066576 (SEQ ID NOs 2, 4 or 6), such as the one shown as SEQ ID NO: 4 in WO 2011/066576, or SEQ ID NO: 23 herein.

In an embodiment the glucoamylase is selected from the group consisting of:
(i) a glucoamylase comprising the polypeptide of SEQ ID NO: 23 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 23 herein.

In an embodiment the glucoamylase is derived from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is the *Gloeophyllum sepiarium* shown in SEQ ID NO: 2 in WO 2011/068803 or SEQ ID NO: 24 herein.

In a preferred embodiment the glucoamylase is derived from *Gloeophyllum serpiarium*, such as the one shown in SEQ ID NO: 24 herein. In an embodiment the glucoamylase is selected from the group consisting of:
(i) a glucoamylase comprising the polypeptide of SEQ ID NO: 24 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 24 herein.

In another embodiment the glucoamylase is derived from *Gloeophyllum trabeum* such as the one shown in SEQ ID NO: 25 herein. In an embodiment the glucoamylase is selected from the group consisting of:

(i) a glucoamylase comprising the polypeptide of SEQ ID NO: 25 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 25 herein.

In an embodiment the glucoamylase is derived from a strain of the genus Nigrofomes, in particular a strain of Nigrofomes sp. disclosed in WO 2012/064351.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL and AMG™ E (from Novozymes A/S); OPTIDEX™ 300, GC480, GC417 (from DuPont.); AMIGASE™ and AMIGASE™ PLUS (from DSM); G-ZYME™ G900, G-ZYME™ and G990 ZR (from DuPont).

According to a preferred embodiment of the invention the glucoamylase is present and/or added in saccharification and/or fermentation in combination with an alpha-amylase. Examples of suitable alpha-amylase are described below.

Alpha-Amylase Present and/or Added In Saccharification And/Or Fermentation

In an embodiment an alpha-amylase is present and/or added in saccharification and/or fermentation in a process of the invention. In a preferred embodiment the alpha-amylase is of fungal or bacterial origin. In a preferred embodiment the alpha-amylase is a fungal acid stable alpha-amylase. A fungal acid stable alpha-amylase is an alpha-amylase that has activity in the pH range of 3.0 to 7.0 and preferably in the pH range from 3.5 to 6.5, including activity at a pH of about 4.0, 4.5, 5.0, 5.5, and 6.0.

In a preferred embodiment the alpha-amylase present and/or added in saccharification and/or fermentation is derived from a strain of the genus *Rhizomucor*, preferably a strain the *Rhizomucor pusillus*, such as one shown in SEQ ID NO: 3 in WO 2013/006756, such as a *Rhizomucor pusillus* alpha-amylase hybrid having an *Aspergillus niger* linker and starch-binding domain, such as the one shown in SEQ ID NO: 26 herein, or a variant thereof.

In an embodiment the alpha-amylase present and/or added in saccharification and/or fermentation is selected from the group consisting of:

(i) an alpha-amylase comprising the polypeptide of SEQ ID NO: 26 herein;

(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 26 herein.

In a preferred embodiment the alpha-amylase is a variant of the alpha-amylase shown in SEQ ID NO: 26 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 26 for numbering).

In an embodiment the alpha-amylase is derived from a *Rhizomucor pusillus* with an *Aspergillus niger* glucoamylase linker and starch-binding domain (SBD), preferably disclosed as SEQ ID NO: 26 herein, preferably having one or more of the following substitutions: G128D, D143N, preferably G128D+D143N (using SEQ ID NO: 19 for numbering).

In an embodiment the alpha-amylase variant present and/or added in saccharification and/or fermentation has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 26 herein.

In a preferred embodiment the ratio between glucoamylase and alpha-amylase present and/or added during saccharification and/or fermentation may preferably be in the range from 500:1 to 1:1, such as from 250:1 to 1:1, such as from 100:1 to 1:1, such as from 100:2 to 100:50, such as from 100:3 to 100:70.

Pullulanase Present and/or Added in Liquefaction and/or Saccharification and/or Fermentation.

A pullulanase may be present and/or added during liquefaction step a) and/or saccharification step b) or fermentation step c) or simultaneous saccharification and fermentation.

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

Contemplated pullulanases according to the present invention include the pullulanases from *Bacillus amyloderamificans* disclosed in U.S. Pat. No. 4,560,651 (hereby incorporated by reference), the pullulanase disclosed as SEQ ID NO: 2 in WO 01/51620 (hereby incorporated by reference), the *Bacillus deramificans* disclosed as SEQ ID NO: 4 in WO 01/51620 (hereby incorporated by reference), and the pullulanase from *Bacillus acidopullulyticus* disclosed as SEQ ID NO: 6 in WO 01/51620 (hereby incorporated by reference) and also described in FEMS Mic. Let. (1994) 115, 97-106.

The pullulanase may according to the invention be added in an effective amount which include the preferred amount of about 0.0001-10 mg enzyme protein per gram DS, preferably 0.0001-0.10 mg enzyme protein per gram DS, more preferably 0.0001-0.010 mg enzyme protein per gram DS. Pullulanase activity may be determined as NPUN. An Assay for determination of NPUN is described in the "Materials & Methods"-section below.

Suitable commercially available pullulanase products include PROMOZYME D, PROMOZYME™ D2 (Novozymes A/S, Denmark), OPTIMAX L-300 (Genencor Int., USA), and AMANO 8 (Amano, Japan).

The fermentation product, such as especially ethanol, may optionally be recovered after fermentation, e.g., by distillation. Suitable starch-containing starting materials are listed in the section "Starch-Containing Materials"-section below. In an embodiment the starch-containing materials is corn or wheat.

The fermenting organism is preferably yeast, preferably a strain of *Saccharomyces*, especially a strain of *Saccharomyces cerevisae*. Suitable fermenting organisms are listed in the "Fermenting Organisms"-section above. In a preferred embodiment steps ii) and iii) are carried out sequentially or simultaneously (i.e., as SSF process).The aqueous slurry may contain from 10-55 wt.-% dry solids, preferably 25-45 wt.-% dry solids, more preferably 30-40 wt.-% dry solids of starch-containing material. The slurry is heated to above the initial gelatinization temperature. Alpha-amylase, preferably bacterial alpha-amylase, may be added to the slurry. In an embodiment the slurry is also jet-cooked to further gelatinize the slurry before being subjected to an alpha-amylase in liquefaction step i).

The temperature during step (i) is above the initial gelatinization temperature, such as between 80-90° C., such as around 85° C.

In an embodiment liquefaction is carried out as a three-step hot slurry process. The slurry is heated to between 60-95° C., preferably between 80-90° C., and alpha-amylase is added to initiate liquefaction (thinning). Then the slurry is jet-cooked at a temperature between 95-140° C., preferably 105-125° C., for 1-15 minutes, preferably for 3-10 minutes, especially around 5 minutes. The slurry is cooled to 60-95° C., preferably 80-90° C., and more alpha-amylase is added to finalize hydrolysis (secondary liquefaction). The liquefaction process is usually carried out at pH 4.5-6.5, such as around 4.8, or a pH between 5.0-6.2, such as 5.0-6.0, such as between 5.0-5.5, such as around 5.2, such as around 5.4, such as around 5.6, such as around 5.8. Milled and liquefied starch is known as "mash".

The saccharification in step ii) may be carried out using conditions well known in the art. For instance, a full saccharification process may last up to from about 24 to about 72 hours. In an embodiment a pre-saccharification step is done at 40-90 minutes at a temperature between 30-65° C., typically at about 60° C., followed by complete saccharification during fermentation in a simultaneous saccharification and fermentation step (SSF). Saccharification is typically carried out at temperatures from 30-70° C., such as 55-65° C., typically around 60° C., and at a pH between 4 and 5, normally at about pH 4.5.

The most widely used process in fermentation product production, especially ethanol production, is simultaneous saccharification and fermentation (SSF) process, in which there is no holding stage for the saccharification.

SSF may typically be carried out at a temperature between 25° C. and 40° C., such as between 28° C. and 36° C., such as between 30° C. and 34° C., such as around 32° C., when the fermentation organism is yeast, such as a strain of *Saccharomyces cerevisiae*, and the desired fermentation product is ethanol. In an embodiment fermentation is ongoing for 6 to 120 hours, in particular 24 to 96 hours.

Other fermentation products may be fermented at conditions and temperatures, well known to the skilled person in the art, suitable for the fermenting organism in question.

Fermentation Medium

The environment in which fermentation is carried out is often referred to as the "fermentation media" or "fermentation medium". The fermentation medium includes the fermentation substrate, that is, the carbohydrate source that is metabolized by the fermenting organism. According to the invention the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

The term "fermenting organism" refers to any organism, including bacterial and fungal organisms, especially yeast, suitable for use in a fermentation process and capable of producing the desired fermentation product. Especially suitable fermenting organisms are able to ferment, i.e., convert, sugars, such as glucose or maltose, directly or indirectly into the desired fermentation product, such as ethanol. Examples of fermenting organisms include fungal organisms, such as yeast. Preferred yeast includes strains of *Saccharomyces* spp., in particular, *Saccharomyces cerevisiae*. Suitable concentrations of the viable fermenting organism during fermentation, such as SSF, are well known in the art or can easily be determined by the skilled person in the art. In one embodiment the fermenting organism, such as ethanol fermenting yeast, (e.g., *Saccharomyces cerevisiae*) is added to the fermentation medium so that the viable fermenting organism, such as yeast, count per mL of fermentation medium is in the range from $10^5$ to $10^{12}$, preferably from 107 to $10^{10}$, especially about $5 \times 10^7$.

Examples of commercially available yeast includes, e.g., RED STAR™ and ETHANOL RED™ yeast (available from Fermentis/Lesaffre, USA), FALI (available from Fleischmann's Yeast, USA), SUPERSTART and THERMO-SACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), FERMIOL (available from DSM Specialties), Innova® Drive (Novozymes A/S), Innova® Lift (Novozymes A/S).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived therefrom, or cereals. Contemplated are also waxy and non-waxy types of corn and barley. In a preferred embodiment the starch-containing material, used for ethanol production according to the invention, is corn or wheat.

Fermentation Products

The term "fermentation product" means a product produced by a process including a fermentation step using a fermenting organism. Fermentation products contemplated according to the invention include alcohols (e.g., ethanol, methanol, butanol; polyols such as glycerol, sorbitol and inositol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferably processes of the invention are used for producing an alcohol, such as ethanol. The fermentation product, such as ethanol, obtained according to the invention, may be used as fuel, which is typically blended with gasoline. However, in the case of ethanol it may also be used as potable ethanol.

Recovery of Fermentation Products

Subsequent to fermentation, or SSF, the fermentation product may be separated from the fermentation medium. The slurry may be distilled to extract the desired fermentation product (e.g., ethanol). Alternatively the desired fermentation product may be extracted from the fermentation medium by micro or membrane filtration techniques. The fermentation product may also be recovered by stripping or other method well known in the art.

The invention is further illustrated in the following numbered embodiments.

Embodiment 1

An alpha-amylase variant comprising a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, wherein the variant has at least 60%, at least 65%, at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10,SEQ ID NO: 11,SEQ ID NO: 12,SEQ ID NO: 13,SEQ ID NO: 14, SEQ ID NO: 15, SEQ ID NO: 16, SEQ ID NO: 17, SEQ ID NO: 18, and SEQ ID NO: 27.

Embodiment 2

The variant alpha-amylase according to embodiment 1, wherein the variant has increased thermo-stability at pH 4.5 over the parent alpha-amylase.

Embodiment 3

The variant according to embodiment 1, wherein the variant has increased chelator stability in model detergent A over the parent alpha-amylase.

Embodiment 4

The variant according to embodiment 1, wherein the variant is capable of generating a liquefact having a dextrose equivalent (DE) value higher than the DE value generated by a parent alpha-amylase.

Embodiment 5

The variants according to embodiment 1, wherein the variant is capable of generating a liquefact having decreased viscosity compared to the liquefact generated by a parent alpha-amylase.

Embodiment 6

The variant alpha-amylase according to embodiment 1, wherein the variant has increased thermo-stability at pH 4.5, particularly increased stability determined as an improvement factor (IF) over the parent alpha-amylase, wherein the IF is determined as residual activity of the variant alpha-amylase (ratio of activity in a themo-stressed sample over activity in a sample incubated at 4° C.) over residual activity of the parent alpha-amylase (ratio of activity in a themo-stressed sample over activity in a sample incubated at 4° C.), in particular the variant has an IF of at least 1.1, at least 1.2, at least 1.3, at least 1.4, at least 1.5, at least 1.6, at least 1.7, at least 1.8, at least 1.9, at least 2.0.

Embodiment 7

The variant according to embodiment 1, wherein the variant has increased chelator stability in model detergent A, particularly increased stability determined as an improvement factor (IF) over the parent alpha-amylase, wherein the IF is determined as residual activity (ratio of activity in a themo-stressed sample over activity in a sample incubated at 4° C.) of the variant over residual activity (ratio of activity in a themo-stressed sample over activity in a sample incubated at 4° C.) of the parent alpha-amylase, in particular the variants have an IF of at least 1.1, at least 1.2, at least 1.3, at least 1.4, at least 1.5, at least 1.6, at least 1.7, at least 1.8, at least 1.9, at least 2.0.

Embodiment 8

The variant according to any of the preceding embodiments wherein the variant further comprises a deletion of two amino acids in the region corresponding to positions 179-182 using SEQ ID NO: 1 for numbering.

Embodiment 9

The variant according to embodiment 8, wherein the deletion is selected from the group consisting of 179*+180*, 179*+181*, 179*+182*, 180*+181*, 180*+182*, and 181*+182*, particularly 181*+182*.

Embodiment 10

The variant according to any of embodiments 1-9, wherein the parent alpha-amylase is SEQ ID NO: 3 and, wherein the variant comprises the specific substitutions corresponding to:

G48A+T49I+H68W+G107A+H156Y+A181T+A209V+Q264S+K176L+F201Y+H205Y+K213T+E255P+Q360S+D416V+R437W using SEQ ID NO: 2 for numbering; or G48A+T49I+H68W+G107A+T116Q+H156Y+A181T+A209V+Q264S+K176L+F201Y+H205Y+K213T+E255P+Q360S+D416V+R437W using SEQ ID NO: 2 for numbering; and wherein the variant has at least 75%, at least 80%, at least 85%, at least 90%, at least 95%, at least 96%, at least 97%, at least 98%, or at least 99%, but less than 100% sequence identity to SEQ ID NO: 3.

Embodiment 11

The variant of embodiment 10, further comprising N190F using SEQ ID NO: 2 for numbering.

Embodiment 12

The variant according to any of embodiments 1-9, wherein the parent alpha-amylase is SEQ ID NO: 1 and, wherein the variant further comprises the specific substitutions corresponding to:
V59A+E129V+E177L+R179E+Q254S+M284V+
V212T+Y268G+N293Y+T297N, and optionally a deletion of two amino acids in the region corresponding to positions 179-182, particularly 181*+182*using SEQ ID NO: 1 for numbering, and wherein the variant has at least 75%, at least 80%, at least 85%, at least 90%, at least 95%, at least 96%, at least 97%, at least 98%, or at least 99%, but less than 100% sequence identity to SEQ ID NO: 1.

Embodiment 13

The variant according to embodiment 12, further comprising N193F using SEQ ID NO: 1 for numbering.

Embodiment 14

The variant according to any of the preceeding embodiments comprising a substitution at a position corresponding to position 188 and further substitutions at positions corresponding to positions 242 and 279, particularly the specific combinations selected from:
E188P+S242Y+K279I;
E188P+S242L+K279W;
E188P+S242P+K279W;
E188P+S242L+K279I;
E188P+S242Y+K279W;
E188P+S242Y+K279F;
E188P+S242Y+K279H;
E188P+S242Y+K279L;
E188P+S242Y+K279Y;
E188P+S242P+K279;
E188P+S242F+K279W;
E188P+S242H+K279W;
E188P+S242W+K279W.

Embodiment 15

The variant of embodiment 1, further comprising a substitution corresponding to I204Y using SEQ ID NO: 1 for numbering, particularly the specific combinations selected from:
E188P+I204Y+S242Y;
E188P+I204Y+S242F;
E188P+I204Y+K279W;
E188P+I204Y+K279Y;
E188P+I204Y+K279F;
E188P+I204Y+K279H;
E188P+I204Y+K279I;
E188P+I204Y+K279L.

Embodiment 16

The variant of any of embodiments 1-15, wherein the variant alpha-amylase is isolated.

Embodiment 17

The variant of any of embodiments 1-16, wherein the number of alterations is 1-20, e.g., 1-10 and 1-5, such as 1, 2, 3, 4, 5, 6, 7, 8, 9 or 10 alterations.

Embodiment 18

A composition comprising the variant alpha-amylase of any of the embodiments 1-17.

Embodiment 19

The composition of embodiment 18, further comprising a surfactant.

Embodiment 20

The composition of any of embodiments 18 or 19, wherein the composition comprises a surfactant or surfactant system wherein the surfactant can be selected from nonionic surfactants, anionic surfactants, cationic surfactants, ampholytic surfactants, zwitterionic surfactants, semi-polar nonionic surfactants and mixtures thereof.

Embodiment 21

The composition of embodiment 20, wherein the composition comprises an anionic surfactant, in particular linear alkylbenzene sulfonate (LAS) and/or alcohol ethoxysulfate (AEOS).

Embodiment 22

The composition of embodiment 20, wherein the composition comprises a nonionic surfactant, such as alcohol ethoxylate (AEO).

Embodiment 23

The composition of any of embodiments 19-22, wherein the composition comprises one or more anionic and/or one or more nonionic surfactants.

Embodiment 24

The composition of any of embodiments 18-23, wherein the composition comprises one or more of surfactants, in particular linear alkylbenzenesulfonic acid (LAS), sodium laureth sulfate (SLES) and/or alcohol ethoxylate (AEO).

Embodiment 25

The composition according to embodiment 18, further comprising a protease, particularly an S8 protease, more particularly an S8 protease from *Pyrococcus* or *Thermococcus*.

Embodiment 26

The composition of embodiment 25, wherein the protease has at least 75%, at least 80%, at least 85%, at least 90%, at least 95%, at least 96%, at least 97%, at least 98%, at least 99%, or 100% sequence identity to SEQ ID NO: 19.

Embodiment 27

A polynucleotide encoding the variant of any of embodiments 1-17.

Embodiment 28

A nucleic acid construct comprising the polynucleotide of embodiment 27.

Embodiment 29

An expression vector comprising the polynucleotide of embodiment 27.

Embodiment 30

A host cell comprising the polynucleotide of embodiment 27.

Embodiment 31

A method of producing an alpha-amylase variant of embodiments 1-17, comprising:
a) cultivating the host cell of embodiment 30 under conditions suitable for expression of the variant; and
b) optionally recovering the variant.

Embodiment 32

A use of the variant of embodiments 1-17 or the composition according to embodiments 18 or 25-26 for liquefying a starch-containing material.

Embodiment 33

A use of the variant of embodiments 1-17 in a detergent.

Embodiment 34

A process for producing a syrup from starch-containing material comprising the steps of:
a) liquefying the starch-containing material at a temperature above the initial gelatinization temperature in the presence of a variant alpha-amylase according to embodiment 1-17 or a composition of embodiment 18 or 25-26; and
b) saccharifying the produce of step a) in the presence of a glucoamylase.

Embodiment 35

The process according to embodiment 34, wherein step b) is performed in the presence of a glucoamylase and:
i) a fungal alpha-amylase;
ii) an isoamylase; or
iii) a fungal alpha-amylase and an isoamylase.

Embodiment 36

The process according to embodiments 34-35, wherein a pullulanase is present in step a) and/or b).

Embodiment 37

The process according to any of embodiments 34-36 further comprising: c) fermenting the product of step b) using a fermenting organism to produce a fermentation product.

Embodiment 38

The process of embodiment 37, wherein the fermenting organism is a yeast and the fermentation product is alcohol.

Embodiment 39

The process of embodiment 38, wherein the yeast is *Saccharomyces cerevisiae* and the alcohol is ethanol.

Embodiment 40

The process of embodiment 37, wherein steps b) and c) are performed simultaneously.

Embodiment 41

A method for increasing stability of a parent alpha-amylase comprising introducing a substitution at a position corresponding to position 188 and at least one further substitution at a position corresponding to position 242 or 279 or 275 of SEQ ID NO: 1, in particular one or more combinations of substitutions selected from the group consisting of E188P+S242Y, E188P+S242F, E188P+S242H, E188P+S242W, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H.

Embodiment 42

The method of embodiment 41, wherein the variant has at least 60%, at least 65%, at least 70%, at least 75%, at least 80%, at least 85%, at least 90%, at least 95%, at least 96%, at least 97%, at least 98%, or at least 99%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10,SEQ ID NO: 11,SEQ ID NO: 12,SEQ ID NO: 13,SEQ ID NO: 14,SEQ ID NO: 15, SEQ ID NO: 16, SEQ ID NO: 17, SEQ ID NO: 18.

Embodiment 43

The method according to any of embodiments 41-42, wherein the variants have increased thermo-stability at pH 4.5 over the parent alpha-amylase.

Embodiment 44

The method according to any of embodiments 41-42, wherein the variants have increased chelator stability in model detergent A over the parent alpha-amylase.

The present invention is further described by the following examples that should not be construed as limiting the scope of the invention.

EXAMPLES

Methods & Reagents
Assays for Alpha-Amylase Activity
pNP-G7 Assay

The alpha-amylase activity may be determined by a method employing the G7-pNP substrate. G7-pNP which is an abbreviation for 4,6-ethylidene(G7)-p-nitrophenyl(G1)-α,D-maltoheptaoside, a blocked oligosaccharide which can be cleaved by an endo-amylase, such as an alpha-amylase. Following the cleavage, the alpha-Glucosidase included in the kit digest the hydrolysed substrate further to liberate a free PNP molecule which has a yellow color and thus can be measured by visible spectophometry at λ=405 nm (400-420 nm.). Kits containing G7-pNP substrate and alpha-Glucosidase is manufactured by Roche/Hitachi (cat. No. 11876473).
Reagents:

The G7-pNP substrate from this kit contains 22 mM 4,6-ethylidene-G7-pNP and 52.4 mM HEPES (2-[4-(2-hydroxyethyl)-1-piperazinyl]-ethanesulfonic acid), pH 7.0).

The alpha-Glucosidase reagent contains 52.4 mM HEPES, 87 mM NaCl, 12.6 mM MgCl2, 0.075 mM CaCl2, >4 kU/L alpha-glucosidase).

The substrate working solution is made by mixing 1 mL of the alpha-Glucosidase reagent with 0.2 mL of the G7-pNP substrate. This substrate working solution is made immediately before use.

Dilution buffer: 50 mM MOPS, 0.05% (w/v) Triton X100 (polyethylene glycol p-(1,1,3,3-tetramethylbutyl)-phenyl ether (C14H22O(C2H4O)n (n=9-10))), 1 mM CaCl2, pH 8.0.
Procedure:

The amylase sample to be analyzed is diluted in dilution buffer to ensure the pH in the diluted sample is 7. The assay is performed by transferring 20 µl diluted enzyme samples to 96 well microtiter plate and adding 80 µl substrate working solution. The solution is mixed and pre-incubated 1 minute at room temperature and absorption is measured every 20 sec. over 5 minutes at OD 405 nm.

The slope (absorbance per minute) of the time dependent absorption-curve is directly proportional to the specific activity (activity per mg enzyme) of the alpha-amylase in question under the given set of conditions. The amylase sample should be diluted to a level where the slope is below 0.4 absorbance units per minute.
Phadebas Activity Assay:

The alpha-amylase activity may also be determined by a method using the Phadebas substrate (from for example Magle Life Sciences, Lund, Sweden). A Phadebas tablet includes interlinked starch polymers that are in the form of globular microspheres that are insoluble in water. A blue dye is covalently bound to these microspheres. The interlinked starch polymers in the microsphere are degraded at a speed that is proportional to the alpha-amylase activity. When the alpha-amylase degrades the starch polymers, the released blue dye is water soluble and concentration of dye can be determined by measuring absorbance at 620 nm. The concentration of blue is proportional to the alpha-amylase activity in the sample.

The amylase sample to be analyzed is diluted in activity buffer with the desired pH. One substrate tablet is suspended in 5 mL activity buffer and mixed on magnetic stirrer. During mixing of substrate transfer 150 µl to microtiter plate (MTP) or PCR-MTP. Add 30 µl diluted amylase sample to 150 µl substrate and mix. Incubate for 15 minutes at 37° C. The reaction is stopped by adding 30 µl 1M NaOH and mix. Centrifuge MTP for 5 minutes at 4000×g. Transfer 100 µl to new MTP and measure absorbance at 620 nm.

The amylase sample should be diluted so that the absorbance at 620 nm is between 0 and 2.2, and is within the linear range of the activity assay.
EnzChek® Assay:

For the determination of residual amylase activity an EnzChek® Ultra Amylase Assay Kit (E33651, Invitrogen, La Jolla, Calif., USA) may be used.

The substrate is a corn starch derivative, DQ™ starch, which is corn starch labeled with BODIPY® FL dye to such a degree that fluorescence is quenched. One vial containing approx. 1 mg lyophilized substrate is dissolved in 100 microliters of 50 mM sodium acetate (pH 4.0). The vial is vortexed for 20 seconds and left at room temperature, in the dark, with occasional mixing until dissolved. Then 900 microliters of 100 mM acetate, 0.01% (w/v) TRITON® X100, 0.125 mM CaCl2, pH 5.5 is added, vortexed thoroughly and stored at room temperature, in the dark until ready to use. The stock substrate working solution is prepared by diluting 10-fold in residual activity buffer (100 mM acetate, 0.01% (w/v) TRITON® X100, 0.125 mM CaCl2, pH 5.5). Immediately after incubation the enzyme is diluted to a concentration of 10-20 ng enzyme protein/ml in 100 mM acetate, 0.01% (W/v) TRITON® X100, 0.125 mM CaCl2, pH 5.5.

For the assay, 25 microliters of the substrate working solution is mixed for 10 second with 25 microliters of the diluted enzyme in a black 384 well microtiter plate. The fluorescence intensity is measured (excitation: 485 nm, emission: 555 nm) once every minute for 15 minutes in each well at 25° C. and the Vmax is calculated as the slope of the plot of fluorescence intensity against time. The plot should be linear and the residual activity assay has been adjusted so that the diluted reference enzyme solution is within the linear range of the activity assay.
Increased Stability of Variants in Model Detergent Compositions The variants generated as described and listed in the Examples have increased stability in model detergent A evaluated by the Phadebas assay. The following detergent compositions were prepared;
Preparation of Model A (0.33%):
Model Detergent A

| Compound | Content of compound (% w/w) | % active component (% w/w) |
| --- | --- | --- |
| LAS | 12.00 | 11.60 |
| AEOS, SLES | 17.63 | 4.90 |
| Soy fatty acid | 2.75 | 2.48 |
| Coco fatty acid | 2.75 | 2.80 |
| AEO | 11.00 | 11.00 |
| Sodium hydroxide | 1.75 | 1.80 |
| Ethanol/Propan-2-ol | 3.00 | 2.70/0.30 |
| MPG | 6.00 | 6.00 |
| Glycerol | 1.71 | 1.70 |

| Compound | Content of compound (% w/w) | % active component (% w/w) |
| --- | --- | --- |
| TEA | 3.33 | 3.30 |
| Sodium formate | 1.00 | 1.00 |
| Sodium citrate | 2.00 | 2.00 |
| DTMPA | 0.48 | 0.20 |
| PCA | 0.46 | 0.18 |
| Phenoxy ethanol | 0.50 | 0.50 |
| $H_2O$, ion exchanged | 33.64 | 33.64 |

Water hardness was adjusted to 15° dH by addition of CaCl2, MgCl2, and NaHCO3 (Ca2+:Mg2+:HCO3−=4:1:7.5) to the test system. After washing the textiles were flushed in tap water and dried 4:1 molar ratio of CaCl2 and MgCl2 stock solution with 6000 dH (water hardness)

125.8 g of CaCl2.2H2O was weighed into 1 liter bottle and to this 500 ml of type I water was added and stirred well. To this 43.8 g of MgCl2.61H2O was weighed and added and dissolved well and the final volume was made up to 1000 ml with type I water. 0.535 M solution of NaHCO3

44.9 g of Sodium Hydrogen carbonate was dissolved in 100 ml of type I water.

Model a Detergent with a Water Hardness of 15 (15° dH)

3.335 g of Model A detergent was weighed and transferred into 1 litre bottle and to this 865 ml of type I water was added and mixed well. To this 7.5 ml of 0.535M $NaHCO_3$ was added, mixed well and made up the volume to 1 liter with type 1 water. To adjust the water hardness to 15° dH 2.5 ml of 4:1 molar ratio of $CaCl_2.2H_2O$ and $MgCl_2.6H_2O$ stock solution with 6000° dH was added and the mixture was stirred for 15 min.

Example 1: Amylase Performance During Starch Liquefaction Evaluated by Dextrose Equivalents (DE) and Viscosity A study was conducted to evaluate alpha amylase performance during starch liquefaction performed on a 5-gram scale. A control alpha-amylase having at least the E185P substitution (using SEQ ID NO: 2 for numbering) and shown in SEQ ID NO: 10 was compared to alpha-amylase variants having in addition substitutions at either position 239 or 276 or both (using SEQ ID NO: 2 for numbering) according to the tables below. Starch slurry at 40% total solids containing 10 ppm sodium and 5 ppm calcium was adjusted to pH 4.3 with potassium hydroxide and aliquoted into 20 mL glass vials. 4.69 µg enzyme protein per gram dried starch was dosed into the 5-gram starch slurry and mixed using a vortex. Glass vials containing the starch slurry and alpha amylase were capped with a screw cap containing a silicon septa and transferred to a 12-vial heater block for incubation at 98° C. for 120 minutes with constant shaking. Samples were evaluated in triplicate at 30 and 120 minutes to be measured for dextrose equivalents (DE) after enzyme inactivation. For DE determinations enzyme activation was done using an ice bath and for viscosity enzyme activation was done using 5M HCl.

DE values were obtained by measuring the conductivity, refractive index, and osmolality of the maltodextrin diluted 2× after liquefaction (Source: Y. Rong, M. Sillick, C. M. Gregson "Determination of Dextrose Equivalent Value and Average Molecular Weight of Maltodextrin By Osmometry"; Journal of Food Science, 2009).

Viscosity measurement was performed using Vipr Technology at room temperature using Brand Tips 0-200 uL (speed 3; volume of 200 uL). Viscosity is usually measured by rheological instrument, such as Brookfield viscometer. The viscosity of a solution is a measure of the rate of deformation upon exposure to shear stress (the force required to generate a liquid flow). The ViPr technology is based on the pressure drop needed to generate a liquid flow at constant velocity.

This is achieved by measuring the pressure in the headspace of an automated pipette (mViPr) during aspirating and dispensing. Thus this technology provides a method of determining enzyme activity in a fluid, wherein the activity over time provides a viscosity-change in the fluid, by the use of a device equipped with a pressure sensor to determine the change in the fluid viscosity over time as a measure of the enzyme activity. This technology has been described in detail in WO2011/107472.

All results are averages of triplicate evaluations. Results below show that variants having a combination of E185P with a substitution at position S239X or K276X result in higher DE number and lower viscosity compared to the control alpha-amylase having only the E185P substitution (SEQ ID NO: 2 numbering).

TABLE 1

Effect of combined susbtitutions E185P + S239X compared to control (SEQ ID NO: 10 comprising E185P)

| Mutation | Control | S239T | S239F | S239D | S239I | S239L | S239P | S239Y |
| --- | --- | --- | --- | --- | --- | --- | --- | --- |
| DE by osmometer | | | | | | | | |
| 30 min | 6.8 | 6.6 | 6.1 | 7.2 | 7.3 | 7.6 | 6.6 | 7.6 |
| 120 min | 9.3 | 9.8 | 9.9 | 9.8 | 10.2 | 10.6 | 10.3 | 13.4 |
| Viscosity (Pascal) | | | | | | | | |
| 30 min | 4467 | 4683 | 5214 | 3303 | 4080 | 3360 | 3653 | 3556 |
| 120 min | 3069 | 2810 | 5315 | 2023 | 1873 | 1693 | 1797 | 2218 |

TABLE 2

Effect of combined susbtitutions E185P + K276X
compared to control (SEQ ID NO: 10 comprising E185P)

| Mutation | Control | K276L | K276D | K276M | K276W | K276I | K276Y |
|---|---|---|---|---|---|---|---|
| DE by osmometer | | | | | | | |
| 30 min | 6.8 | 7.7 | 8.1 | 7.4 | 8.6 | 8.5 | 8.1 |
| 120 min | 9.3 | 13.0 | 12.8 | 10.3 | 15.5 | 14.9 | 14.0 |
| Viscosity (Pascal) | | | | | | | |
| 30 min | 4467 | 3997 | 3077 | 3747 | 3147 | 3327 | 4330 |
| 120 min | 3069 | 2437 | 2653 | 3777 | 2463 | 2757 | 2403 |

Example 2: Stability Testing of Alpha-Amylase Variants Using Thermal Stress Conditions A control alpha-amylase having at least the E185P substitution (using SEQ ID NO: 2 for numbering) and shown in SEQ ID NO: 10 was compared to alpha-amylase variants having in addition substitutions at either position 239 or 276 or both (using SEQ ID NO: 2 for numbering) according to the tables below.

Sample Preparation and Incubation:

Purified protein samples were normalized to a concentration of 0.1 mg/ml (100 ppm) in 10 mM K-acetate buffer pH 4.5 containing 0.12 mM Calcium chloride (5 ppm $Ca^{2+}$), 0.01% Triton X-100.

Stress Conditions:

For stressing the protein, normalized protein samples (10 µl, final concentration 5 ppm) were mixed with stress buffer (190 µl containing 100 mM K-acetate pH 4.3, 5 ppm Calcium, 15 ppm Sodium, Triton X-100 and 1.0% cooked Cargill starch). After mixing (16+16 cycles in Tecan), 50 µl sample was transferred to PCR plate and incubated at 80° C./83° C./85° C./87° C./90° C. for 20 min and 50 µl sample (protein+stress buffer) kept at 25° C. for 20 min was considered as unstressed sample.

Activity Assay

After the incubation period, samples from stressed and unstressed plates were diluted 5× (20 µl sample+80 µl activity buffer containing 100 mM MOPS buffer pH 7.0, 5 ppm Calcium, 15 ppm sodium and 0.01% Triton X-100). To measure the activity, 10 µl each from the diluted sample was transferred into 384-well plate and to this, 40 ul of G-7pNP substrate solution (20 ml of R1 solution and 5 ml of R2 solution, prepared as mentioned in the kit provided by the vendor) was added followed by measurement of kinetics for 10 min at 1 min interval at 405 nm. Activity of unstressed and stressed sample was determined and the % residual activity was calculated by:

% residual activity=(absorbance of stressed sample/absorbance of Unstressed sample)*100

Improvement factor (IF) was calculated by shown below:

Improvement Factor (IF) of variant=(% residual activity of the variant/% residual activity of the backbone)

Half-life (T½ (in min)) was calculated using the following formulas:

T½(variants)=(Ln(0.5)/Ln(RA-variants/100))*Time

T½(Wild-type)=(Ln(0.5)/Ln(RA-wild-type/100))*Time

TABLE 3

Effect of combined substitutions E185P with S239X or K276X

| Substitution E185P+ | Incubation T [° C.] | Incubation time [min] | T1/2 (min) | Improvement factor (IF) over SEQ ID NO: 10 |
|---|---|---|---|---|
| K276L | 80° C. | 20 min | 28.0 | 1.97 |
| K276D | 80° C. | 20 min | 16.9 | 1.43 |
| K276W | 80° C. | 20 min | 68.4 | 2.64 |
| K276I | 80° C. | 20 min | 38.9 | 2.27 |
| K276H | 80° C. | 20 min | 15.9 | 1.44 |
| K276S | 80° C. | 20 min | 12.3 | 1.12 |
| K276T | 80° C. | 20 min | 18.7 | 1.65 |
| K276N | 80° C. | 20 min | 14.1 | 1.29 |
| K276Q | 80° C. | 20 min | 14.8 | 1.36 |
| K276V | 80° C. | 20 min | 20.3 | 1.76 |
| K276A | 80° C. | 20 min | 12.6 | 1.16 |
| K276Y | 80° C. | 20 min | 35.1 | 2.34 |
| K276F | 80° C. | 20 min | 44.0 | 2.00 |
| S239T | 80° C. | 20 min | 15.2 | 1.40 |
| S239F | 80° C. | 20 min | 25.0 | 2.01 |
| S239I | 80° C. | 20 min | 16.2 | 1.48 |
| S239L | 80° C. | 20 min | 15.0 | 1.38 |
| S239P | 80° C. | 20 min | 16.4 | 1.49 |
| S239Y | 80° C. | 20 min | 33.4 | 2.30 |
| S239F | 80° C. | 20 min | 50.0 | 2.08 |

TABLE 4

Effect of E185P substitution in combination with S239X and K276X

| Substitution E185P+ | Incubation T [° C.] | Incubation time [min] | T1/2 (min) | Improvement factor (IF) over SEQ ID NO: 10 |
|---|---|---|---|---|
| S239L K276W | 90° C. | 20 min | 21.4 | 3.54 |
| S239Y K276I | 87° C. | 20 min | 18.6 | 2.49 |
| S239Y | 85° C. | 20 min | 20.7 | 2.43 |
| S239Y | 87° C. | 20 min | 20.7 | 2.43 |
| S239P K276W | 80° C. | 20 min | 62.2 | 1.97 |
| S239L K276I | 87° C. | 20 min | 13.4 | 1.92 |
| S239L | 80° C. | 20 min | 14.6 | 1.61 |
| S239P K276I | 87° C. | 20 min | 10.8 | 1.49 |
| S239L | 80° C. | 20 min | 14.6 | 1.17 |
| S239L K276W | 90° C. | 20 min | 21.4 | 3.54 |
| S239Y K276I | 87° C. | 20 min | 18.6 | 2.49 |
| S239P K276W | 80° C. | 20 min | 62.2 | 1.97 |
| S239L K276I | 87° C. | 20 min | 13.4 | 1.92 |
| K276I | 87° C. | 20 min | 14.0 | 1.95 |
| K276W | 90° C. | 20 min | 21.9 | 3.21 |
| S239P K276I | 87° C. | 20 min | 10.8 | 1.49 |
| K276I | 87° C. | 20 min | 14.0 | 1.95 |
| K276W | 90° C. | 20 min | 21.9 | 3.29 |

All combinations listed showed an increased stability at the tested temperature compared to the control amylase shown in SEQ ID NO: 10.

Example 3. Thermostability Assay for Alpha-Amylase Variants at pH 5.0 Assay Principle The thermostability of a reference alpha-amylase (SEQ ID NO: 11 a derivative of SEQ ID NO: 1 and 27) and alpha-amylase variants thereof was determined by incubating the reference alpha-amylase and variants at pH 5.0 and temperatures of 95° C. in the presence of 0.9% w/v corn starch, 0.12 mM $CaCl_2$ and 2. mM NaCl followed by determination of residual activity using the EnzChek® substrate (EnzChek® Ultra Amylase assay kit, E33651, Molecular Probes). Residual activity was determined relative to control samples, which were incubated at room temperature at low sodium and starch concentration.

Materials

| Enzyme Dilution Buffer: | 10 mM potassium acetate, 0.01% Triton X-100, 0.125 mM CaCl$_2$, pH adjusted to 5.0 using 1M HCl or 2M KOH |
|---|---|
| Stability Buffer: | 100 mM potassium acetate, 0.01% Triton X100, 0.12 mM CaCl$_2$, 2.17 mM NaCl and 1% starch from corn, pH 5.0 using 1M HCl or 2M KOH |
| Residual Activity Buffer: | 100 mM potassium acetate, 0.01% Triton X100, 0.12 mM CaCl$_2$, pH adjusted to 5.5 using 1M HCl or 2M KOH) |
| Substrate Buffer: | 50 mM Sodium acetate, adjusted to pH 4.0 using 1M HCl or 1M NaOH |
| Substrate: | 1 mg/mL BODIPY ® FL labelled DQTM starch substrate (from EnzChek ® Ultra Amylase assay kit, E33651, Molecular Probes) in Substrate Buffer |
| Substrate Working Solution: | Substrate diluted 10-fold in Residual Activity Buffer |

Procedure Examples for 12 and 24 ng/mL Final Enzyme Concentration

The residual activity is determined at two final enzyme concentrations (either 8 ng/mL and 16 ng/mL or 12 ng/mL and 24 ng/mL). Samples having activities outside the linear range were excluded from the calculation of residual activity. Within the linear range, the average residual activity is used.

Purified enzyme samples were diluted to working concentrations of 2.4 ppm (micrograms/ml) in Enzyme Dilution Buffer.

15 µL enzyme and 135 µL Stability Buffer was transferred to a 96-well PCR microtiter plate and mixed (Plate 1) in duplicates. After mix the enzyme concentration was 240 ng/mL and the concentrations of the buffer components were 92 mM potassium acetate, 0.01% Triton X-100, 0.12% CaCl$_2$, 1 mM NaCl, and 0.9% starch From Plate 1, an aliquot of 16 µL was transferred to a new plate (Plate 2) together with 144 µL Residual Activity Buffer, Enzyme concentration after dilution was 24 ng/mL and the concentrations of the buffer components were 99% potassium acetate, 0.01% Triton X-100, 0.12% CaCl$_2$, 0.1 mM NaCl and 0.09% starch.

Plate 2 was stored at room temperature and used as control samples.

The remaining part of the samples in Plate 1 were heat stressed by incubation for 15 or 30 minutes at 95° C. in PCR machine (Bio-Rad T100 Thermal Cycler).

After incubation, samples on Plate 1 were diluted 10-fold (16 µL sample+144 µL Residual Activity Buffer) to a final enzyme concentration of 24 ng/mL.

Incubated samples and control samples were further diluted 2-fold (67 µL sample+67 µL Residual Activity Buffer) to a final enzyme concentration of 12 ng/mL For the activity measurements, 25 µL diluted enzyme (both 12 ng/mL and 24 ng/mL samples) were transferred to black 384-well microtiter plates.

Reaction was started by adding 25 µL Substrate Working Solution.

Immediately after addition of Substrate, fluorescence was read at 25° C. every minute for 10 minutes (Ex: 485 nm, Em: 555 nm). Activity was determined from the slope of measured fluorescence versus time.

The residual activity (% RA) was calculated as Activity in heat stressed sample/Activity in control sample*100. Before calculating the residual activity, it was ensured that the activity of the heat stressed samples and in the control samples were within the linear range of the activity assay. The linear range can be determined by measuring the activity of a range of standards (typically 0-100 ng/mL) of the reference amylase.

Assuming logarithmic decay, half life time (T ½% (min)) was calculated using the equation:

$$T1/2_{min} = t_{min} \times \frac{\ln(0.5)}{\ln\left(\frac{RA}{100}\right)}$$

where T is assay incubation time in minutes, and % RA is % residual activity determined in assay. Using this assay setup, the half-life time was determined as a measure of thermostability for the reference alpha-amylase and variants thereof as shown in Tables 5.

TABLE 5

Half-life improvement factor (HIF) after heat shock based on residual activity measurements

| Substitution | Incubation T [° C.] | Incubation time [min] | HIF relative to control (SEQ ID NO: 11) |
|---|---|---|---|
| Control | 95° C. | 15 min | 1.0 |
| E188P | 95° C. | 15 min | 1.41 |
| E188P N275F | 95° C. | 15 min | 1.19 |
| E188P N275Y | 95° C. | 15 min | 1.26 |
| E188P N275W | 95° C. | 15 min | 1.16 |
| E188P N275H | 95° C. | 15 min | 1.19 |
| E188P K279F | 95° C. | 15 min | 1.53 |
| E188P K279Y | 95° C. | 15 min | 1.41 |
| E188P K279W | 95° C. | 15 min | 1.96 |
| E188P K279H | 95° C. | 15 min | 1.45 |

All combinations listed showed an increased stability at the tested temperature compared to the control amyase shown in SEQ ID NO: 11.

Example 4: Low pH Stability of *Bacillus licheniformis* Alpha-Amylase Variants of the Invention Amino acid substitutions were introduced in *Bacillus licheniformis* alpha-amylase (SEQ ID NO: 2) by standard site directed methods. The substitutions are indicated in the table below and the position numbering is according to SEQ ID NO: 2. The modified amylase genes were transformed into and expressed in *Bacillus subtilis*. The *Bacillus subtilis* broths were centrifuged and the amylase containing supernatants isolated and diluted 10 times in 100 mM K-acetate pH 4.5 with 5 ppm CaCl$_2$. The samples were then split in to two samples; one was stored at 4° C. and the other was incubated at 45° C. for 30 minutes. Following that, the samples were diluted 10 times in assay buffer (100 mM Britton-Robinson buffer (100 mM acetic acid+100 mM phosphate acid+100 mM boric acid) with 0.12 mM CaCl$_2$+ 0.01% Brij, pH adjusted to pH 7.3) and the amylase activity measured using Phadebas amylase assay as described under methods. All measurements were made in triplicates. The residual activities were calculated as the ratio between the activity in the samples that have been incubated at 45° C. relative to activity in the samples that have been incubated at 4° C. Further the half-life and the improvement factor relative to WT (IF-WT) were calculated.

TABLE 6

Residual activity (RA) of alpha-amylase variants after incubation in pH 4.5 at 45° C. for 30 min.

| Amylase variants | RA | Half life (min) | IF (WT) |
|---|---|---|---|
| WT - reference | 34 | 19 | 1.00 |
| S239W | 27 | 16 | 0.79 |
| S239Y | 24 | 15 | 0.71 |
| S239F | 37 | 21 | 1.08 |
| S239H | 35 | 20 | 1.02 |
| S239Q | 69 | 57 | 2.02 |
| K276W | 4 | 7 | 0.13 |
| K276Y | 4 | 6 | 0.11 |
| K276F | 2 | 5 | 0.06 |
| K276H | 8 | 8 | 0.23 |
| K276I | 3 | 6 | 0.10 |
| K276L | 2 | 5 | 0.05 |

This example demonstrates that none of the alpha-amylase variants with a single substitution in S239 or K276 showed increased stability at low pH, except for S239Q that has an IF of approx.2.

Example 5: Low pH Stability of *Bacillus licheniformis* Alpha-Amylase Variants of the Invention Using standard site directed methods, amino acid substitutions were introduced in a variant of the *Bacillus licheniformis* alpha-amylase (SEQ ID NO: 2) having a proline at position 185. The substitutions are indicated in the table below and the position numbering is according to SEQ ID NO: 2. The modified amylase genes were transformed into and expressed in *Bacillus subtilis*. The *Bacillus subtilis* broths were centrifuged and the amylase containing supernatants isolated and diluted 10 times in 100 mM K-acetate pH 4.5 with 5 ppm $CaCl_2$. The samples were then split in two samples; one was stored at 4° C. and the other was incubated at 60° C. for 30 minutes. Following that, the samples were diluted 10 times in assay buffer (100 mM Britton-Robinson buffer (100 mM acetic acid+100 mM phosphate acid+100 mM boric acid)+0.12 mM $CaCl_2$+ 0.01% Brij, pH adjusted to pH 7.3) and the amylase activity measured using Phadebas amylase assay as described under methods. The residual activities were calculated as the ratio between the activity in the samples that have been incubated at 60° C. relative to activity in the samples that have been incubated at 4° C. Further the half-life and the improvement factor relative to reference were calculated.

TABLE 7

Residual activity (RA) of alpha-amylase variants after incubation in pH 4.5 at 60° C. for 30 min.

| Amylase variants | RA | Half life (min) | IF |
|---|---|---|---|
| E185P | 46 | 27 | 1.00 |
| E185P S239W | 56 | 36 | 1.21 |
| E185P S239Y | 71 | 60 | 1.53 |
| E185P S239F | 55 | 35 | 1.19 |
| E185P S239H | 71 | 61 | 1.54 |
| E185P S239Q | 7 | 8 | 0.16 |
| E185P K276W | 73 | 66 | 1.58 |
| E185P K276Y | 57 | 37 | 1.23 |
| E185P K276F | 61 | 42 | 1.32 |
| E185P K276H | 58 | 38 | 1.25 |
| E185P K276i | 93 | 273 | 2.00 |
| E185P K276L | 59 | 40 | 1.28 |
| E185P S239Y K276W | 52 | 32 | 1.13 |
| E185P S239F K276W | 89 | 180 | 1.93 |
| E185P S239Y K276Y | 83 | 115 | 1.80 |
| E185P S239Y K276F | 87 | 153 | 1.89 |
| E185P S239Y K276H | 88 | 157 | 1.89 |
| E185P S239Y K276I | 88 | 168 | 1.91 |
| E185P S239Y K276L | 85 | 132 | 1.85 |

This example demonstrates that alpha-amylase variants, introduced in an amylase reference with a proline in position 185 (SEQ ID NO: 2), with substitution in S239 to W, Y, F or H and/or in K276 to W, Y, F, H, L or I have increased stability at low pH. Surprisingly, a destabilizing effect is observed for the substitution S239Q in combination with E185P.

Example 6: Low pH Stability of *Bacillus licheniformis* Alpha-Amylase Variants of the Invention Using standard site directed methods, amino acid substitutions were introduced in a variant of the *Bacillus licheniformis* alpha-amylase (SEQ ID NO: 2) having the modifications E185P I201Y. The substitutions are indicated in the table below and the position numbering is according to SEQ ID NO: 2. The modified amylase genes were transformed into and expressed in *Bacillus subtilis*. The *Bacillus subtilis* broths were centrifuged and the amylase containing supernatants isolated and diluted 10 times in 100 mM K-acetate pH 4.5 with 5 ppm $CaCl_2$. The samples were then split in two samples; one was stored at 4° C. and the other was incubated at 80° C. for 30 minutes. Following that, the samples were diluted 10 times in assay buffer (100 mM Britton-Robinson buffer (100 mM acetic acid+100 mM phosphate acid+100 mM boric acid)+0.12 mM $CaCl_2$+ 0.01% Brij, pH adjusted to pH 7.3) and the amylase activity measured using Phadebas amylase assay as described under methods. The residual activities were calculated as the ratio between the activity in the samples that have been incubated at 80° C. relative to activity in the samples that have been incubated at 4° C. Further the half-life and the improvement factor relative to reference were calculated.

TABLE 8

Residual activity (RA) of alpha-amylase variants after incubation in pH 4.5 at 80° C. for 30 min.

| Amylase variants | RA | Half life (min) | IF |
|---|---|---|---|
| E185P I201Y | 15 | 11 | 1.00 |
| E185P I201Y S239Q | 3 | 6 | 0.24 |
| E185P I201Y S239Y | 41 | 23 | 2.81 |
| E185P I201Y K276W | 23 | 14 | 1.57 |
| E185P I201Y K276Y | 34 | 19 | 2.36 |
| E185P I201Y K276F | 37 | 21 | 2.53 |
| E185P I201Y K276H | 28 | 16 | 1.95 |
| E185P I201Y K276I | 42 | 24 | 2.92 |

TABLE 8-continued

Residual activity (RA) of alpha-amylase variants
after incubation in pH 4.5 at 80° C. for 30 min.

| Amylase variants | RA | Half life (min) | IF |
| --- | --- | --- | --- |
| E185P I201Y K276L | 20 | 13 | 1.36 |
| E185P I201Y S239F | 45 | 26 | 3.07 |

This example demonstrates that alpha-amylase variants, introduced in an amylase reference with a proline in position 185 and tyrosine in position 201 (using SEQ ID NO: 2 for numbering), with substitution in S239 to Y or F and in K276 to W, Y, F, H, I or L have increased stability at low pH. Surprisingly, a destabilizing effect is observed for the substitution S239Q in combination with E185P and I201Y.

Example 7: Chelator Stability of *Bacillus licheniformis* Alpha-Amylase Variants of the Invention Amino acid substitutions were introduced in *Bacillus licheniformis* alpha-amylase (SEQ ID NO: 2) by standard site directed methods. The substitutions are indicated in the table below and the position numbering is according to SEQ ID NO: 2. The modified amylase genes were transformed into and expressed in *Bacillus subtilis*. The *Bacillus subtilis* broths were centrifuged and the amylase containing supernatants isolated and diluted 10 times in model detergent A with 0.5% EDTA so the resulting concentration is 90% detergent and 0.45% EDTA. The samples were then split in two samples; one was stored at 4° C. and the other was incubated at 45° C. for 60 minutes. Following that, the samples were diluted 10 times in 100 mM assay buffer (100 mM Britton-Robinson buffer (100 mM acetic acid+100 mM phosphate acid+100 mM boric acid)+0.12 mM $CaCl_2$+ 0.01% Brij, pH adjusted to pH 7.3) and the amylase activity measured using Phadebas amylase assay as described under methods. The residual activities were calculated as the ratio between the activity in the samples that have been incubated at 45° C. relative to activity in the samples that have been incubated at 4° C. Further the half-life and the improvement factor relative to WT (IF-WT) were calculated.

TABLE 9

Residual activity (RA) of alpha-amylase variants after incubation
in model detergent A with EDTA at 45° C. for 60 min.

| Amylase variants | RA | Half life (min) | IF (WT) |
| --- | --- | --- | --- |
| WT - reference | 56 | 72 | 1.00 |
| S239W | 14 | 21 | 0.26 |
| S239Y | 79 | 181 | 1.41 |
| S239F | 82 | 208 | 1.46 |
| S239H | 88 | 329 | 1.57 |
| S239Q | 57 | 75 | 1.02 |
| K276W | 0 | — | — |
| K276Y | 0 | — | — |
| K276F | 0 | — | — |
| K276H | 0 | — | — |
| K276i | 0 | — | — |
| K276L | 0 | — | — |

This example demonstrates that alpha-amylase variants with a single substitution in S239 to Y, F or H increase the stability significantly over the wild type reference.

Example 8: Chelator Stability of *Bacillus licheniformis* Alpha-Amylase Variants of the Invention Using standard site directed methods, amino acid substitutions were introduced in a variant of the *Bacillus licheniformis* alpha-amylase (SEQ ID NO: 2) having the modification E185P. The substitutions are indicated in the table below and the position numbering is according to SEQ ID NO: 2. The modified amylase genes were transformed into and expressed in *Bacillus subtilis*. The *Bacillus subtilis* broths were centrifuged and the amylase containing supernatants isolated and diluted 10 times in model detergent A with 0.5% EDTA so the resulting concentration is 90% detergent and 0.45% EDTA. The samples were then split in two samples; one was stored at 4° C. and the other was incubated at 45° C. for 18 hours. Following that, the samples were diluted 10 times in assay buffer (same as above) and the amylase activity measured using Phadebas amylase assay as described under methods. The residual activities were calculated as the ratio between the activity in the samples that have been incubated at 45° C. relative to activity in the samples that have been incubated at 4° C. Further the half-life and the improvement factor relative to E187P variant were calculated.

TABLE 10

Residual activity (RA) of alpha-amylase variants after incubation
in model detergent A with EDTA at 45° C. for 18 hours.

| Amylase variants | RA | Half life (hours) | IF |
| --- | --- | --- | --- |
| E185P | 36 | 12 | 1.00 |
| E185P S239W | 86 | 85 | 2.37 |
| E185P S239Y | 82 | 63 | 2.25 |
| E185P S239H | 63 | 27 | 1.71 |
| E185P S239Q | 3 | 4 | 0.08 |
| E185P K276W | 90 | 121 | 2.47 |
| E185P K276Y | 75 | 44 | 2.06 |
| E185P K276F | 82 | 64 | 2.26 |
| E185P K276i | 52 | 19 | 1.43 |
| E185P K276L | 47 | 17 | 1.29 |
| E185P S239F K276W | 95 | 223 | 2.59 |
| E185P S239H K276W | 51 | 19 | 1.40 |
| E185P S239Y K276Y | 69 | 34 | 1.90 |
| E185P S239Y K276F | 75 | 44 | 2.06 |
| E185P S239Y K276H | 85 | 77 | 2.33 |
| E185P S239Y K276L | 74 | 41 | 2.03 |

This example demonstrates that alpha-amylase variants introduced in an amylase reference with a proline in position 185 (using SEQ ID NO: 2 for numbering) with substitution in S239 to W, Y or H and/or in K276 to W, Y, F, L or I have increased stability in detergent with EDTA. Surprisingly, a destabilizing effect is observed for the substitution S239Q in combination with E185P.

Example 9: Low pH Stability of Cytophaga Alpha-Amylase Variants of the Invention Amino acid substitutions were introduced in Cytophaga alpha-amylase (SEQ ID NO: 5) by standard site directed methods. The substitutions are indicated in the table below and the position numbering is according to SEQ ID NO: 5. The modified amylase genes were transformed into and expressed in *Bacillus subtilis*. The *Bacillus subtilis* broths were centrifuged and the amylase containing supernatants isolated and diluted 10 times in 100 mM K-acetate pH 4.5 with 5 ppm $CaCl_2$. The samples were then split in to two samples; one was stored at 4° C. and the other was incubated at 40° C. for 30 minutes. Following that, the samples were diluted 10 times in assay buffer (100 mM Britton-Robinson buffer (100 mM acetic acid+100 mM phosphate acid+100 mM boric acid) with 0.12 mM $CaCl_2$+0.01% Brij, pH adjusted to pH 7.3) and the amylase activity measured using Phadebas amylase assay as described under methods. All measurements were made in triplicates. The residual activities were calculated as the ratio between the activity in the samples that have been incubated at 40° C. relative to activity in the samples that have been incubated at 4° C. Further the half-life and the improvement factor relative to WT(IF-WT) and relative to the E187P (IF-E187P) variant were calculated.

TABLE 11

Residual activity (RA) of alpha-amylase variants after incubation in pH 4.5 at 40° C. for 30 min.

| Amylase variants | RA | Half life (min) | IF (WT) | IF (E187P) |
|---|---|---|---|---|
| WT - reference | 20 | 13 | 1.00 | |
| S241Q | 60 | 41 | 2.93 | |
| S241W | 16 | 11 | 0.79 | |
| S241Y | 15 | 11 | 0.73 | |
| S241F | 17 | 12 | 0.85 | |
| S241H | 8 | 8 | 0.41 | |
| K278W | 8 | 8 | 0.41 | |
| K278F | 1 | 4 | 0.03 | |
| K278H | 0 | 4 | 0.02 | |
| K278I | 0 | 3 | 0.01 | |
| E187P | 7 | 8 | 0.35 | 1.00 |
| E187P S241Q | 1 | 5 | 0.06 | 0.17 |
| E187P S241Y | 57 | 37 | 2.77 | 7.92 |
| E187P S241F | 47 | 28 | 2.31 | 6.61 |
| E187P S241H | 57 | 37 | 2.80 | 8.00 |
| E187P K278W | 13 | 10 | 0.65 | 1.87 |
| E187P K278F | 17 | 12 | 0.81 | 2.32 |
| E187P K278I | 27 | 16 | 1.31 | 3.74 |

This example demonstrates that alpha-amylase variants with a single substitution in S241 to W, Y, F, H or K278 W, F, H, I have decreased stability at low pH. But when introduced in an amylase with a proline (P) in position 187 (numbers according to SEQ ID No: 5), these substitutions increase the stability at low pH significantly. Surprisingly, it is found that the substitution S241Q is shown to be destabilizing in combination with E187P.

Example 10: Low pH Stability of Cytophaga Alpha-Amylase Variants of the Invention Using standard site directed methods, amino acid substitutions were introduced in a variant of the Cytophaga alpha-amylase (SEQ ID NO: 5) having the modifications R178*+G179*+E187P. The substitutions are indicated in the table below and the position numbering is according to SEQ ID NO: 5. The modified amylase genes were transformed into and expressed in *Bacillus subtilis*. The *Bacillus subtilis* broths were centrifuged and the amylase containing supernatants isolated and diluted 10 times in 100 mM K-acetate pH 4.5 with 5 ppm $CaCl_2$. The samples were then split in two samples; one was stored at 4° C. and the other was incubated at 60° C. for 60 minutes. Following that, the samples were diluted 10 times in assay buffer (100 mM Britton-Robinson buffer (100 mM acetic acid+100 mM phosphate acid+100 mM boric acid)+0.12 mM $CaCl_2$+0.01% Brij, pH adjusted to pH 7.3) and the amylase activity measured using Phadebas amylase assay as described under methods. The residual activities were calculated as the ratio between the activity in the samples that have been incubated at 60° C. relative to activity in the samples that have been incubated at 4° C. Further the half-live and the improvement factor relative to reference were calculated.

TABLE 12

Residual activity (RA) of alpha-amylase variants after incubation in pH 4.5 at 60° C. for 60 min.

| Amylase variants | RA | Half life (min) | IF |
|---|---|---|---|
| R178* G179* E187P | 40 | 46 | 1.00 |
| R178* G179* E187P S241Q | 1 | 9 | 0.02 |
| R178* G179* E187P S241Y | 59 | 80 | 1.47 |
| R178* G179* E187P S241F | 55 | 69 | 1.36 |
| R178* G179* E187P K278W | 57 | 73 | 1.40 |
| R178* G179* E187P K278Y | 86 | 276 | 2.13 |
| R178* G179* E187P K278F | 69 | 112 | 1.70 |
| R178* G179* E187P K278I | 79 | 179 | 1.96 |
| R178* G179* E187P S241Y K278W | 68 | 109 | 1.69 |
| R178* G179* E187P S241W K278I | 72 | 127 | 1.78 |

This example demonstrates that alpha-amylase variants with substitution in S241 to W, Y, F and in K278 to W, Y, F or I, have increased stability at low pH. Surprisingly, it is found that the S241Q substitution display significant destabilizing effects in combination with E187P.

Example 11: Chelator Stability of Cytophaga Alpha-Amylase Variants of the Invention Amino acid substitutions were introduced in Cytophaga alpha-amylase (SEQ ID NO: 5) by standard site directed methods. The substitutions are indicated in the table below and the position numbering is according to SEQ ID NO: 5. The modified amylase genes were transformed into and expressed in *Bacillus subtilis*. The *Bacillus subtilis* broths were centrifuged and the amylase containing supernatants isolated and diluted 10 times in model detergent A with 0.5% EDTA so the resulting concentration is 90% detergent and 0.45% EDTA. The samples were then split in two samples; one was stored at 4° C. and the other was incubated at 45° C. for 60 minutes. Following that, the samples were diluted 10 times in 100 mM assay buffer (100 mM Britton-Robinson buffer (100 mM acetic acid+100 mM phosphate acid+100 mM boric acid)+0.12 mM $CaCl_2$+0.01% Brij, pH adjusted to pH 7.3) and the amylase activity measured using Phadebas amylase assay as described under methods. The residual activities were calculated as the ratio between the activity in the samples that have been incubated at 45° C. relative to activity in the samples that have been incubated at 4° C. Further the half-life and the improvement factor relative to WT (IF-WT) and relative to the E187P (IF-E187P) variant were calculated.

TABLE 13

Residual activity (RA) of alpha-amylase variants after incubation in model detergent A with EDTA at 45° C. for 60 min.

| Amylase variants | RA | Half life (min) | IF (WT) | IF (E187P) |
|---|---|---|---|---|
| WT - reference | 1.8 | 10 | 1.00 | |
| S241Q | 8.6 | 17 | 4.88 | |
| S241W | 0 | — | — | |

TABLE 13-continued

Residual activity (RA) of alpha-amylase variants after incubation in model detergent A with EDTA at 45° C. for 60 min.

| Amylase variants | RA | Half life (min) | IF (WT) | IF (E187P) |
|---|---|---|---|---|
| S241Y | 0 | — | — | |
| S241F | 1.3 | 10 | 0.76 | |
| S241H | 3.4 | 12 | 1.94 | |
| K278Q | 0 | — | — | |
| K278W | 0 | — | — | |
| K278F | 0 | — | — | |
| K278H | 0 | — | — | |
| K278I | 0 | — | — | |
| E187P | 16.5 | 23 | 9.43 | 1.00 |
| E187P S241Q | 0 | — | — | — |
| E187P S241Y | 54.0 | 68 | 30.81 | 3.27 |
| E187P S241F | 32.1 | 37 | 18.29 | 1.94 |
| E187P S241H | 72.2 | 128 | 41.14 | 4.36 |
| E187P K278F | 27.1 | 32 | 15.43 | 1.64 |
| E187P K278I | 21.8 | 27 | 12.41 | 1.32 |

This example demonstrates that while alpha-amylase variants with a single substitution in S241 or K278 have no or is even destabilizing in detergent with EDTA chelator. But when introduced in an amylase with a proline (P) in position 187 (numbers according to SEQ ID No: 5), the S241 to Y, F or H and K278 to F or I substitutions increase the stability significantly over the wild type reference and in most cases also over the E187P variant. Surprisingly, the opposite effect is observed for the substitution S241Q which becomes highly destabilizing in presence of E187P.

Example 12: Chelator Stability of Cytophaga Alpha-Amylase Variants of the Invention Using standard site directed methods, amino acid substitutions were introduced in a variant of the Cytophaga alpha-amylase (SEQ ID NO: 5) having the modifications R178* G179* E187P. The substitutions are indicated in the table below and the position numbering is according to SEQ ID NO: 5. The modified amylase genes were transformed into and expressed in Bacillus subtilis. The Bacillus subtilis broths were centrifuged and the amylase containing supernatants isolated and diluted 10 times in model detergent A with 0.5% EDTA so the resulting concentration is 90% detergent and 0.45% EDTA. The samples were then split in two samples; one was stored at 4° C. and the other was incubated at 45° C. for 240 minutes. Following that, the samples were diluted 10 times in assay buffer (same as above) and the amylase activity measured using Phadebas amylase assay as described under methods. The residual activities were calculated as the ratio between the activity in the samples that have been incubated at 45° C. relative to activity in the samples that have been incubated at 4° C. Further the half-life and the improvement factor relative to E187P variant were calculated.

TABLE 14

Residual activity (RA) of alpha-amylase variants after incubation in model detergent A with EDTA at 45° C. for 240 min.

| Amylase variants | RA | Half life (min) | IF |
|---|---|---|---|
| R178* G179* E187P | 8.2 | 72 | 1.00 |
| R178* G179* E187P S241Q | 7.4 | 69 | 0.90 |
| R178* G179* E187P S241Y | 9.5 | 77 | 1.15 |
| R178* G179* E187P S241F | 18.9 | 108 | 2.29 |

TABLE 14-continued

Residual activity (RA) of alpha-amylase variants after incubation in model detergent A with EDTA at 45° C. for 240 min.

| Amylase variants | RA | Half life (min) | IF |
|---|---|---|---|
| R178* G179* E187P S241H | 19.3 | 110 | 2.34 |
| R178* G179* E187P K278W | 66.7 | 444 | 8.09 |
| R178* G179* E187P K278Y | 88.8 | 1.510 | 10.77 |
| R178* G179* E187P K278F | 70.6 | 517 | 8.56 |
| R178* G179* E187P K278I | 69.7 | 499 | 8.45 |

This example demonstrates that alpha-amylase variants with substitution in S241 to Y, F or H and in K278 to W, Y, F or I, have increased stability in detergent with EDTA. Surprisingly, a small destabilizing effect is observed for the substitution S241Q in combination with E187P.

Example 13: Chelator Stability of Cytophaga Alpha-Amylase Variants of the Invention Using standard site directed methods, amino acid substitutions were introduced in a variant of the Cytophaga alpha-amylase (SEQ ID NO: 5) having the multiple modifications (N126Y E132H R178* G179* T180D E187P I203Y) which is here referred to as reference amylase. The introduced substitutions are indicated in the table below and the position numbering is according to SEQ ID NO: 5. The modified amylase genes were transformed into and expressed in Bacillus subtilis. The Bacillus subtilis broths were centrifuged and the amylase containing supernatants isolated and diluted 10 times in model detergent A with 0.5% EDTA so the resulting concentration is 90% detergent and 0.45% EDTA. The samples were then split in two samples; one was stored at 4° C. and the other was incubated at 45° C. for 18 hours. Following that, the samples were diluted 10 times in assay buffer (same as above) and the amylase activity measured using Phadebas amylase assay as described under methods. The residual activities were calculated as the ratio between the activity in the samples that have been incubated at 45° C. relative to activity in the samples that have been incubated at 4° C. Further the half-life and the improvement factor relative to reference amylase were calculated.

TABLE 15

Residual activity (RA) of alpha-amylase variants after incubation in model detergent A with EDTA at 45° C. for 18 hours.

| Amylase variants | RA | Half life (hours) | IF |
|---|---|---|---|
| Reference | 48 | 17 | 1.00 |
| +S241Q | 27 | 9 | 0.56 |
| +S241W | 59 | 23 | 1.22 |
| +S241Y | 74 | 42 | 1.54 |
| +S241F | 73 | 39 | 1.51 |
| +S241H | 74 | 42 | 1.54 |
| +K278W | 71 | 36 | 1.47 |
| +K278Y | 61 | 26 | 1.27 |
| +K278I | 50 | 18 | 1.04 |
| +S241Y K278Y | 85 | 77 | 1.76 |
| +S241Y K278F | 55 | 21 | 1.14 |

This example demonstrates that substitution at S241 to W, Y, F or H and/or K278 to W, Y, or I increase the stability in detergent with EDTA.

Example 14: Chelator Stability of *Bacillus halmapalus* Alpha-Amylase Variants of the Invention Using standard site directed methods, amino acid substitutions were introduced in a variant of the *B. halmapalus* alpha-amylase (SEQ ID NO: 6) having the modifications D183* G184* E190P. The substitutions are indicated in the table below and the position numbering is according to SEQ ID NO: 6. The modified amylase genes were transformed into and expressed in *Bacillus subtilis*. The *Bacillus subtilis* broths were centrifuged and the amylase containing supernatants isolated and diluted 10 times in model detergent A with 0.5% EDTA so the resulting concentration is 90% detergent and 0.45% EDTA. The samples were then split in two samples; one was stored at 4° C. and the other was incubated at 45° C. for 60 minutes. Following that, the samples were diluted 10 times in assay buffer (same as above) and the amylase activity measured using Phadebas amylase assay as described under methods. The residual activities were calculated as the ratio between the activity in the samples that have been incubated at 45° C. relative to activity in the samples that have been incubated at 4° C. Further the half-life and the improvement factor relative to E190P variant were calculated.

TABLE 16

Residual activity (RA) of alpha-amylase variants after incubation in model detergent A with EDTA at 45° C. for 60 min.

| Amylase variants | RA | Half life (min) | IF |
|---|---|---|---|
| D183* G184* E190P | 12 | 20 | 1.00 |
| D183* G184* E190P S244Q | 11 | 18 | 0.85 |
| D183* G184* E190P S244W | 25 | 30 | 2.00 |
| D183* G184* E190P S244F | 68 | 107 | 5.48 |
| D183* G184* E190P K281W | 34 | 39 | 2.77 |
| D183* G184* E190P K281Y | 23 | 28 | 1.82 |
| D183* G184* E190P K281I | 19 | 25 | 1.57 |
| D183* G184* E190P S244Y K281W | 60 | 80 | 4.81 |
| D183* G184* E190P S244F K281W | 29 | 34 | 2.38 |
| D183* G184* E190P S244Y K281F | 28 | 32 | 2.22 |
| D183* G184* E190P S244Y K281I | 69 | 112 | 5.58 |

This example demonstrates that alpha-amylase variants with substitution in S244 to W, or F and in K281 to W, Y, or I, have increased stability in detergent with EDTA.

Example 15: Chelator Stability of *Bacillus halmapalus* Alpha-Amylase Variants of the Invention Using standard site directed methods, amino acid substitutions were introduced in a variant of the *B. halmapalus* alpha-amylase (SEQ ID NO: 6) having the multiple modifications (H1* G7A G109A W140Y G182* D183* E190P V206Y Y243F E260G F267Y N280S G304R E391A G476K) which is here referred to as reference amylase. The introduced substitutions are indicated in the table below and the position numbering is according to SEQ ID NO: 6. The modified amylase genes were transformed into and expressed in *Bacillus subtilis*. The *Bacillus subtilis* broths were centrifuged and the amylase containing supernatants isolated and diluted 10 times in model detergent A with 0.5% EDTA so the resulting concentration is 90% detergent and 0.45% EDTA. The samples were then split in two samples; one was stored at 4° C. and the other was incubated at 45° C. for 18 hours. Following that, the samples were diluted 10 times in assay buffer (same as above) and the amylase activity measured using Phadebas amylase assay as described under methods. The residual activities were calculated as the ratio between the activity in the samples that have been incubated at 45° C. relative to activity in the samples that have been incubated at 4° C. Further the half-life and the improvement factor relative to reference amylase were calculated.

TABLE 17

Residual activity (RA) of alpha-amylase variants after incubation in model detergent A with EDTA at 45° C. for 18 hours.

| Amylase variants | RA | Half life (hours) | IF |
|---|---|---|---|
| Reference | 27 | 10 | 1.00 |
| +S244Q | 18 | 7 | 0.67 |
| +S244W | 39 | 13 | 1.46 |
| +S244F | 47 | 16 | 1.73 |
| +S244H | 61 | 25 | 2.25 |
| +K281I | 69 | 34 | 2.57 |
| +K281F | 74 | 42 | 2.75 |
| +S244Y K281I | 37 | 13 | 1.38 |
| +S244H K281W | 48 | 17 | 1.77 |
| +S244W K281W | 56 | 22 | 2.09 |

This example demonstrates that substitution at S244 to W, F, or H and K281 to F or I increase the stability in detergent with EDTA.

Example 16: Low pH Stability of *Bacillus* sp. AA110 Alpha-Amylase Variants of the Invention Amino acid substitutions were introduced in *Bacillus* sp. AA110 alpha-amylase (SEQ ID NO: 7) by standard site directed methods. The substitutions are indicated in the table below and the position numbering is according to SEQ ID NO: 7. The modified amylase genes were transformed into and expressed in *Bacillus subtilis*. The *Bacillus subtilis* broths were centrifuged and the amylase containing supernatants isolated and diluted 10 times in 100 mM K-acetate pH 4.5 with 5 ppm $CaCl_2$. The samples were then split in to two samples; one was stored at 4° C. and the other was incubated at 50° C. for 60 minutes. Following that, the samples were diluted 10 times in assay buffer (100 mM Britton-Robinson buffer (100 mM acetic acid+100 mM phosphate acid+100 mM boric acid) with 0.12 mM $CaCl_2$+ 0.01% Brij, pH adjusted to pH 7.3) and the amylase activity measured using Phadebas amylase assay as described under methods. All measurements were made in triplicates. The residual activities were calculated as the ratio between the activity in the samples that have been incubated at 50° C. relative to activity in the samples that have been incubated at 4° C. Further the half-life and the improvement factor relative to WT (IF-WT) were calculated.

TABLE 18

Residual activity (RA) of alpha-amylase variants after incubation in pH 4.5 at 50° C. for 60 min.

| Amylase variants | RA | Half life (min) | IF (WT) |
|---|---|---|---|
| WT - reference | 19 | 25 | 1.00 |
| E190P | 0 | | |
| S244Q | 0 | | |
| S244W | 0 | | |

TABLE 18-continued

Residual activity (RA) of alpha-amylase variants
after incubation in pH 4.5 at 50° C. for 60 min.

| Amylase variants | RA | Half life (min) | IF (WT) |
|---|---|---|---|
| S244Y | 0 | | |
| S244F | 0 | | |
| S244H | 0 | | |
| S244Q | 0 | | |
| K281W | 0 | | |
| K281Y | 0 | | |
| K281F | 0 | | |
| K281I | 0 | | |
| E190P S244W | 96 | 996 | 5.09 |
| E190P S244Y | 59 | 78 | 3.11 |
| E190P S244H | 43 | 49 | 2.28 |
| E190P K281W | 35 | 40 | 1.88 |
| E190P K281F | 58 | 76 | 3.07 |

This example demonstrates that alpha-amylase variants with a single substitution in S244 or K281 have decreased stability at low pH. But when introduced in an amylase with a proline (P) in position 190 (numbers according to SEQ ID No: 7), these substitutions increase the stability at low pH significantly.

Example 17: Chelator Stability of *Bacillus* sp. AA110 Alpha-Amylase Variants of the Invention Amino acid substitutions were introduced in *Bacillus* sp. AA110 alpha-amylase (SEQ ID NO: 7) by standard site directed methods. The substitutions are indicated in the table below and the position numbering is according to SEQ ID NO: 7. The modified amylase genes were transformed into and expressed in *Bacillus subtilis*. The *Bacillus subtilis* broths were centrifuged and the amylase containing supernatants isolated and diluted 10 times in model detergent A with 0.5% EDTA so the resulting concentration is 90% detergent and 0.45% EDTA. The samples were then split in two samples; one was stored at 4° C. and the other was incubated at 50° C. for 90 minutes. Following that, the samples were diluted 10 times in 100 mM assay buffer (100 mM Britton-Robinson buffer (100 mM acetic acid+100 mM phosphate acid+100 mM boric acid)+0.12 mM CaCl$_2$+0.01% Brij, pH adjusted to pH 7.3) and the amylase activity measured using Phadebas amylase assay as described under methods. The residual activities were calculated as the ratio between the activity in the samples that have been incubated at 50° C. relative to activity in the samples that have been incubated at 4° C. Further the half-life and the improvement factor relative to WT (IF-WT) were calculated.

TABLE 19

Residual activity (RA) of alpha-amylase variants after incubation
in model detergent A with EDTA at 50° C. for 90 min.

| Amylase variants | RA | Half life (min) | IF (WT) |
|---|---|---|---|
| WT - reference | 25 | 45 | 1.00 |
| E190P | 0 | | |
| S244Q | 0 | | |
| S244W | 12 | 29 | 0.48 |
| S244Y | 0 | | |
| S244F | 0 | | |
| S244H | 0 | | |
| S244Q | 0 | | |
| K281W | 0 | | |
| K281Y | 0 | | |

TABLE 19-continued

Residual activity (RA) of alpha-amylase variants after incubation
in model detergent A with EDTA at 50° C. for 90 min.

| Amylase variants | RA | Half life (min) | IF (WT) |
|---|---|---|---|
| K281F | 0 | | |
| K281I | 0 | | |
| E190P S244W | 86 | 425 | 3.47 |
| E190P S244Y | 73 | 195 | 2.92 |
| E190P S244F | 75 | 222 | 3.04 |
| E190P S244H | 35 | 59 | 1.40 |
| E190P S244Q | 82 | 314 | 3.30 |
| E190P K281W | 26 | 46 | 1.04 |
| E190P K281Y | 35 | 59 | 1.41 |
| E190P K281I | 38 | 65 | 1.53 |

This example demonstrates that while alpha-amylase variants with a single substitution in S244 or K281 have destabilizing effect in detergent with EDTA. But when introduced in an amylase with a proline (P) in position 190 (numbers according to SEQ ID No: 7), the S244 to Q, W, Y, For Hand K281 to W, Y or I substitutions increase the stability significantly over the wild type reference.

Example 18: Low pH Stability of *Bacillus stearothermophilus* Alpha-Amylase Variants of the Invention Using standard site directed methods, amino acid substitutions were introduced in a variant of the *Bacillus stearothermophilus* wild type alpha-amylase (SEQ ID NO: 1 or SEQ ID NO: 27) having a proline at position 188 (E188P). The substitutions are indicated in the table below and the position numbering is according to SEQ ID NO: 1. The modified amylase genes were transformed into and expressed in *Bacillus subtilis*. The *Bacillus subtilis* broths were centrifuged and the amylase containing supernatants isolated and diluted 10 times in 100 mM K-acetate pH 4.5 with 5 ppm CaCl$_2$. The samples were then split in two samples; one was stored at 4° C. and the other was incubated at 60° C. for 30 minutes. Following that, the samples were diluted 10 times in assay buffer (100 mM Britton-Robinson buffer (100 mM acetic acid+100 mM phosphate acid+100 mM boric acid)+0.12 mM CaCl$_2$+0.01% Brij, pH adjusted to pH 7.3) and the amylase activity measured using Phadebas amylase assay as described under methods. The residual activities were calculated as the ratio between the activity in the samples that have been incubated at 60° C. relative to activity in the samples that have been incubated at 4° C. Further the half-live and the improvement factor relative to reference were calculated.

TABLE 20

Residual activity (RA) of alpha-amylase variants
after incubation in pH 4.5 at 60° C. for 30 min.

| Amylase variants | RA | Half life (min) | IF |
|---|---|---|---|
| E188P (ref.) | 31 | 18 | 1.0 |
| S242Q | 2 | 5 | 0.3 |
| S242Y | 45 | 26 | 1.5 |
| S242F | 54 | 34 | 1.9 |
| K279W | 44 | 26 | 1.4 |
| K279Y | 49 | 29 | 1.7 |
| S242Y K279i | 60 | 41 | 2.3 |

This example demonstrates that alpha-amylase variants, introduced in an amylase reference with a proline in position 188, with substitution in S242 to Y or F and/or in K279 to W, Y, or I have increased stability at low pH. Surprisingly, a destabilizing effect is observed for the substitution S242Q in combination with E188P.

Example 19: Low pH Stability of *Bacillus stearothermophilus* Alpha-Amylase Variants of the Invention Using standard site directed methods, amino acid substitutions were introduced in a variant of the *Bacillus stearothermophilus* wild type alpha-amylase (SEQ ID NO: 1 or 27) having two amino acid deletions in positions 180 and 181 and a proline at position 188 (E188P). The substitutions are indicated in the table below and the position numbering is according to SEQ ID NO: 1. The modified amylase genes were transformed into and expressed in *Bacillus subtilis*. The *Bacillus subtilis* broths were centrifuged and the amylase containing supernatants isolated and diluted 10 times in 100 mM K-acetate pH 4.5 with 5 ppm $CaCl_2$. The samples were then split in two samples; one was stored at 4° C. and the other was incubated at 70° C. for 30 minutes. Following that, the samples were diluted 10 times in assay buffer (100 mM Britton-Robinson buffer (100 mM acetic acid+100 mM phosphate acid+100 mM boric acid)+0.12 mM $CaCl_2$+0.01% Brij, pH adjusted to pH 7.3) and the amylase activity measured using Phadebas amylase assay as described under methods. The residual activities were calculated as the ratio between the activity in the samples that have been incubated at 70° C. relative to activity in the samples that have been incubated at 4° C. Further the half-live and the improvement factor relative to reference were calculated.

TABLE 21

Residual activity (RA) of alpha-amylase variants after incubation in pH 4.5 at 70° C. for 30 min.

| Amylase variants | RA | Half life (min) | IF |
| --- | --- | --- | --- |
| I181* G182* E188P | 47 | 27 | 1.0 |
| S242Q | 30 | 17 | 0.6 |
| S242F | 58 | 38 | 1.4 |
| K279W | 67 | 52 | 1.9 |
| K279Y | 63 | 45 | 1.6 |
| K279F | 64 | 46 | 1.7 |
| S242F K279W | 92 | 263 | 9.6 |
| S242H K279W | 79 | 88 | 3.2 |
| S242W K279W | 67 | 53 | 1.9 |
| S242Y K279i | 90 | 192 | 7.0 |
| S242Y K279I | 85 | 130 | 4.7 |
| S242Y K279F | 70 | 57 | 2.1 |
| S242Y K279H | 77 | 82 | 3.0 |

This example demonstrates that alpha-amylase variants, introduced in an amylase reference with deletions in positions 180 and 181 and a proline at position 188, with substitution in S242 to Y, W or F and in K279 to W, Y, F, H, I or L have increased stability at low pH. Surprisingly, a destabilizing effect is observed for the substitution S242Q in combination with a double deletion in positions 180 and 181 and a proline at position 188.

Example 20: Low pH Stability of *Bacillus sp.* TS-23 Alpha-Amylase Variants of the Invention Using standard site directed methods, amino acid substitutions were introduced in a variant of the *Bacillus sp.* TS-23 alpha-amylase (SEQ ID NO: 4) having two amino acid deletion in positions 180 and 181, a proline at position 189 (E189P) and a deletion of the CBM20 domain corresponding to amino acid 485 to 583, in SEQ ID NO: 4. The substitutions are indicated in the table below and the position numbering is according to SEQ ID NO: 4. The modified amylase genes were transformed into and expressed in *Bacillus subtilis*. The *Bacillus subtilis* broths were centrifuged and the amylase containing supernatants isolated and diluted 10 times in 100 mM K-acetate pH 4.5 with 5 ppm $CaCl_2$. The samples were then split in two samples; one was stored at 4° C. and the other was incubated at 50° C. for 30 minutes. Following that, the samples were diluted 10 times in assay buffer (100 mM Britton-Robinson buffer (100 mM acetic acid+100 mM phosphate acid+100 mM boric acid)+0.12 mM $CaCl_2$+0.01% Brij, pH adjusted to pH 7.3) and the amylase activity measured using Phadebas amylase assay as described under methods. The residual activities were calculated as the ratio between the activity in the samples that have been incubated at 50° C. relative to activity in the samples that have been incubated at 4° C. Further the half-live and the improvement factor relative to reference were calculated.

TABLE 22

Residual activity (RA) of alpha-amylase variants after incubation in pH 4.5 at 50° C. for 30 min.

| Amylase variants | RA | Half life (min) | IF |
| --- | --- | --- | --- |
| Ref. (180* + S181* + E189P + CBM20-del) | 27 | 16 | 1.0 |
| S243Q | 4 | 6 | 0.4 |
| S243W | 77 | 82 | 5.1 |
| S243Y | 76 | 78 | 4.9 |
| S243F | 95 | 432 | 27.2 |
| K280Y | 74 | 68 | 4.3 |
| K280F | 66 | 50 | 3.2 |
| K280H | 87 | 147 | 9.3 |
| K280W | 97 | 584 | 36.8 |
| S243Y K280W | 94 | 341 | 21.5 |
| S243F K280W | 84 | 119 | 7.5 |
| S243H K280W | 67 | 53 | 3.3 |
| S243Y K280Y | 76 | 75 | 4.7 |
| S243Y K280F | 58 | 38 | 2.4 |
| S243Y K280H | 75 | 71 | 4.5 |

This example demonstrates that alpha-amylase variants, introduced in an amylase reference with deletions in positions 180 and 181, a proline at position 189 and a deletion of the CBM20 domain (SEQ ID NO: 4), with substitution in S243 to Y, W, For Hand in K280 to W, Y, For H have increased stability at low pH. Surprisingly, a destabilizing effect is observed for the substitution S243Q in combination with a double deletion in positions 180 and 181 and a proline at position 189.

Example 21: Increased Stability of Alpha-Amylase Variants of the Invention

In the examples above, substitutions of S239 and/or K276 in combination with the E185P substitution in SEQ. ID. NO. 2 and corresponding substitutions in other amylases, have been shown to increase the stability of the amylases. Corresponding amino acids in other amylases, in particular in amylases belonging to the CAZY family GH13_5, can be identified by sequence alignment using eg. Crystal X software package or similar protein sequence alignment software, or by structural alignment using eg. Pymol software package or similar protein structure display software. At least one of these positions are substituted to W, Y, F, H, I or L in combination with an proline introduction at the position corresponding to E185P in SEQ. ID. NO. 2 to generate alph.-amylases with increase stability.

Eg. in SEQ ID NO: 12, G245W, Y, F, H, I or L substitutions in combination with the D191P and/or R282W, Y, F, H, I or L substitutions in combination with the D191P are introduced.

In SEQ ID NO. 13, G239W, Y, F, H, I or L substitutions in combination with the D185P and/or R276W, Y, F, H, I or L substitutions in combination with the D185P are introduced.

In SEQ ID NO: 14, D240W, Y, F, H, I or L substitutions in combination with the E186P and/or K277W, Y, F, H, I or L substitutions in combination with the E186P are introduced.

In SEQ ID NO: 15, D241W, Y, F, H, I or L substitutions in combination with the N187P and/or V278W, Y, F, H, I or L substitutions in combination with the N187P are introduced.

In SEQ ID NO: 16, D244W, Y, F, H, I or L substitutions in combination with the E190P and/or K282W, Y, F, H, I or L substitutions in combination with the E190P are introduced.

In SEQ ID NO: 17, S239W, Y, F, H, I or L substitutions in combination with the E185P and/or K276W, Y, F, H, I or L substitutions in combination with the E185P are introduced.

In SEQ ID NO: 18, A240W, Y, F, H, I or L substitutions in combination with the G186P and/or S277W, Y, F, H, I or L substitutions in combination with the G186P are introduced.

The reference amylase and the modified amylase genes are transformed into and expressed in *Bacillus subtilis*, the broths are centrifuged and the amylase containing supernatants are used for determining the stability under stressed conditions, eg. in 100 mM K-acetate pH 4.5 with 5 ppm $CaCl_2$ or eg. in a model detergent with 0.5% EDTA. After incubation, the samples are diluted 10 times in assay buffer (100 mM Britton-Robinson buffer (100 mM acetic acid+100 mM phosphate acid+100 mM boric acid) with 0.12 mM $CaCl_2$+0.01% Brij, pH adjusted to pH 7.3) and the amylase activity measured using Phadebas amylase assay as described under methods. All measurements are made in triplicates. The residual activities are calculated as the ratio between the activity in the samples that is incubated at stressing temperature relative to activity in the samples that is incubated at 4° C. From the residual activity, the half-live and the improvement factor relative to reference amylase, i.e. the starting point for the specific modifications are calculated.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

---

The invention claimed is:

1. An alpha-amylase variant comprising a substitution at a position corresponding to position 188 and at least one further substitution at a position corresponding to position 242 or 279 or 275 of SEQ ID NO: 1, the variant comprising one or more combinations of substitutions selected from the group consisting of E188P+S242Y, E188P+S242F, E188P+S242H, E188P+S242W, E188P+S242P, E188P+S242I, E188P+S242L, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H, wherein the variant has at least 70%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

2. The variant alpha-amylase according to claim 1, wherein the variant has increased thermo-stability at pH 4.5 over the parent alpha-amylase.

3. The variant according to claim 1, wherein the variant has increased chelator stability in model detergent A over the parent alpha-amylase.

4. The variant according to claim 1, wherein the variant is capable of generating a liquefact having a dextrose equivalent (DE) value higher than the DE value generated by a parent alpha-amylase.

5. The variant according to claim 1, wherein the variant is capable of generating a liquefact having decreased viscosity compared to the liquefact generated by a parent alpha-amylase.

6. The variant alpha-amylase according to claim 1, wherein the variant has increased thermo-stability at pH 4.5, wherein increased stability is determined as an improvement factor (IF) over the parent alpha-amylase, and wherein the variant has an IF of at least 1.1.

7. The variant according to claim 1, wherein the variant has increased chelator stability in model detergent A, wherein increased stability is determined as an improvement factor (IF) over the parent alpha-amylase, wherein the variant has an IF of at least 1.1.

8. The variant according to claim 1 wherein the variant further comprises a deletion of two amino acids in the region corresponding to positions 179-182 using SEQ ID NO: 1 for numbering.

9. The variant according to claim 8, wherein the deletion is selected from the group consisting of 179*+180*, 179*+181*, 179*+182*, 180*+181*, 180*+182*, and 181*+182*.

10. The variant according to claim 1, wherein the parent alpha-amylase is SEQ ID NO: 3 and, wherein the variant comprises the specific substitutions corresponding to:

G48A+T49I+H68W+G107A+H156Y+A181T+A209V+ Q264S+K176L+F201Y+H205Y+K213T+E255P+ Q360S+D416V+R437W using SEQ ID NO: 2 for numbering; or G48A+T49I+H68W+G107A+T116Q+H156Y+A181T+ A209V+Q264S+K176L+F201Y+H205Y+K213T+ E255P+Q360S+D416V+R437W using SEQ ID NO: 2 for numbering; and wherein the variant has at least 75%, but less than 100% sequence identity to SEQ ID NO: 3.

11. The variant according to claim 1, wherein the parent alpha-amylase is SEQ ID NO: 1 and, wherein the variant further comprises the specific substitutions corresponding to:

V59A+E129V+E177L+R179E+Q254S+M284V+ V212T+Y268G+N293Y+T297N, and wherein the variant has at least 75%, but less than 100% sequence identity to SEQ ID NO: 1 or SEQ ID NO: 27.

12. The variant according to claim 1, comprising a combination of substitutions selected from the group consisting of:
E188P+S242Y+K279I;
E188P+S242L+K279W;
E188P+S242P+K279W;
E188P+S242L+K279I;
E188P+S242Y+K279W;
E188P+S242Y+K279F;
E188P+S242Y+K279H;
E188P+S242Y+K279L;
E188P+S242Y+K279Y;
E188P+S242P+K279I;
E188P+S242F+K279W;
E188P+S242H+K279W; and
E188P+S242W+K279W.

13. The variant of claim 1, further comprising a substitution corresponding to I204Y using SEQ ID NO: 1 for numbering, wherein the variant comprises the combinations of substitutions selected from the group consisting of:
E188P+I204Y+S242Y;
E188P+I204Y+S242F;
E188P+I204Y+K279W;
E188P+I204Y+K279Y;
E188P+I204Y+K279F;
E188P+I204Y+K279H;
E188P+I204Y+K279I; and
E188P+I204Y+K279L.

14. The variant according to claim 1, wherein the number of alterations is 2-20.

15. A composition comprising the variant alpha-amylase of claim 1.

16. A polynucleotide encoding the variant of claim 1.

17. A nucleic acid construct comprising the polynucleotide of claim 16.

18. An expression vector comprising the polynucleotide of claim 16.

19. An isolated recombinant host cell comprising the polynucleotide of claim 16.

20. A method of producing an alpha-amylase variant having alpha-amylase activity, comprising:
a) cultivating the host cell of claim 19 under conditions suitable for expression of the variant; and
b) optionally recovering the variant.

21. A process of liquefying a starch-containing material, comprising contacting the starch-containing material with the variant of claim 1.

22. A process for producing a syrup from starch-containing material comprising the steps of:
a) liquefying the starch-containing material at a temperature above the initial gelatinization temperature in the presence of a variant alpha-amylase according to claim 1; and
b) saccharifying the product of step a) in the presence of a glucoamylase.

23. A method for increasing stability of a parent alpha-amylase comprising introducing a substitution at a position corresponding to position 188 and at least one further substitution at a position corresponding to position 242, 279 or 275 of SEQ ID NO: 1, wherein the at least one further substitution comprises a combinations of substitutions selected from the group consisting of E188P+S242Y, E188P+S242F, E188P+S242H, E188P+S242W, E188P+S242P, E188P+S242I, E188P+S242T, E188P+S242L, E188P+K279W, E188P+K279Y, E188P+K279F, E188P+K279H, E188P+K279I, E188P+K279L, E188P+K279D, E188P+K279M, E188P+K279S, E188P+K279T, E188P+K279N, E188P+K279Q, E188P+K279V, E188P+K279A, E188P+N275F, E188P+N275Y, E188P+N275W, and E188P+N275H.

24. The variant according to claim 1, which comprises the substitutions E188P+S242Y, wherein the variant has at least 75%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

25. The variant according to claim 1, which comprises the substitutions E188P+S242Y, wherein the variant has at least 80%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

26. The variant according to claim 1, which comprises the substitutions E188P+S242Y, wherein the variant has at least 85%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

27. The variant according to claim 1, which comprises the substitutions E188P+S242Y, wherein the variant has at least 90%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

28. The variant according to claim 1, which comprises the substitutions E188P+S242Y, wherein the variant has at least 95%, but less than 100% sequence identity to a parent alpha amylase selected from the group consisting of: SEQ ID NO:

1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

29. The variant according to claim 1, which comprises the substitutions E188P+S242Y, wherein the variant has at least 98%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

30. The variant according to claim 1, which comprises the substitutions E188P+S242F, wherein the variant has at least 75%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

31. The variant according to claim 1, which comprises the substitutions E188P+S242F, wherein the variant has at least 80%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

32. The variant according to claim 1, which comprises the substitutions E188P+S242F, wherein the variant has at least 85%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

33. The variant according to claim 1, which comprises the substitutions E188P+S242F, wherein the variant has at least 90%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

34. The variant according to claim 1, which comprises the substitutions E188P+S242F, wherein the variant has at least 95%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

35. The variant according to claim 1, which comprises the substitutions E188P+S242F, wherein the variant has at least 98%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

36. The variant according to claim 1, which comprises the substitutions E188P+S242H, wherein the variant has at least 75%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

37. The variant according to claim 1, which comprises the substitutions E188P+S242H, wherein the variant has at least 80%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

38. The variant according to claim 1, which comprises the substitutions E188P+S242H, wherein the variant has at least 85%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

39. The variant according to claim 1, which comprises the substitutions E188P+S242H, wherein the variant has at least 90%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

40. The variant according to claim 1, which comprises the substitutions E188P+S242H, wherein the variant has at least 95%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

41. The variant according to claim 1, which comprises the substitutions E188P+S242H, wherein the variant has at least 98%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO:

12, SEQ ID NO: 13, SEQ ID NO: 14, SEQ ID NO: 15, SEQ ID NO: 16, SEQ ID NO: 17, SEQ ID NO: 18, and SEQ ID NO: 27.

42. The variant according to claim 1, which comprises the substitutions E188P+S242W, wherein the variant has at least 75%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

43. The variant according to claim 1, which comprises the substitutions E188P+S242W, wherein the variant has at least 80%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

44. The variant according to claim 1, which comprises the substitutions E188P+S242W, wherein the variant has at least 85%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

45. The variant according to claim 1, which comprises the substitutions E188P+S242W, wherein the variant has at least 90%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

46. The variant according to claim 1, which comprises the substitutions E188P+S242W, wherein the variant has at least 95%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

47. The variant according to claim 1, which comprises the substitutions E188P+S242W, wherein the variant has at least 98%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

48. The variant according to claim 1, which comprises the substitutions E188P+S242P, wherein the variant has at least 75%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

49. The variant according to claim 1, which comprises the substitutions E188P+S242P, wherein the variant has at least 80%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

50. The variant according to claim 1, which comprises the substitutions E188P+S242P, wherein the variant has at least 85%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

51. The variant according to claim 1, which comprises the substitutions E188P+S242P, wherein the variant has at least 90%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

52. The variant according to claim 1, which comprises the substitutions E188P+S242P, wherein the variant has at least 95%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

53. The variant according to claim 1, which comprises the substitutions E188P+S242P, wherein the variant has at least 98%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

54. The variant according to claim 1, which comprises the substitutions E188P+S242I, wherein the variant has at least 75%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

55. The variant according to claim 1, which comprises the substitutions E188P+S242I, wherein the variant has at least 80%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

56. The variant according to claim 1, which comprises the substitutions E188P+S242I, wherein the variant has at least 85%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

57. The variant according to claim 1, which comprises the substitutions E188P+S242I, wherein the variant has at least 90%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

58. The variant according to claim 1, which comprises the substitutions E188P+S242I, wherein the variant has at least 95%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

59. The variant according to claim 1, which comprises the substitutions E188P+S242I, wherein the variant has at least 98%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

60. The variant according to claim 1, which comprises the substitutions E188P+S242T, wherein the variant has at least 75%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

61. The variant according to claim 1, which comprises the substitutions E188P+S242T, wherein the variant has at least 80%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

62. The variant according to claim 1, which comprises the substitutions E188P+S242T, wherein the variant has at least 85%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

63. The variant according to claim 1, which comprises the substitutions E188P+S242T, wherein the variant has at least 90%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

64. The variant according to claim 1, which comprises the substitutions E188P+S242T, wherein the variant has at least 95%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

65. The variant according to claim 1, which comprises the substitutions E188P+S242T, wherein the variant has at least 98%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

66. The variant according to claim 1, which comprises the substitutions E188P+S242L, wherein the variant has at least 75%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

67. The variant according to claim 1, which comprises the substitutions E188P+S242L, wherein the variant has at least 80%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

68. The variant according to claim 1, which comprises the substitutions E188P+S242L, wherein the variant has at least 85%, but less than 100% sequence identity to a parent alpha amylase selected from the group consisting of: SEQ ID NO:

1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

69. The variant according to claim 1, which comprises the substitutions E188P+S242L, wherein the variant has at least 90%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

70. The variant according to claim 1, which comprises the substitutions E188P+S242L, wherein the variant has at least 95%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

71. The variant according to claim 1, which comprises the substitutions E188P+S242L, wherein the variant has at least 98%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

* * * * *

UNITED STATES PATENT AND TRADEMARK OFFICE
CERTIFICATE OF CORRECTION

PATENT NO. : 11,326,153 B2
APPLICATION NO. : 16/770797
DATED : May 10, 2022
INVENTOR(S) : Andersen et al.

It is certified that error appears in the above-identified patent and that said Letters Patent is hereby corrected as shown below:

In the Claims

Please amend Claim 54 Column 172, Lines 58-67 as follows:
54. The variant according to claim 1, which comprises the substitutions E188P+S242I, wherein the variant has at least 75%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

Please amend Claim 55 Column 173, Lines 1-10 as follows:
55. The variant according to claim 1, which comprises the substitutions E188P+S242I, wherein the variant has at least 80%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

Please amend Claim 56 Column 173, Lines 11-20 as follows:
56. The variant according to claim 1, which comprises the substitutions E188P+S242I, wherein the variant has at least 85%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

Please amend Claim 57 Column 173, Lines 21-30 as follows:
57. The variant according to claim 1, which comprises the substitutions E188P+S242I, wherein the variant has at least 90%, but less than 100% sequence identity to a parent alpha amylase selected Signed and Sealed this
First Day of August, 2023

Katherine Kelly Vidal
*Director of the United States Patent and Trademark Office*

CERTIFICATE OF CORRECTION (continued)
U.S. Pat. No. 11,326,153 B2 from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

Please amend Claim 58 Column 173, Lines 31-40 as follows:
58. The variant according to claim 1, comprises the substitutions E188P+S242I, wherein the variant has at least 95%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.

Please amend Claim 59 Column 173, Lines 41-50 as follows:
59. The variant according to claim 1, which comprises the substitutions E188P+S242I, wherein the variant has at least 98%, but less than 100% sequence identity to a parent alpha amylase selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 27.